(12) United States Patent
Paliwoda

(10) Patent No.: US 12,150,765 B2
(45) Date of Patent: *Nov. 26, 2024

(54) RELEASEABLE CATHETER HUB RETAINER

(71) Applicant: Smiths Medical ASD, Inc., Plymouth, MN (US)

(72) Inventor: Brian Paliwoda, Thomaston, CT (US)

(73) Assignee: ICU Medical, Inc., San Clemente, CA (US)

( * ) Notice: Subject to any disclaimer, the term of this patent is extended or adjusted under 35 U.S.C. 154(b) by 621 days.

This patent is subject to a terminal disclaimer.

(21) Appl. No.: 16/743,790

(22) Filed: Jan. 15, 2020

(65) Prior Publication Data

US 2020/0146605 A1    May 14, 2020

Related U.S. Application Data

(63) Continuation of application No. 15/012,013, filed on Feb. 1, 2016, now Pat. No. 10,548,522.
(Continued)

(51) Int. Cl.
*A61M 25/06* (2006.01)
*A61B 5/145* (2006.01)
(Continued)

(52) U.S. Cl.
CPC ........ *A61B 5/150824* (2013.01); *A61B 5/145* (2013.01); *A61B 5/15003* (2013.01);
(Continued)

(58) Field of Classification Search
CPC ............ A61M 25/0631; A61M 5/3232; A61M 2005/3228; A61M 25/0612;
(Continued)

(56) References Cited

U.S. PATENT DOCUMENTS 5,000,740 A    3/1991   Ducharme et al.
5,215,528 A    6/1993   Purdy et al.
(Continued)

FOREIGN PATENT DOCUMENTS

CN    1427731 A    7/2003
CN    102387831 A  3/2012
(Continued)

OTHER PUBLICATIONS

Application and File History for U.S. Appl. No. 15/012,013, filed Feb. 1, 2016, Inventors Akcay, et al.
(Continued)

*Primary Examiner* — James D Ponton
*Assistant Examiner* — Hong-Van N Trinh
(74) *Attorney, Agent, or Firm* — Louis Woo

(57) ABSTRACT

A safety catheter insertion assembly including a catheter hub coupling assembly. The safety catheter insertion assembly having a needle hub slideably coupled to a needle housing such that the needle hub is moveable between a first position wherein an insertion needle extends from the needle housing, and a second position wherein the sharp distal tip is housed within the needle housing, the catheter hub coupling assembly coupling the catheter hub to the needle housing in the first position and releasing the catheter hub from the needle housing in the second position.

18 Claims, 26 Drawing Sheets

Related U.S. Application Data

(60) Provisional application No. 62/109,755, filed on Jan. 30, 2015, provisional application No. 62/109,710, filed on Jan. 30, 2015, provisional application No. 62/109,766, filed on Jan. 30, 2015, provisional application No. 62/109,742, filed on Jan. 30, 2015, provisional application No. 62/109,715, filed on Jan. 30, 2015, provisional application No. 62/109,673, filed on Jan. 30, 2015, provisional application No. 62/109,735, filed on Jan. 30, 2015, provisional application No. 62/109,759, filed on Jan. 30, 2015, provisional application No. 62/109,722, filed on Jan. 30, 2015, provisional application No. 62/109,745, filed on Jan. 30, 2015, provisional application No. 62/109,750, filed on Jan. 30, 2015.

(51) Int. Cl.
| | | |
|---|---|---|
| *A61B 5/15* | (2006.01) | |
| *A61B 5/153* | (2006.01) | |
| *A61M 5/32* | (2006.01) | |
| *A61M 5/42* | (2006.01) | |
| *A61M 21/02* | (2006.01) | |
| *A61M 25/00* | (2006.01) | |
| *A61B 5/1477* | (2006.01) | |
| *A61B 5/157* | (2006.01) | |
| *A61B 10/00* | (2006.01) | |
| *A61B 17/132* | (2006.01) | |
| *A61M 21/00* | (2006.01) | |
| *A61M 39/22* | (2006.01) | |

(52) U.S. Cl.
CPC .. *A61B 5/150221* (2013.01); *A61B 5/150641* (2013.01); *A61B 5/150732* (2013.01); *A61B 5/1535* (2013.01); *A61M 5/3202* (2013.01); *A61M 5/3232* (2013.01); *A61M 5/422* (2013.01); *A61M 21/02* (2013.01); *A61M 25/0097* (2013.01); *A61M 25/0606* (2013.01); *A61M 25/0631* (2013.01); *A61B 5/14539* (2013.01); *A61B 5/1477* (2013.01); *A61B 5/150213* (2013.01); *A61B 5/150259* (2013.01); *A61B 5/150389* (2013.01); *A61B 5/150503* (2013.01); *A61B 5/150992* (2013.01); *A61B 5/157* (2013.01); *A61B 2010/0006* (2013.01); *A61B 17/1325* (2013.01); *A61M 2005/3247* (2013.01); *A61M 2021/0016* (2013.01); *A61M 25/0693* (2013.01); *A61M 39/22* (2013.01); *A61M 2205/0205* (2013.01)

(58) Field of Classification Search
CPC ............ A61M 25/0618; A61M 5/3271; A61M 2005/3247; A61M 25/0693; A61M 25/0606; A61M 25/0097; A61M 2005/325
See application file for complete search history.

(56) References Cited

U.S. PATENT DOCUMENTS

| | | |
|---|---|---|
| 5,279,590 A | 1/1994 | Sinko et al. |
| 5,599,310 A | 2/1997 | Bogert |
| 5,676,658 A * | 10/1997 | Erskine ............... A61M 5/3269 604/165.03 |
| 5,700,250 A | 12/1997 | Erskine |
| 5,713,876 A | 2/1998 | Bogert et al. |
| 5,718,688 A | 2/1998 | Wozencroft |
| 5,795,339 A | 8/1998 | Erskine |
| 5,853,339 A | 12/1998 | Scerbo |
| 5,853,393 A | 12/1998 | Bogert |
| 5,911,705 A | 6/1999 | Howell |
| 5,935,109 A | 8/1999 | Donnan |
| 5,951,515 A | 9/1999 | Osterlind |
| 6,004,294 A | 12/1999 | Brimhall et al. |
| 6,056,726 A | 5/2000 | Isaacson |
| 6,077,244 A | 6/2000 | Botich et al. |
| 6,117,108 A | 9/2000 | Woehr et al. |
| 6,213,978 B1 | 4/2001 | Voyten |
| 6,221,047 B1 | 4/2001 | Greene et al. |
| 6,287,278 B1 | 9/2001 | Woehr et al. |
| D448,844 S | 10/2001 | Reis |
| 6,379,332 B1 | 4/2002 | Van Landuyt |
| 6,379,333 B1 | 4/2002 | Brimhall et al. |
| 6,461,362 B1 | 10/2002 | Halseth et al. |
| 6,585,703 B1 | 7/2003 | Kassel et al. |
| 6,595,955 B2 | 7/2003 | Ferguson et al. |
| 6,616,630 B1 | 9/2003 | Woehr et al. |
| 6,652,490 B2 | 11/2003 | Howell |
| 6,663,592 B2 | 12/2003 | Rhad et al. |
| 6,709,419 B2 | 3/2004 | Woehr |
| 6,749,588 B1 | 6/2004 | Howell et al. |
| 6,796,962 B2 | 9/2004 | Ferguson et al. |
| 6,902,546 B2 | 6/2005 | Ferguson |
| 6,914,212 B2 | 7/2005 | Adams |
| 6,972,002 B2 | 12/2005 | Thorne |
| 6,984,213 B2 | 1/2006 | Horner et al. |
| 6,986,760 B2 | 1/2006 | Giambattista et al. |
| 7,002,098 B2 | 2/2006 | Adams |
| 7,004,927 B2 | 2/2006 | Ferguson et al. |
| 7,008,402 B2 | 3/2006 | Ferguson et al. |
| 7,106,269 B1 | 9/2006 | Tonn |
| 7,125,397 B2 | 10/2006 | Woehr et al. |
| 7,179,244 B2 | 2/2007 | Smith et al. |
| 7,186,239 B2 | 3/2007 | Woehr |
| 7,214,211 B2 | 5/2007 | Woehr et al. |
| 7,226,434 B2 | 6/2007 | Carlyon et al. |
| 7,255,685 B2 | 8/2007 | Pressly, Sr. et al. |
| 7,264,613 B2 | 9/2007 | Woehr et al. |
| 7,291,130 B2 | 11/2007 | McGurk |
| 7,314,462 B2 | 1/2008 | O'Reagan et al. |
| 7,341,573 B2 | 3/2008 | Ferguson et al. |
| 7,357,784 B2 | 4/2008 | Ferguson |
| 7,413,562 B2 | 8/2008 | Ferguson et al. |
| 7,458,954 B2 | 12/2008 | Ferguson et al. |
| 7,507,222 B2 | 3/2009 | Cindrich et al. |
| 7,604,616 B2 | 10/2009 | Thoresen et al. |
| 7,608,057 B2 | 10/2009 | Woehr et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| D608,886 S | 1/2010 | Rueckert et al. |
| 7,654,988 B2 | 2/2010 | Moulton et al. |
| 7,658,725 B2 | 2/2010 | Bialecki et al. |
| 7,713,248 B2 | 5/2010 | Lopez |
| 7,722,569 B2 | 5/2010 | Soderholm et al. |
| 7,731,691 B2 | 6/2010 | Cote et al. |
| 7,736,332 B2 | 6/2010 | Carlyon et al. |
| 7,736,342 B2 | 6/2010 | Abriles et al. |
| 7,798,994 B2 | 9/2010 | Brimhall |
| 7,806,849 B2 | 10/2010 | Woehr |
| 7,828,774 B2 | 11/2010 | Harding et al. |
| 7,935,080 B2 | 5/2011 | Howell et al. |
| 7,972,313 B2 | 7/2011 | Woehr et al. |
| 7,976,502 B2 | 7/2011 | Baid |
| 7,988,664 B2 | 8/2011 | Fiser et al. |
| 8,096,973 B2 | 1/2012 | Snow et al. |
| 8,100,858 B2 | 1/2012 | Woehr et al. |
| 8,162,904 B2 | 4/2012 | Takano et al. |
| 8,211,070 B2 | 7/2012 | Woehr et al. |
| 8,216,188 B2 | 7/2012 | Millerd et al. |
| 8,257,322 B2 | 9/2012 | Koehler et al. |
| 8,292,852 B2 | 10/2012 | Mulholland et al. |
| 8,348,893 B2 | 1/2013 | Carlyon |
| 8,376,994 B2 | 2/2013 | Woehr et al. |
| 8,382,718 B2 | 2/2013 | Woehr |
| 8,382,721 B2 | 2/2013 | Woehr et al. |
| 8,394,064 B2 | 3/2013 | Baid |

(56) References Cited

U.S. PATENT DOCUMENTS

| | | | |
|---|---|---|---|
| 8,414,539 B1 | 4/2013 | Kuracina et al. |
| 8,444,605 B2 | 5/2013 | Kuracina et al. |
| 8,460,249 B2 | 6/2013 | Woehr |
| 8,474,300 B2 | 7/2013 | McKinnon et al. |
| 8,486,024 B2 | 7/2013 | Steube |
| 8,496,623 B2 | 7/2013 | Burkholz |
| 8,506,528 B2 | 8/2013 | Fiser et al. |
| 8,529,515 B2 | 9/2013 | Woehr et al. |
| 8,545,454 B2 | 10/2013 | Kuracina et al. |
| 8,568,372 B2 | 10/2013 | Woehr et al. |
| 8,591,467 B2 | 11/2013 | Walker et al. |
| 8,647,313 B2 | 2/2014 | Woehr et al. |
| 8,702,658 B2 | 4/2014 | Spearman |
| D709,188 S | 7/2014 | Guala |
| 8,784,387 B2 | 7/2014 | Woehr |
| 8,814,833 B2 | 8/2014 | Farrell et al. |
| 8,821,439 B2 | 9/2014 | Kuracina et al. |
| 8,827,965 B2 | 9/2014 | Woehr et al. |
| 8,834,422 B2 | 9/2014 | Walker et al. |
| 8,845,584 B2 | 9/2014 | Ferguson et al. |
| 8,864,714 B2 | 10/2014 | Harding et al. |
| 8,915,883 B2 | 12/2014 | Baid |
| 8,926,563 B2 | 1/2015 | Steube |
| 8,936,575 B2 | 1/2015 | Moulton |
| 8,956,328 B2 | 2/2015 | Antonucci |
| 9,089,673 B2 | 7/2015 | Fiser et al. |
| 9,138,564 B2 | 9/2015 | Morrissey et al. |
| 9,180,277 B2 | 11/2015 | Erskine |
| 9,808,580 B2 | 11/2017 | Elmen |
| 10,028,691 B2 | 7/2018 | Goral et al. |
| D844,774 S | 4/2019 | Akcay et al. |
| 10,548,522 B2 | 2/2020 | Akcay et al. |
| 2002/0133122 A1 | 9/2002 | Giambattista et al. |
| 2003/0083621 A1 | 5/2003 | Shaw et al. |
| 2003/0199827 A1* | 10/2003 | Thorne ............ A61M 25/0631 604/164.08 |
| 2004/0225260 A1 | 11/2004 | Villa et al. |
| 2005/0273057 A1 | 12/2005 | Popov |
| 2007/0191776 A1 | 8/2007 | Bialecki et al. |
| 2011/0319825 A1* | 12/2011 | Goral ............... A61M 25/0618 604/164.01 |
| 2012/0035552 A1 | 2/2012 | Woehr |
| 2012/0226239 A1 | 9/2012 | Green |
| 2013/0030391 A1 | 1/2013 | Baid |
| 2013/0178825 A1 | 7/2013 | Helm, Jr. |
| 2013/0184645 A1 | 7/2013 | Baid |
| 2013/0253443 A1 | 9/2013 | Woehr et al. |
| 2013/0281972 A1 | 10/2013 | Newby |
| 2013/0296805 A1 | 11/2013 | Erskine |
| 2013/0317426 A1 | 11/2013 | Fiser et al. |
| 2013/0317440 A1 | 11/2013 | Woehr et al. |
| 2014/0018738 A1 | 1/2014 | Steube |
| 2014/0025009 A1 | 1/2014 | Erskine |
| 2014/0039399 A1* | 2/2014 | Burkholz ......... A61M 25/0631 604/164.08 |
| 2014/0046272 A1* | 2/2014 | Erskine ............ A61M 25/0009 604/263 |
| 2014/0058329 A1 | 2/2014 | Walker et al. |
| 2014/0135701 A1 | 5/2014 | Woehr et al. |
| 2014/0163470 A1 | 6/2014 | Baid |
| 2014/0249488 A1 | 9/2014 | Woehr |
| 2014/0257202 A1 | 9/2014 | Woehr |
| 2014/0336583 A1 | 11/2014 | Morrissey et al. |
| 2014/0371715 A1 | 12/2014 | Farrell et al. |
| 2015/0005666 A1 | 1/2015 | Terasawa et al. |
| 2015/0005718 A1 | 1/2015 | Walker et al. |
| 2015/0032065 A1 | 1/2015 | Ferguson et al. |
| 2015/0039009 A1 | 2/2015 | Tamano et al. |
| 2015/0073304 A1 | 3/2015 | Millerd |
| 2015/0080801 A1 | 3/2015 | Tanabe et al. |
| 2015/0126932 A1 | 5/2015 | Knutsson |
| 2015/0126933 A1 | 5/2015 | Antonucci |
| 2015/0174374 A1 | 6/2015 | Woehr |
| 2015/0196737 A1 | 7/2015 | Baid |
| 2015/0224267 A1 | 8/2015 | Farrell et al. |
| 2016/0220161 A1 | 8/2016 | Goral et al. |
| 2016/0220762 A1 | 8/2016 | Goral et al. |
| 2016/0220791 A1 | 8/2016 | Akcay et al. |
| 2016/0220805 A1 | 8/2016 | Goral et al. |
| 2018/0296149 A1 | 10/2018 | Goral et al. |

FOREIGN PATENT DOCUMENTS

| | | |
|---|---|---|
| CN | 103007383 A | 4/2013 |
| EP | 1011764 B1 | 2/2004 |
| EP | 1292355 B1 | 5/2007 |
| EP | 1448251 B1 | 7/2014 |
| GB | 2508466 B | 10/2014 |
| WO | WO-0241932 A3 | 5/2003 |
| WO | WO-2006070358 A3 | 3/2007 |
| WO | WO-2012014017 A1 | 2/2012 |
| WO | WO-2012014018 A1 | 2/2012 |
| WO | WO-2013187827 A1 | 12/2013 |
| WO | WO-2014097110 A1 | 6/2014 |
| WO | WO-2014162377 A1 | 10/2014 |
| WO | WO-2015023358 A1 | 2/2015 |
| WO | WO-2015056148 A1 | 4/2015 |

OTHER PUBLICATIONS

Application and File History for U.S. Appl. No. 29/581,199, filed Oct. 171, 2016, Inventors Akcay, et al.

Examination Report for Australian Application No. 2016211195, dated Jun. 22, 2018, 2 pages.

Extended European Search Report for Application No. 16744268.0, mailed on Aug. 7, 2018, 7 pages.

International Preliminary Report on Patentability for Application No. PCT/US2016/015958, mailed on Aug. 10, 2017, 9 pages.

International Search Report and Written Opinion for Application No. PCT/US2016/015958, mailed on Jun. 1, 2016, 12 pages.

Notice of Acceptance for Australian Application No. 2016211195, dated Jul. 1, 2019, 3 pages.

Office Action dated Sep. 3, 2019 for Chinese Application No. 201680008123.7, 16 pages.

Office Action dated Apr. 7, 2020 for Chinese Application No. 201680008123.7, 12 pages.

* cited by examiner

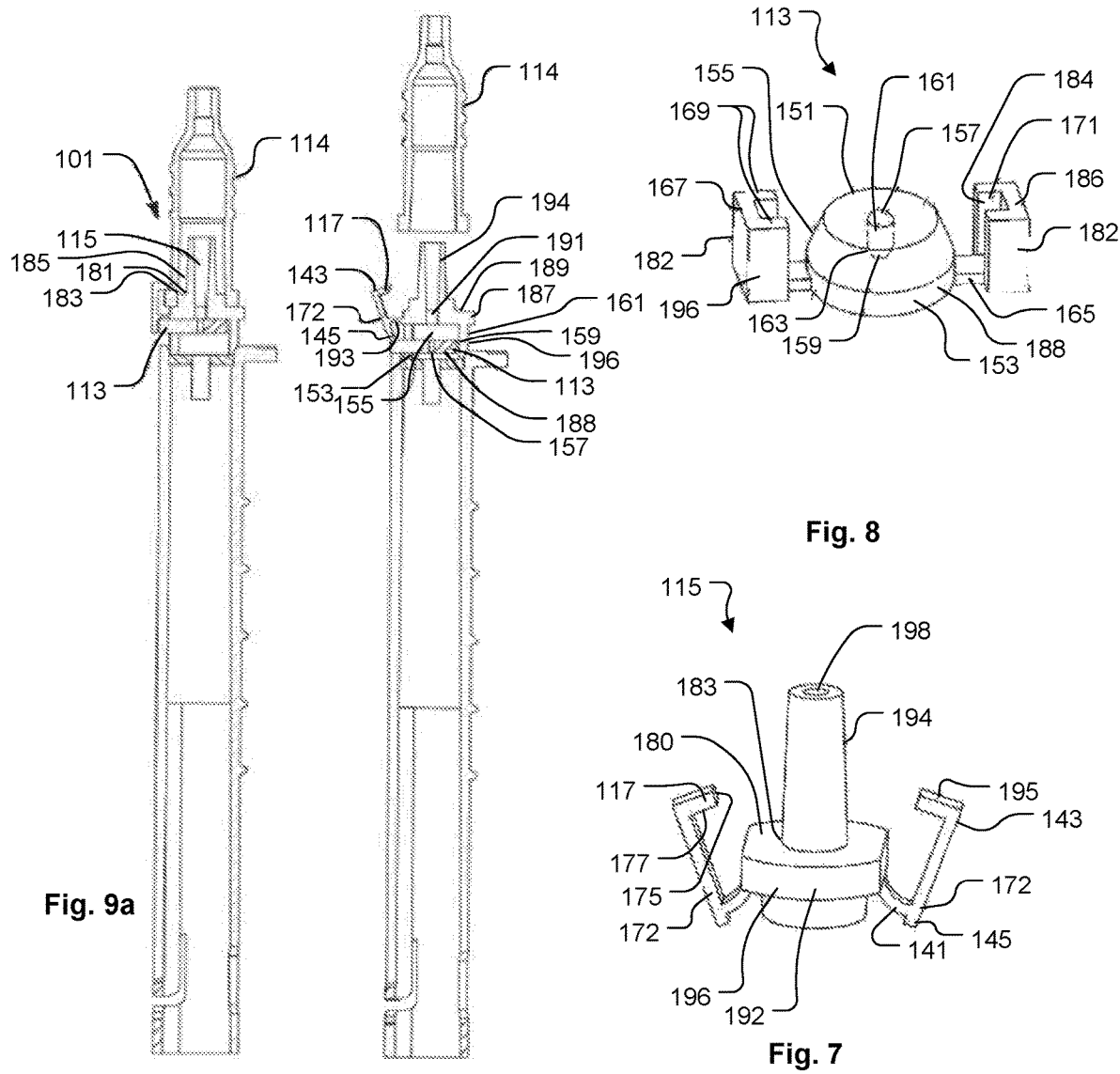

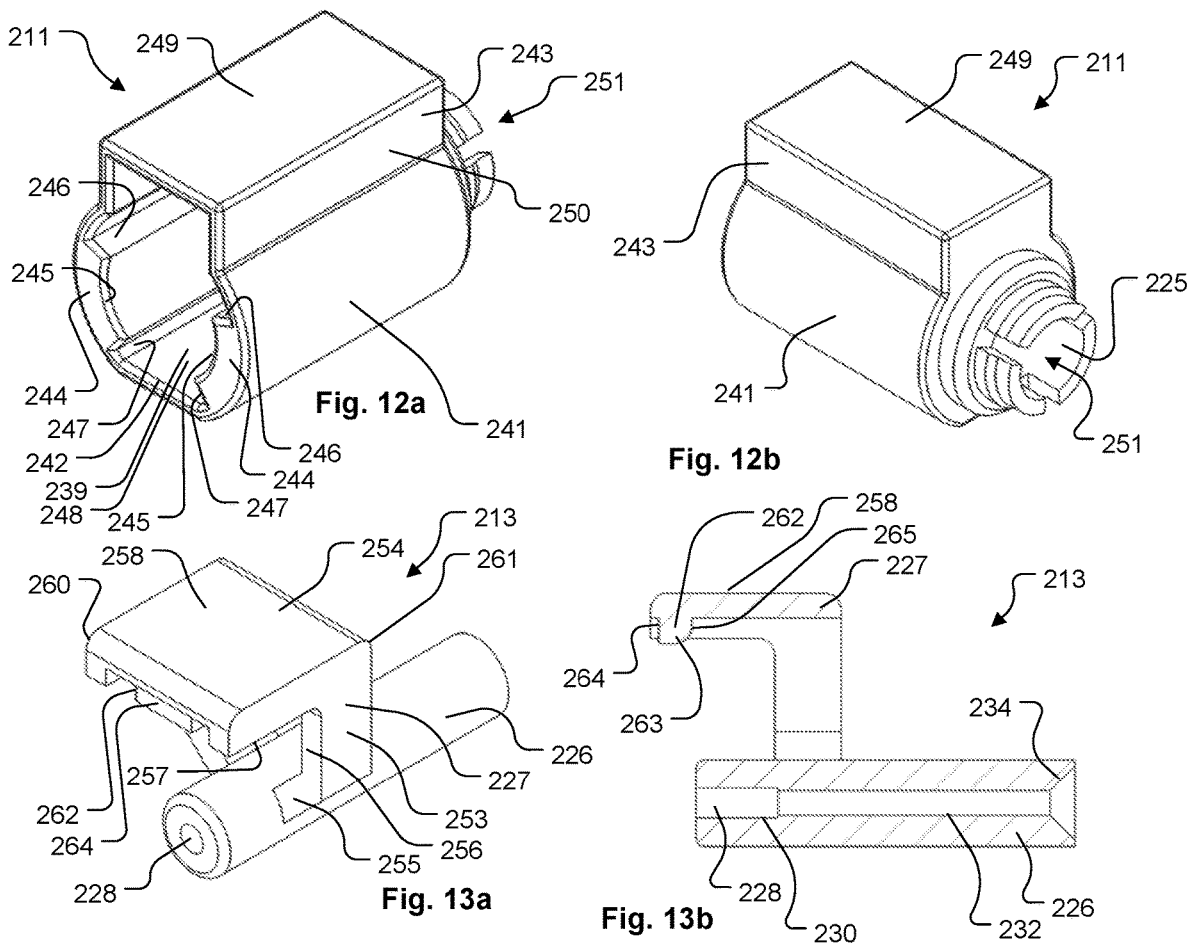
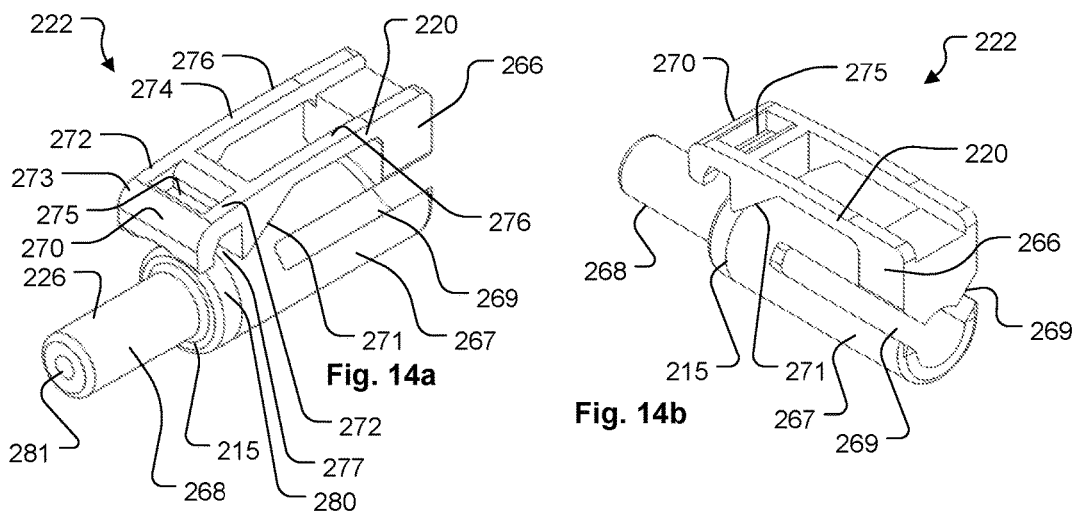

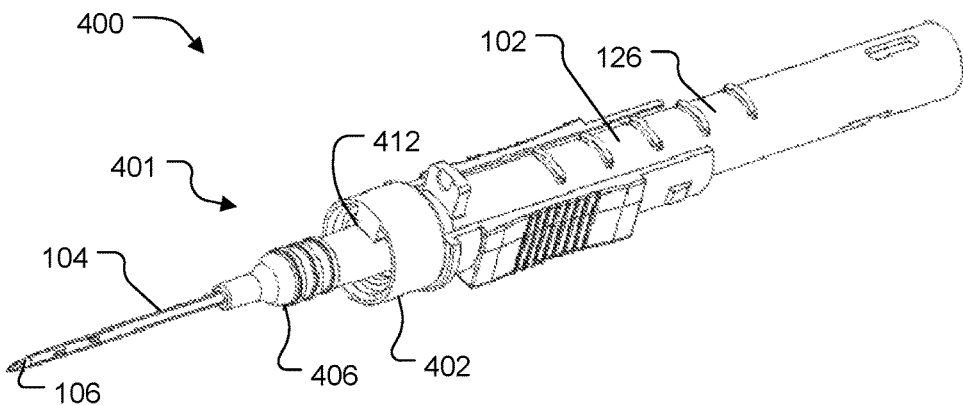
Fig. 19
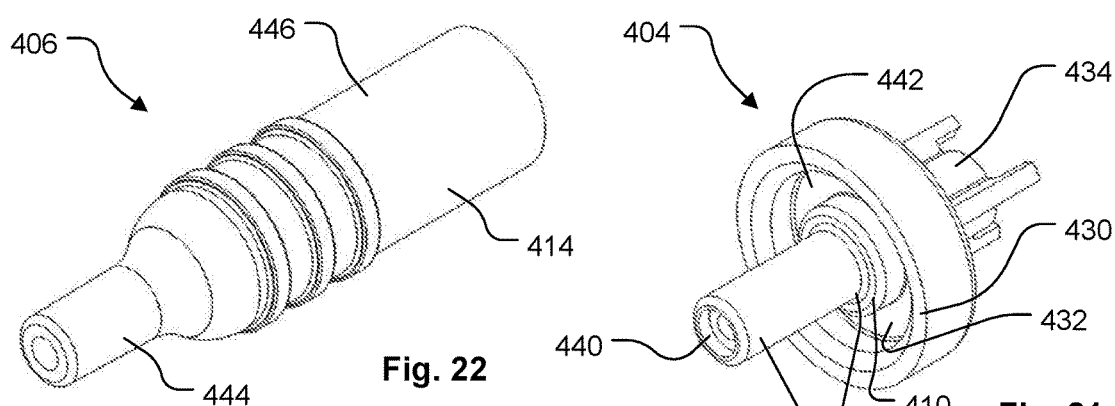
Fig. 22
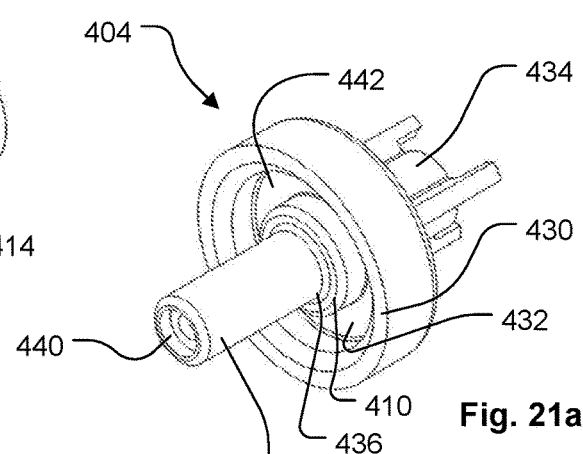
Fig. 21a
Fig. 21b
Fig. 20

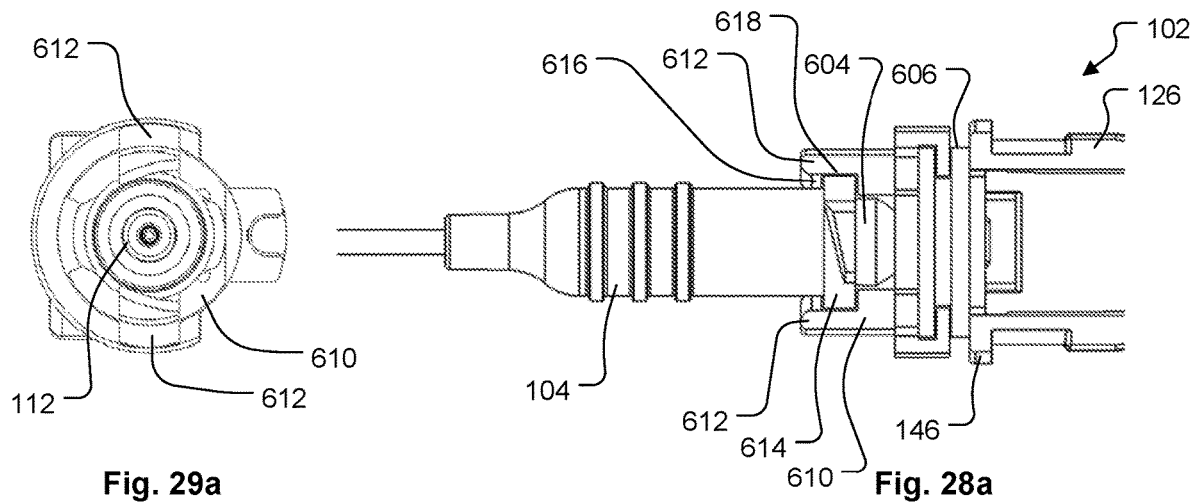
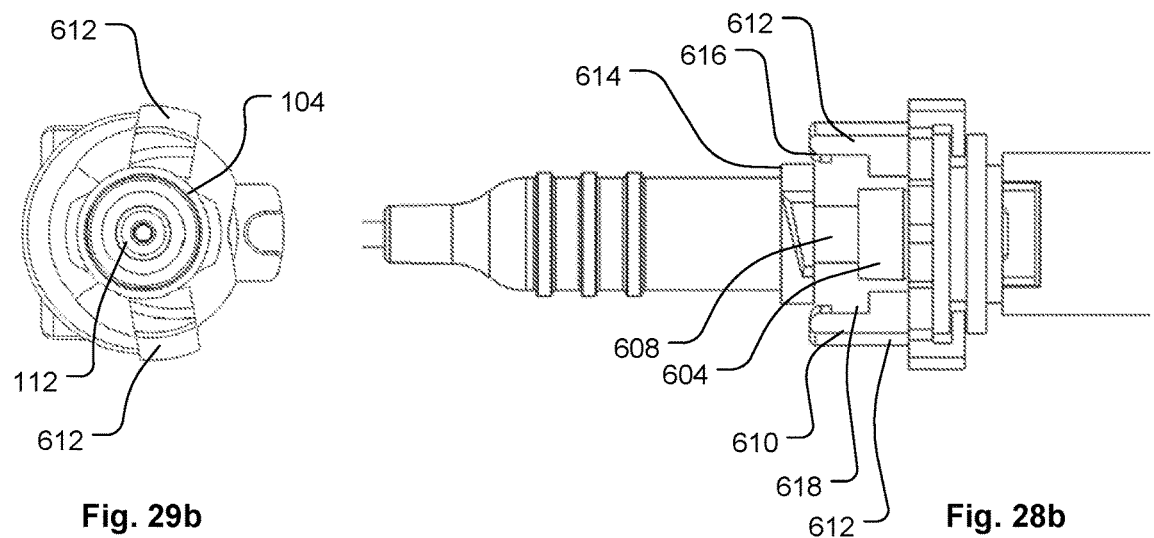

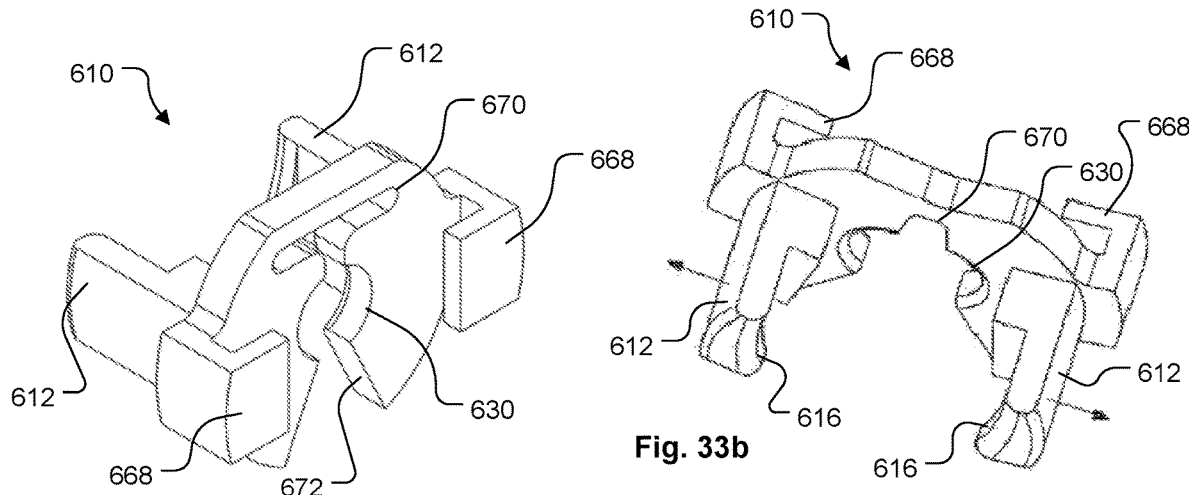
Fig. 33a
Fig. 33b
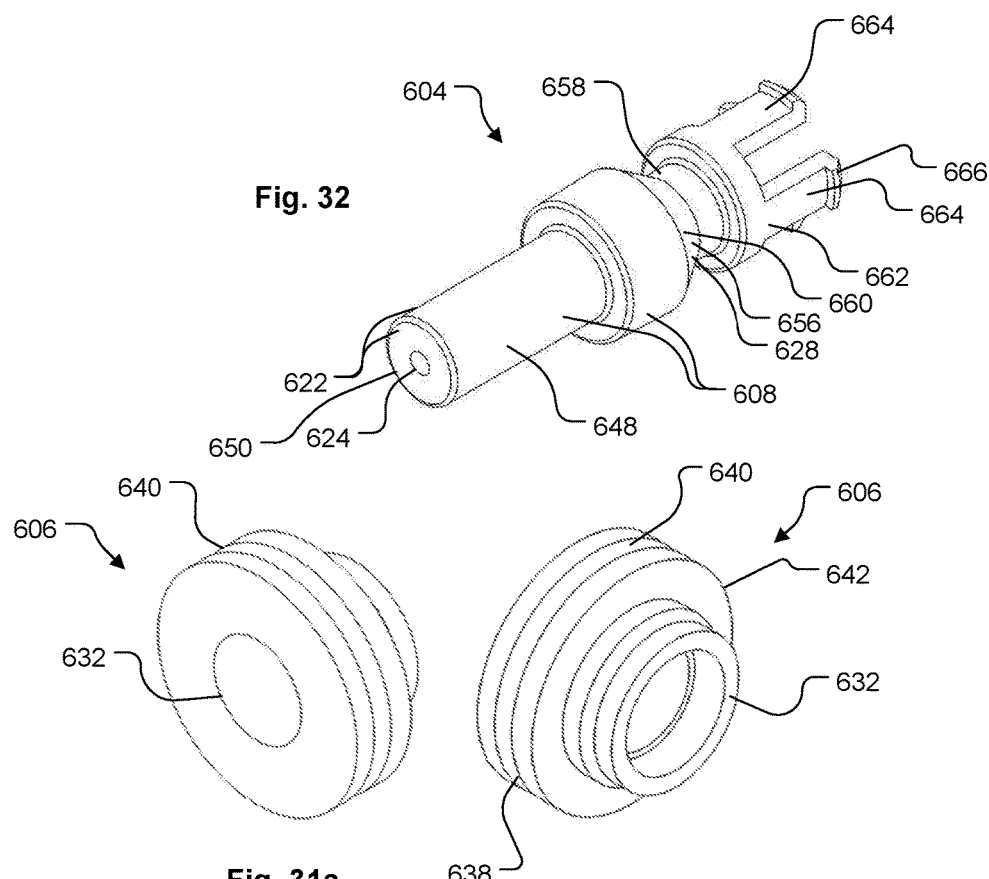
Fig. 32
Fig. 31a
Fig. 31b

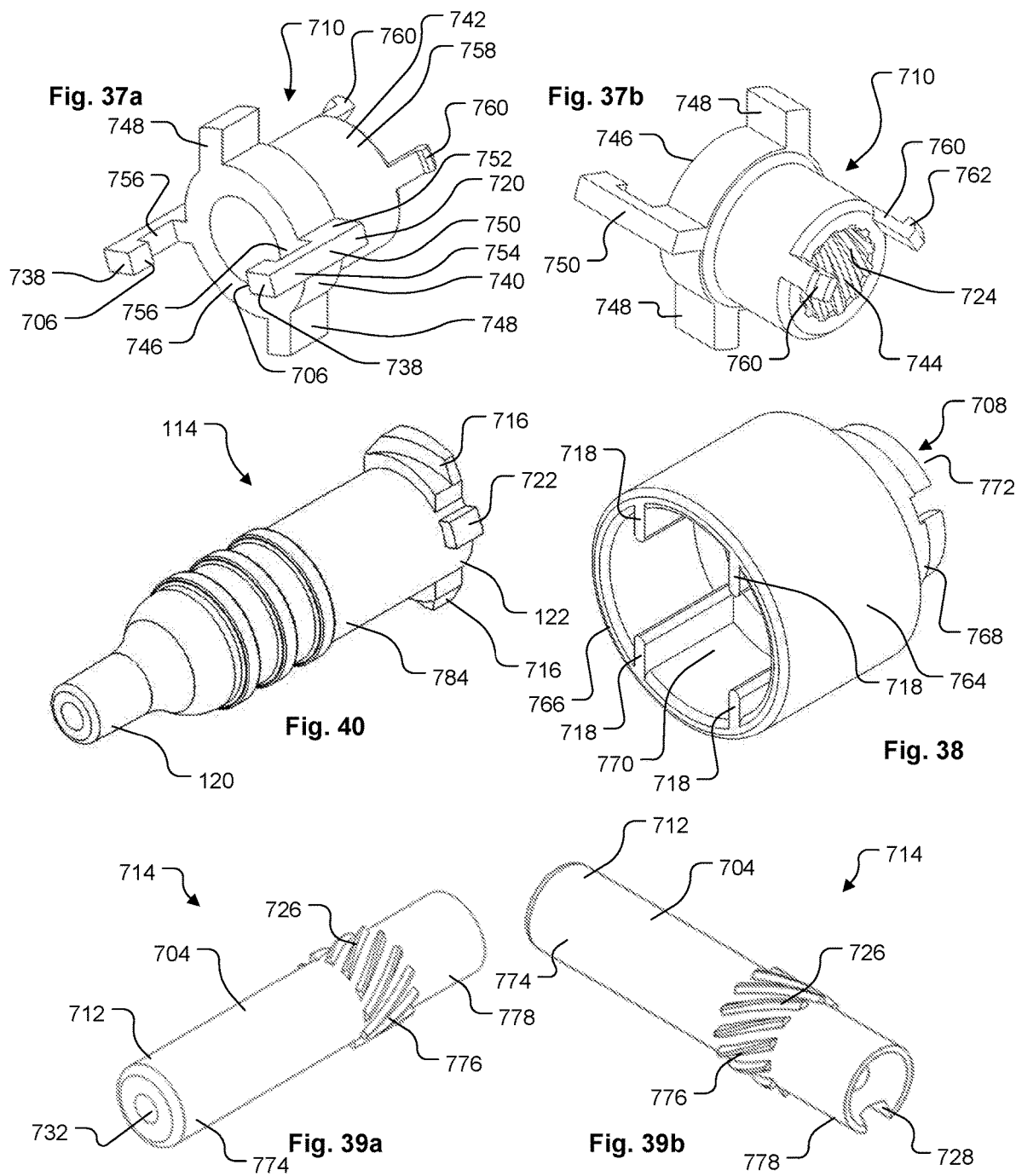

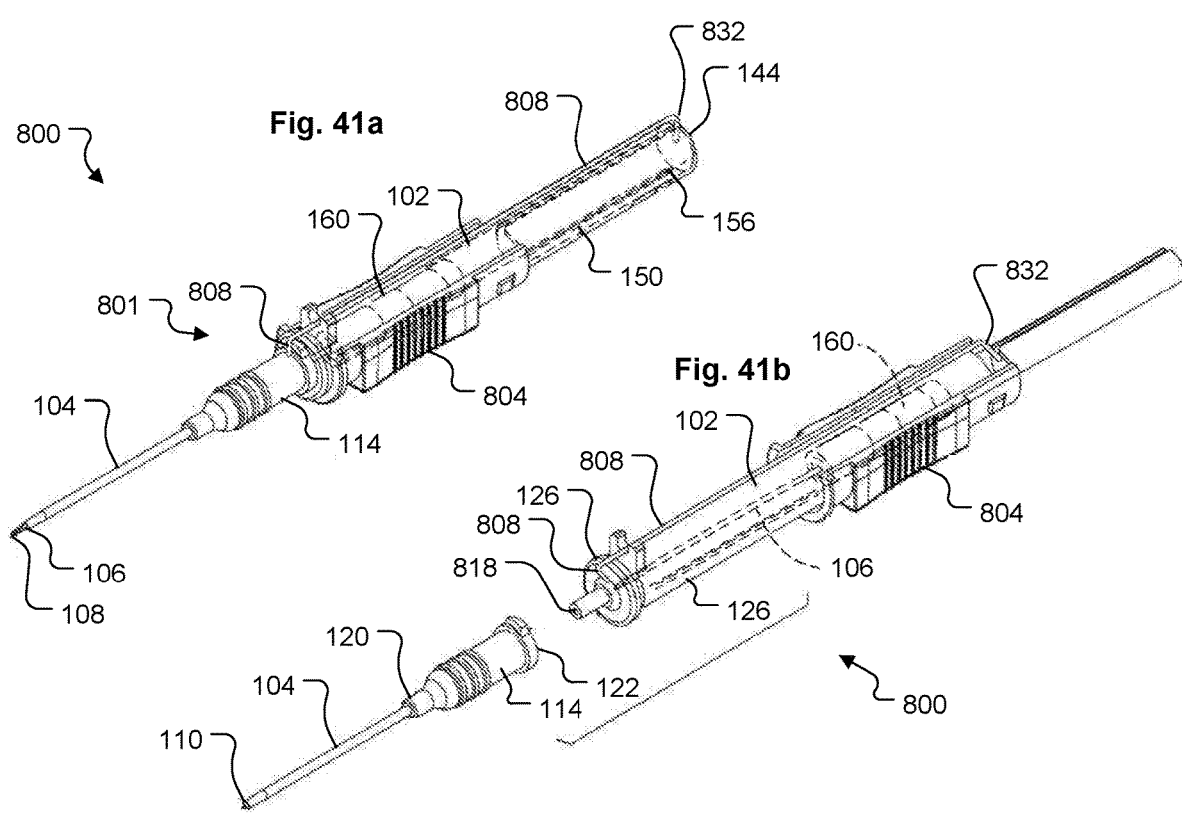

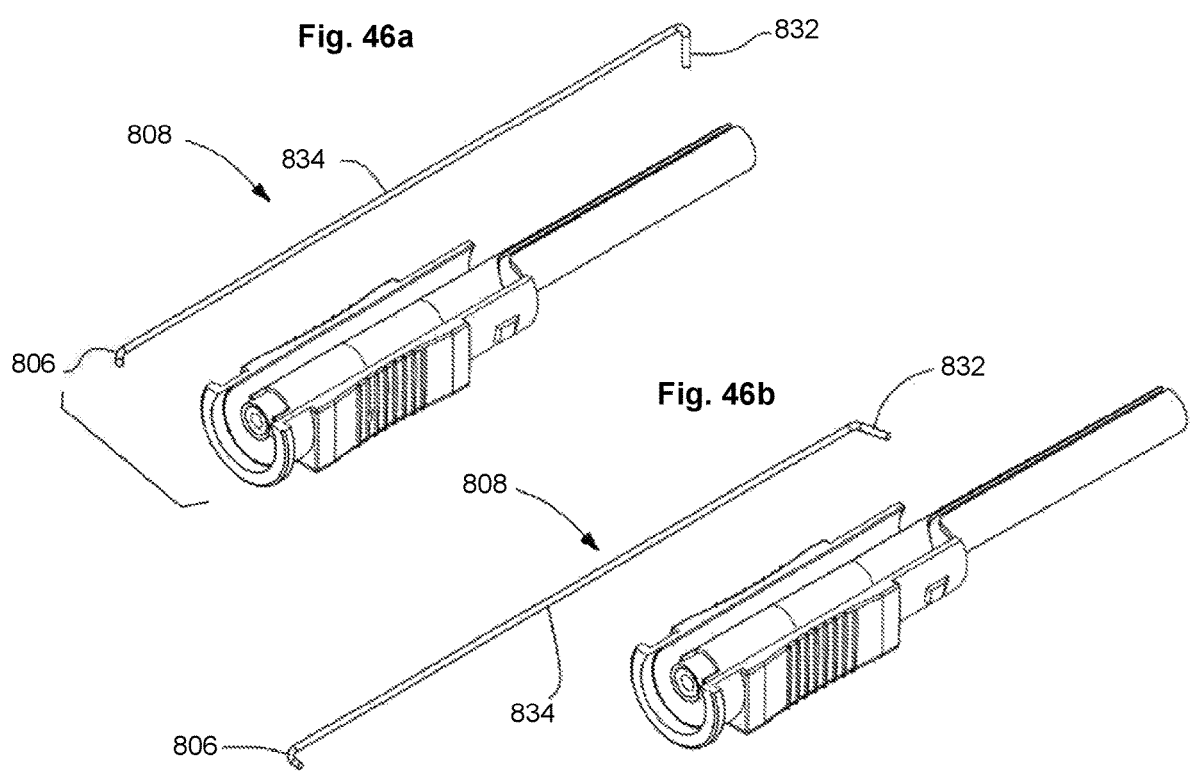

RELEASEABLE CATHETER HUB RETAINER

RELATED APPLICATIONS

This application is a continuation of U.S. application Ser. No. 15/012,013 filed Feb. 1, 2016, which claims the benefit of U.S. Provisional Application Nos. 62/109,673; 62/109,710; 62/109,715; 62/109,722; 62/109,735; 62/109,742; 62/109,745; 62/109,750; 62/109,755; 62/109,759; 62/109,766, all of which were filed Jan. 30, 2015 and are hereby incorporated herein by reference.

TECHNICAL FIELD

The present disclosure relates generally to intravenous catheters that are inserted over a needle, and more particularly to a safety catheter insertion device having a releasable coupling between the catheter insertion device and a catheter hub.

BACKGROUND

Intravenous (IV) therapy is a versatile technique used for the administration of medical fluids to and withdrawal of bodily fluids from patients. IV therapy has been used for various purposes such as the maintenance of fluid and electrolyte balance, the transfusion of blood, the administration of nutritional supplements, chemotherapy, and the administration of drugs and medications. Fluids can be administered intravenously by injection through a hypodermic needle, or intermittently or continuously by infusion using a needle or catheter. The most common intravenous access method utilized by clinicians is the peripheral IV catheter.

A peripheral IV catheter is made of soft, flexible plastic or silicone rubber, generally between fourteen to twenty-four gauge in size. In the conventional venipuncture procedure, a catheter is inserted into a vein in the patient's hand, foot, or the inner aspect of the arm or any vein in the body that will accept an IV catheter. Typical peripheral IV catheters are "over-the needle" catheters where the catheter is coaxially placed over an introducer needle. In order to properly place the catheter into a patient's vein, the sharpened tip of the introducer needle, is used to puncture the skin, tissue, and vein wall to provide a path for placement of the catheter.

Placement of a peripheral IV catheter generally includes preparation of the biological site of the patient. Often a tourniquet is applied proximal to the biological site and a variety of techniques can be used to dilate the patient's vein. While wearing disposable gloves, the clinician cleanses the biological site and a vein is retracted or anchored by placing a thumb over the vein about fifty to seventy-five mm distal to the site. The needle and catheter are introduced into the vein by inserting the bevel of the sharpened tip into the vein at about a twenty to thirty degree angle with the bevel facing up in order to pierce one wall of the vein. The catheter thus rides with the needle through the skin, tissue, and vein wall and into the patient's vein.

Various catheter insertion devices have been developed to provide a needle for catheterization. One such example of this type catheter insertion device is marketed by Smiths Medical ASD, Inc. of St. Paul, MN, under the TELCO trademark, as described in U.S. Pat. Nos. 7,291,130 and 8,257,322 (depicting an IV catheter insertion device marketed by Smiths Medical ASD, Inc. under the INTUITIV Safety IV Catheters trademark), both of which are incorporated by reference herein. In other cases, the catheter insertion device provides a safety needle assembly that functions to house the sharpened tip of the needle to reduce the likelihood of an inadvertent needle stick. Examples of this type of catheter insertion device are described in U.S. Pat. No. 5,000,740 (depicting an IV catheter insertion device marketed by Smiths Medical ASD, Inc. under the PROTECTIV trademark), U.S. Pat. No. 7,736,342 (depicting an IV catheter insertion device marketed by Smiths Medical ASD, Inc. under the VIAVALVE trademark), both of which are incorporated by reference herein.

To finish placement, the needle and catheter are lowered towards the skin to decrease the entry angle, and the catheter is advanced slightly into the vein. The connection between the catheter and needle is then loosened, so that the catheter can be advanced further into the vein as desired, and the needle can be withdrawn from the catheter. Infusion tubing, which can be connected to the catheter, can then be secured to the insertion site by gauze and adhesive tape.

Catheter insertion devices which attempt to lock the catheter to the catheter insertion device during insertion have been created. However, such devices do not consistently enable a smooth release of the catheter from the needle, particularly in a way that reduces or eliminates the risk of an inadvertent needle stick. Accordingly, the applicants have identified a need for a safety catheter insertion assembly that includes a means for smoothly and passively releasing the catheter from the catheter insertion device upon retraction of the needle to a safe position.

SUMMARY OF THE DISCLOSURE

Embodiments of the present disclosure meet the need for a safety catheter insertion assembly that includes a means for smoothly and passively releasing a catheter from a catheter insertion device upon retraction of the needle to a safe position, thereby inhibiting the risk of an inadvertent needle stick, while improving the catheter insertion process.

One embodiment of the present disclosure provides a safety catheter insertion assembly including a catheter tube, catheter hub, needle housing, insertion needle, and needle hub. The catheter tube has a distal end for insertion into a biological site, a proximal end and a wall defining a Lumen extending therebetween. The catheter hub is operably coupled to the proximal end of the catheter. The insertion needle has a sharpened distal tip and a proximal end. The needle hub is fixedly coupled to the proximal end of the insertion needle, and slideably coupled to the needle housing such that the needle hub is moveable between a first position, wherein the insertion needle extends from the needle housing and is positioned coaxially within the lumen of the catheter, and a second position, wherein the catheter is separated from the insertion needle and the sharpened distal tip is housed within the needle housing. The needle housing includes a catheter hub coupling means for coupling the catheter hub to the needle housing in the first position and for releasing the catheter hub from the needle housing in the second position, and a needle hub interlock means for interlocking the needle hub to the needle housing in the second position.

In some versions, the catheter hub coupling means grips an exterior surface of the catheter hub. In some versions, the catheter hub includes a luer lock lug structure positioned on the exterior surface of the catheter hub, where the catheter hub coupling means grips the luer lock lug structure. In some versions, the catheter hub includes a wall defining an interior cavity, and a portion of the needle housing is inserted within the interior cavity and configured to provide supporting contact with the catheter hub interior cavity wall when the needle housing is in the first position. In some versions, the catheter hub coupling means releases the catheter hub prior to the interlocking of the needle hub to the needle housing. In some versions, release of the catheter hub by the catheter hub coupling means is affected by sliding the insertion needle and the needle hub relative to the needle housing. In some versions, the needle hub has a "C" shaped cross section conformed to fit around an outer surface of the needle housing in a manner that inhibits the needle hub from readily separating from the needle housing, yet enables the needle hub and needle housing to slide relative to one another between the first position and the second position with minimal resistance. In some versions, the needle housing includes a wall defining a groove, and the needle hub includes a protuberance configured to slidably fit within the groove thereby inhibiting the needle hub from rotating about a longitudinal axis of the needle housing. In some versions, the wall defining the groove, further defines a bottleneck in the groove that is generally narrower in width than the rest of the groove. In some versions, the protuberance of the needle hub has a wedge shape, wherein the apex of the wedge faces towards the bottleneck in the first position and away from the bottleneck in the second position, thereby interlocking the needle hub to the needle housing in the second position. In some versions, in the first position the sharpened distal tip protrudes slightly beyond the distal end of catheter. In some versions, in the second position the sharpened distal tip is interlocked in a safe position to reduce the risk of an inadvertent needle stick. In some versions, the needle hub includes a flash chamber. In some versions, the flashback chamber is constructed of at least one of a transparent and translucent material configured to enable a clinician to see when fluid enters the flash chamber. In some versions, the flashback chamber includes a microporous flashplug configured to enable air to vent as fluid enters the flash chamber.

Another embodiment of the present disclosure provides a safety catheter insertion device for use with a catheter having a catheter tube and a catheter hub. The safety catheter insertion device includes a needle assembly, a needle housing, a nose, an actuator, and one or more exterior hub contacts. The needle housing has a needle lock. The nose is connected to the needle housing and is constructed and arranged for positioning at least partially interior to the catheter hub. The one or more exterior hub contacts are constructed and arranged to contact an exterior of the catheter hub. The needle assembly has a needle hub and a needle. The needle has a needle tip and a needle transition positioned proximal to the needle tip. The actuator is positioned about the needle and constructed and arranged to move proximally when urged by the needle transition as the needle is moved proximally during needle withdrawal. The needle assembly is operably connected to the needle housing and movable between a ready for use position and a safe position. In the ready for use position, the catheter is assembled to the catheter insertion device with the catheter tube carried over the needle. Removal of the catheter from the catheter insertion device is inhibited at least by engagement of the exterior hub contact to the catheter hub. In the safe position, the needle tip is positioned interior to the nose to inhibit access to the needle tip, and the needle lock of the needle housing is engaged to the needle assembly at a position proximal to the needle tip, to inhibit distal movement of the needle tip from the nose. Proximal movement of the needle assembly during needle withdrawal causes the transition to shift the actuator proximally to release the catheter hub from engagement by the one or more exterior hub contacts after the needle lock engages the needle assembly.

In some versions, the needle includes a protuberance and the needle lock includes a pair of engagement tabs that interact with a protrusion to inhibit distal movement of the needle tip from the nose after the needle assembly is in the safe position. In some versions, the needle lock is positioned proximal to the needle transition when the needle assembly is in the safe position. In some versions, the needle lock is positioned proximal to a proximal end of the needle, when the needle assembly is in the safe position. In some versions, the actuator defines a lumen that extends from a distal end of the actuator to a proximal end of the actuator and that includes a needle abutment contacted by the needle transition to shift the actuator proximally to release the catheter hub from engagement by the exterior hub contact after the needle lock engages the needle assembly. In some versions, the nose includes a nose lumen that slidably receives the needle and that, in the safe position, is unblocked between the distal end of the nose and the needle tip when the needle assembly is in the safe position. In some versions, the needle housing includes an elongate body, wherein at least portions of the needle that lie between the needle hub and the transition are positioned interior to the elongate body when the needle assembly is in the safe position.

In some versions, the safety catheter insertion device further includes an engagement arm that includes the one or more external hub contacts. In some versions, the actuator includes one or more actuator arms that retain the external hub contacts in engagement with the catheter hub by engaging a corresponding engagement arm when the needle assembly is in the ready for use position. In some versions, the safety catheter insertion device further includes a collar connected to the needle housing and positioned at least partially about the nose and the catheter hub when the needle assembly is in the ready for use position. In some versions, the exterior hub contact includes a first contact and a second contact, the first contact positioned distally to the second contact. In some versions, the engagement arm includes a pair of engagement arms and the engagement arms include a pair of actuator arms, each of the pair of engagement arms and actuator arms being positioned on opposing sides of the catheter hub when the needle assembly is in the ready for use position. In some versions, a proximal end of the catheter hub includes a radial rib, the engagement arms being positioned distally of the radial rib to inhibit removal of the catheter from the catheter insertion device. In some versions, the nose includes one or more interior hub contacts that cooperate with the one or more external hub contacts to inhibit removal of the catheter prior to the needle assembly being in the safe position. In some versions, the nose and actuator are separate components, the nose remaining stationary with respect to the needle housing as the actuator moves proximally with the needle assembly. In some versions, at least a portion of the actuator is slidable internally to the nose.

In some versions, the safety catheter insertion device further includes a collar connected to the needle housing and positioned at least partially about the nose and the catheter hub when the needle assembly is in the ready for use position.

In some versions, the safety catheter insertion device further includes a retainer that includes a first set of the one or more exterior hub contacts, the retainer being a unitary structure that includes the nose and the actuator. In some versions, the collar includes a second set of the one or more exterior hub contacts. In some versions, the nose of the retainer includes one or more interior hub contacts that cooperate with the first and second set of exterior hub contacts to inhibit removal of the catheter hub prior to the needle assembly being in the safe position. In some versions, shifting the actuator proximally to release the catheter hub includes shifting the retainer proximally to release the catheter hub from cooperative engagement by the interior hub contacts and the first and second set of exterior hub contacts. In some versions, shifting the retainer proximally includes shifting the one or more interior hub contacts and the first set of exterior hub contacts proximally without shifting the first set of exterior hub contacts. In some versions, the collar includes a tab that inhibits the retainer from shifting proximally prior to the actuator being urged by the needle transition as the needle is moved proximally during needle withdrawal.

In some versions, the safety catheter insertion device further includes an engagement structure including opposed portions, the one or more external hub contacts being positioned on the opposed portions. In some versions, the engagement structure has a "C" shaped construction. In some versions, the opposed portions of the engagement structure are biased toward one another to engage the catheter hub in the ready for use position. In some versions, the nose includes one or more interior hub contacts that cooperate with the one or more external hub contacts to inhibit removal of the catheter prior to the needle assembly being in the safe position. In some versions, the nose and the actuator are formed as a common unitary component that is shifted proximally to release the catheter from engagement. In some versions, the actuator includes a ramp that urges the opposed portions of the engagement structure apart from one another as the actuator is shifted proximally. In some versions, the one or more exterior hub contact surfaces are formed in grooves on the opposed portions of the engagement structure. In some versions, a proximal end of the catheter hub includes a radial rib, the grooves being constructed and arranged to contact the rib of the catheter hub.

In some versions, the safety catheter insertion device further includes an engagement structure that includes the one or more exterior hub contacts and that is constructed and arranged to rotate about an axis coincident with the needle as the actuator shifts proximally to release the catheter hub from engagement. In some versions, the actuator and the engagement structure include complimentary helical surfaces, proximal shifting of the actuator causing the engagement structure to rotate through interaction of the complimentary engaging helical surfaces. In some versions, the engagement structure includes engagement arms that provide exterior hub contacts to engage a rib on the catheter hub, the engagement arms and exterior hub contacts rotating as the actuator shifts proximally to release the catheter hub from engagement.

In some versions, the safety catheter insertion device further includes a collar connected to the needle housing and positioned at least partially about the nose and the catheter hub when the needle assembly is in the ready for use position. In some versions, the nose includes one or more interior hub contacts that cooperate with the one or more external hub contacts to inhibit removal of the catheter prior to the needle assembly being in the safe position. In some versions, the nose and the actuator are formed as a common unitary component.

In some versions, the safety catheter insertion device further includes a catheter. In some versions, the catheter includes a blood control valve positioned internally to the catheter hub, the nose contacting the blood control valve when the catheter is assembled to the catheter housing to contain flashback blood. In some versions, the blood control valve is constructed and arranged to be actuated by insertion of a mating connector into the catheter hub. In some versions, the needle includes a notch that permits blood to flow to an annular space between the needle and the catheter tube with the needle assembly in the ready for use position. In some versions, the catheter hub includes wings.

Another embodiment of the present disclosure provides a safety catheter insertion device for use with a catheter having a catheter tube and a catheter hub. The safety catheter insertion device includes a needle assembly, a needle housing, a nose, an actuator, and an engagement structure. The nose is connected to the needle housing and constructed and arranged for positioning at least partially interior to a catheter hub. The engagement structure includes one or more exterior hub contacts and is arranged to contact an exterior of the catheter hub. The needle assembly has a needle hub and a needle. The needle has a needle tip and a needle transition positioned proximal to the needle tip. The actuator is positioned about the needle and constructed and arranged to move proximally when urged by the needle transition as the needle is moved proximally during needle withdrawal. The needle assembly is operably connected to the needle housing and movable between a ready for use position and a safe position. In the ready for use position, the catheter is assembled to the catheter insertion device with the catheter tube carried over the needle. Removal of the catheter from the catheter insertion device is inhibited at least by engagement of the exterior hub contact to the catheter hub. In the safe position, the needle tip is positioned interior to the nose to inhibit access to the needle tip. Proximal movement of the needle assembly during needle withdrawal causes the transition to shift the actuator proximally to rotate the actuator about an axis coincident with the needle to release the catheter hub from engagement by the one or more exterior hub contacts after the needle lock engages the needle assembly.

Another embodiment of the present disclosure provides a safety catheter assembly safety coupling, including a nose and an actuator. The nose includes a tapered extension extending distally that is sized and shaped to be received within a catheter hub. The nose also includes at least one engagement arm extending from the nose that is engageable to an exterior of the catheter hub to secure the catheter hub to the nose, and being shiftable between an engaged position wherein the at least one engagement arm is engaged to the catheter hub and the catheter hub is inhibited from separation, and a disengaged position wherein the at least one engagement arm is separated from the catheter hub and the catheter hub can be removed from the nose. The at least one engagement arm having a distal portion that engages the catheter hub and a proximal portion that engages the actuator, and being operably coupled to the tapered extension by a resilient member. At least a portion of the actuator being located proximal to the nose and being abuttable to an interior of the proximal portion of the at least one engagement arm and the actuator being shiftable between a distal position, wherein the actuator holds the at least one engagement arm in a first, engaged position by inhibiting inward movement of the proximal portion of the at least one engagement arm and a proximal position, wherein the proximal portion of the at least one engagement arm can move inwardly and the distal portion of the at least one engagement arm is released from the catheter hub and the catheter hub can be removed from the nose.

In some versions, the nose further includes a body portion and a mounting plate portion, wherein the mounting plate portion is fixably couplable to a distal end of a needle housing of the safety catheter assembly. In some versions, the at least one engagement arm further includes two hub diametrically opposed retention fingers. In some versions, the actuator defines a needle passage therethrough wherein the needle passes through the needle passage and includes a needle transition that engages a portion of the passage such that when the needle is withdrawn proximally the actuator is engaged and moved proximally with the needle and the actuator is shifted to the proximal position and the at least one engagement arm is disengaged from the catheter hub. In some versions, the actuator further includes an actuator arm including a radial portion and an arm box portion. In some versions, the arm box portion further includes an exterior wall and side walls defining a distal portion receiver into which the distal portion of the at least one engagement arm is receivable. In some versions, the radial portion of the actuator arm is captured by a slot formed in a needle housing of the safety catheter assembly.

Another embodiment of the present disclosure provides a safety catheter assembly having a safety coupling including a collar, an actuator, a nose, a catheter hub, and a needle. The collar is engageable to the catheter hub. The actuator is located within the collar, and is axially shiftable between a distal position and a proximal position. The nose is located within the collar and partially surrounds a portion of the actuator. The nose has an engagement arm that is shiftable between a catheter hub engaged position, wherein the catheter hub is inhibited from removal from the collar, and a catheter hub disengaged position, wherein the catheter hub is removable from the collar. The engagement arm is resiliently biased toward the catheter hub disengaged position. The engagement arm is shifted to the catheter hub engaged position when the actuator is in the distal position, and is resiliently shifted to the catheter hub disengaged position when the actuator is in the proximal position. The catheter hub is engageable at least partially within the collar and at least partially over the nose. The catheter hub is axially removable from the collar when the engagement arm is in the catheter hub disengaged position. The engagement arm includes a finger portion and a thumb portion that together define a hand gap. The hand gap closely conforms to the catheter hub, such that when the catheter hub is engaged in the hand gap the catheter hub is inhibited from removal. The needle has a needle transition that engages the actuator when the needle is being withdrawn proximally and thereby moves the actuator toward the proximal position.

In some versions, the collar further includes a cupola portion and a cylindrical portion. In some versions, the actuator further includes an actuator needle passage and an external portion. In some versions, the actuator needle passage has a wide portion and a narrow portion, the wide portion being located distally from the narrow portion. In some versions, the external portion presents an arch structure having a roof portion having an inwardly facing nose engaging portion structured to urge the engagement arm inwardly. In some versions, the collar further includes nose bushings internally that are dimensioned to receive and support the nose therein. In some versions, the nose further includes a distal nose and a cylindrical body. In some versions, the cylindrical body is integrally coupled to the nose engaging portion. In some versions, the cylindrical body includes a larger portion and a smaller portion, the larger portion and the smaller portion together defining two radial support receiving slots therebetween. In some versions, the cupola portion is sized and structured to closely conform to a roof portion of the actuator, the roof portion having an inwardly facing nose engaging portion configured to urge the engagement arm inwardly when the actuator is in the distal position.

Another embodiment of the present disclosure provides a safety catheter assembly including a retainer and a collar. The retainer is received within the collar, and includes an actuator and a nose, such that the actuator and the nose form a unitary structure. The retainer and the collar are shaped and sized such that a catheter hub is receivable at least partially within the collar and at least partially over the nose of the retainer. The actuator is shiftable between a distal, engaged ready for use position and a proximal, disengaged safe position. The collar receives a proximal end of the catheter hub therein. The nose engages to an interior of the catheter hub in the distal, engaged ready for use position. The catheter hub is releasable from the collar and the retainer when the actuator is in the proximal, disengaged safe position.

In some versions, the safety catheter assembly includes a needle assembly. In some versions, the safety catheter assembly includes a needle housing, wherein the collar is fixedly coupled to the needle housing. In some versions, the needle housing includes the needle lock configured to interlock the needle assembly to the needle housing in the proximal, disengaged safe position. In some versions, when the actuator is in the distal, engaged ready for use position, a longitudinal axis of the needle assembly and a longitudinal axis of the catheter hub are substantially coaxial or parallel. In some versions, when the actuator is in the proximal, disengaged safe position, the catheter hub is disengageable from the retainer and the collar by angular rotation of the longitudinal axis of the catheter hub to a position such that the longitudinal axis of the catheter hub is no longer substantially coaxial or parallel with the longitudinal axis of the needle assembly. In some versions, the nose includes interior hub contacts that engage to the interior of the catheter hub when the actuator is in the distal, engaged ready for use position. In some versions, the nose engages to the interior of the catheter hub in the distal, engaged ready for use position, such that a distal end of the nose is proximate to a distal end of an interior space of the catheter hub, thereby inhibiting separation of the catheter hub from the collar and the retainer. In some versions, the nose extends distally from the actuator and is structured to sheath the needle tip when the needle tip is retracted to the second, safe position. In some versions, when the nose is in the distal, engaged ready for use position, the length of the nose that extends within the interior of the catheter hub is at least twice a diameter of the nose. In some versions, the interior of the catheter hub is resilient to facilitate disengagement of the catheter hub from the nose. In some versions, the retainer includes exterior hub contacts configured as an arcuate partial wall that engages the proximal end of the catheter hub when the actuator is in the distal, engaged ready for use position, thereby inhibiting separation of the catheter hub from the collar and the retainer. In some versions, the arcuate partial wall further defines a hub flange space into which a flange of the catheter hub is receivable. In some versions, the collar and the retainer are configured to engage opposing surfaces of the proximal end of the catheter hub. In some versions, the collar further includes a step feature that engages the proximal end of the catheter hub. In some versions, the safety catheter assembly further includes structure that engages the retainer with the collar in a rotationally fixed manner while enabling axial movement. In some versions, the retainer further includes one or more proximal extensions and the collar further includes a proximal wall portion defining one or more proximal gaps therein. In some versions, the safety catheter assembly further includes a needle that passes through a needle passage defined through the actuator, wherein the needle has a needle transition proximate to a needle tip. In some versions, the needle passage has a wider portion and a narrower portion sized such that the needle transition is free to pass through the wider portion but not through the narrower portion, whereby the needle transition engages the actuator to retract with the needle.

Another embodiment of the present disclosure provides a safety catheter assembly including a catheter and a safety catheter insertion device. The catheter has a catheter hub and a catheter tube. The safety catheter insertion device is selectively connectable to the catheter hub and includes a needle housing, needle assembly, collar, engagement structure, and actuator. The needle housing has a generally cylindrical elongate body. The needle assembly includes a needle and a needle hub, slideably coupled to the needle housing. The collar is located proximate to a distal end of the needle housing. The engagement structure is coupled to the collar, and includes at least one engagement arm that selectively engages the catheter hub. The actuator is received by the collar and the catheter hub, and includes a wedge portion that is shiftable between a first, ready for use position in which the at least one engagement arm engages the catheter hub, and a second, safe position in which the wedge portion forces the engagement structure open such that the at least one engagement arm disengages the catheter hub.

In some versions, the wedge portion is frustoconical. In some versions, the engagement structure is a C-shaped clamp. In some versions, the actuator is shiftable between the first, ready for use position and the second, safe position in response to proximal movement of the needle. In some versions, the catheter hub is receivable at least partially within the engagement structure and partially over the actuator in the first, ready for use position. In some versions, the catheter hub is releasable from the collar, the actuator, and the engagement structure when the engagement structure is in the second, safe position. In some versions, the needle housing includes a needle lock configured to inhibit movement of the needle assembly from the second, safe position. In some versions, the needle lock includes a bottleneck on the needle housing that engages with a triangular protuberance on the needle assembly when in the second, safe position. In some versions, the actuator includes a nose receivable in the catheter hub in the first, ready for use position. In some versions, the engagement structure is biased to the first, ready for use position in which the at least one engagement arm is engaged and shiftable to the second, safe position in which the at least one engagement arm is expanded and disengaged when the wedge portion shifts relative to the engagement structure. In some versions, the engagement structure includes two engagement arms that selectively engage the catheter hub.

Another embodiment of the present disclosure provides a safety catheter assembly including a catheter and a safety catheter insertion device. The catheter includes a catheter hub and a catheter tube. The safety catheter insertion device is selectively connectable to the catheter hub, and includes a needle housing, a needle assembly, a collar, engagement structure, and actuator. The needle housing has a generally cylindrical elongate body. The needle assembly includes a needle and a needle hub, slideably coupled to the needle housing. The collar is coupled to a distal end of the needle housing and is engageable within the catheter hub. The engagement structure is located within the collar, and includes engagement arms, and is axially rotatable relative to the collar between a first, engaged position, wherein the engagement arms are engaged to the catheter hub, and a second, disengaged position wherein the catheter hub is removable from the engagement structure and the collar. The actuator is located at least partially within the engagement structure, and is axially shiftable relative to the engagement structure and engaged to the engagement structure by a plurality of helical features, whereby the engagement structure is rotationally shifted as the actuator is axially shifted.

In some versions, the needle includes a needle transition which engages with the actuator to move the actuator axially along with the needle as the needle is withdrawn, thereby rotating the engagement structure to the second, disengaged position. In some versions, the plurality of helical features includes raised helical ridges on the actuator. In some versions, the actuator includes a nose. In some versions, the catheter hub includes a plurality of lugs and at least one finger radially extending outwardly therefrom. In some versions, the actuator includes a needle passage with a wider portion and narrower portion sized to receive a needle with a needle transition. In some versions, the collar includes a plurality of vertical ribs and a column. In some versions, the engagement structure includes a collar engaging portion and an actuator engaging portion. In some versions, the engagement structure includes snap features including hooks.

Another embodiment of the present disclosure provides a safety catheter assembly including a catheter and a safety catheter insertion device. The catheter includes a catheter hub and a catheter tube. The safety catheter insertion device is selectively connectable to the catheter hub and includes a needle housing, needle assembly; and safety rod. The needle housing has a generally cylindrical elongate body. The needle assembly includes a needle and a needle hub with a tail portion having a safety rod channel defined therein. The needle assembly is slideably coupled to the needle housing between a first, ready for use position, wherein a portion of the needle extends through the catheter hub and exposes a sharpened tip, and a second, safe position, wherein the sharpened tip of the needle is housed by the needle housing to inhibit an inadvertent needle stick. The safety rod has a catheter hub engaging portion and a guide portion, wherein the guide portion traverses the safety rod channel of the needle assembly when the needle assembly is retracted from the first, ready for use position to the second, safe position, including pivotal interaction with the safety rod channel that causes the catheter hub engaging portion to rotate from a first, catheter hub retention position to a second, catheter hub disengagement position.

In some versions, the needle housing includes a needle lock configured to inhibit movement of the needle assembly from the second, safe position. In some versions, the needle lock includes a bottleneck on the needle housing that engages with a triangular protuberance on the needle assembly when in the second, safe position. In some versions, the needle assembly includes a flash chamber with a flash plug. In some versions, the needle housing includes a nose portion for at least partial positioning within the catheter hub. In some versions, the nose portion includes an aperture for the needle to pass through. In some versions, the needle housing includes a protrusion for receiving a portion of the safety rod. In some versions, the safety rod channel includes a "J" hook for pivoting the safety rod relative to the needle housing. In some versions, the catheter hub engaging portion and guide portion are oriented in the same direction.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 3b is a distal end view depicting the needle assembly of FIG. 3a.

FIG. 3c is a bottom perspective view depicting the needle assembly of FIG. 3a.

FIG. 5b is a cross section view depicting the safety catheter assembly of FIG. 5a.

FIG. 6b is a cross section view depicting the safety catheter assembly of FIG. 6a.

FIG. 7 is a perspective view depicting a unitary structure including a nose and a pair of catheter contacting engagement arms of a safety coupling according to a first embodiment of the disclosure.

FIG. 8 is a perspective view depicting an actuator of a safety coupling according to a first embodiment of the disclosure.

FIG. 9a is a cross sectional view depicting a catheter, a needle housing and an alternative version of a safety coupling according to a first embodiment of the disclosure in a first, ready for use position, wherein the catheter is securely connected to the needle housing by the safety coupling.

FIG. 9b is a cross sectional view depicting the safety catheter assembly of FIG. 9a in a second, safe position, wherein an actuator of the safety coupling has been shifted proximally, enabling an engagement arm of the safety coupling to pivot laterally away from the catheter, thereby releasing the catheter from the needle housing.

FIG. 12a is a distal perspective view depicting a collar of a safety coupling according to a second embodiment of the disclosure.

FIG. 12b is a proximal perspective view depicting the collar of FIG. 12a.

FIG. 13a is a distal perspective view depicting an actuator of a safety coupling according to a second embodiment of the disclosure.

FIG. 13b is a cross sectional view depicting the collar of FIG. 13a.

FIG. 14a is a distal perspective view depicting an engagement structure of a safety coupling according to a second embodiment of the disclosure.

FIG. 14b is a proximal perspective view depicting the engagement structure of FIG. 14a.

FIG. 17b is a distal perspective view depicting the retainer of FIG. 17a.

FIG. 18b is a distal perspective view depicting the collar of FIG. 18a.

FIG. 19 is a perspective view depicting a second version of a safety catheter assembly according to a third embodiment of the disclosure, wherein the safety catheter assembly includes a catheter and a catheter insertion device and is in a first, ready for use position, wherein the catheter is securely connected to the catheter insertion device by a safety coupling.

FIG. 20 is a distal perspective view depicting a flangeless collar of the safety coupling depicted in FIG. 19.

FIG. 21a is a distal perspective view depicting a flangeless retainer of the safety coupling depicted in FIG. 19.

FIG. 21b is a proximal perspective view depicting the flangeless retainer of FIG. 21a.

FIG. 22 is a perspective view depicting a flangeless catheter hub of the catheter depicted in FIG. 19.

FIG. 25b is a proximal perspective view depicting the grooved retainer of FIG. 21a.

FIG. 28a is a fragmentary, side view depicting a safety catheter assembly according to a fourth embodiment of the disclosure in a first, ready for use position, wherein safety catheter assembly includes a safety coupling having a actuator, an engagement structure and a mounting collar positioned relative to one another so as to engage a catheter of the safety catheter assembly.

FIG. 28b is a fragmentary cross sectional view depicting the safety catheter assembly of FIG. 28a in a second, safe position, wherein the actuator has been shifted proximally, forcing the engagement structure away from the catheter, and thereby releasing the catheter.

FIG. 29a is a distal end view depicting the safety catheter assembly of FIG. 28a in the first, ready for use position.

FIG. 29b is a distal end view depicting the safety catheter assembly of FIG. 28b in the second, safe position.

FIG. 31a is a distal, perspective view of a mounting collar of a safety coupling according to a fourth embodiment of the disclosure.

FIG. 31b is a proximal, perspective view of the mounting collar of FIG. 31a.

FIG. 32 is a distal, perspective view of an actuator of a safety coupling according to a fourth embodiment of the disclosure.

FIG. 33a is a distal, perspective view of an engagement structure of a safety coupling according to a fourth embodiment of the disclosure, wherein the engagement structure is in a catheter engaging closed configuration.

FIG. 33b is a top, perspective view of the engagement structure of FIG. 33a, wherein the engagement structure is in a catheter releasing open configuration.

FIG. 37a is a distal, perspective view of an engagement structure of a safety coupling according to a fifth embodiment of the disclosure.

FIG. 37b is a proximal, perspective view of the engagement structure of FIG. 37a.

FIG. 38 is a distal, perspective view of a collar of a safety coupling according to a fifth embodiment of the disclosure.

FIG. 39a is a distal, perspective view of an actuator of a safety coupling according to a fifth embodiment of the disclosure.

FIG. 39b is a proximal, perspective view of the actuator of FIG. 39a.

FIG. 40 is a distal, perspective view of a catheter hub according to a fifth embodiment of the disclosure.

FIG. 41a is a perspective view depicting a safety catheter assembly according to a sixth embodiment of the disclosure, wherein the safety catheter assembly includes a catheter and a catheter insertion device and is in a first, ready for use position, wherein the catheter is securely connected to the catheter insertion device by a safety coupling.

FIG. 41b is a perspective view depicting the intravenous catheter assembly of FIG. 41a in a second, safe position, wherein the catheter is released from the catheter insertion device and a sharp tip of an insertion needle of the catheter insertion device is safely housed within the catheter insertion device.

FIG. 46a is an exploded perspective view of the needle housing and the safety rod of FIG. 44 in a first, ready for use position.

FIG. 46b is an exploded perspective view of the needle housing and the safety rod of FIG. 44 in a second, safe position, wherein the safety rod is pivoted relative to the needle housing to a catheter release position.

Figure 1:
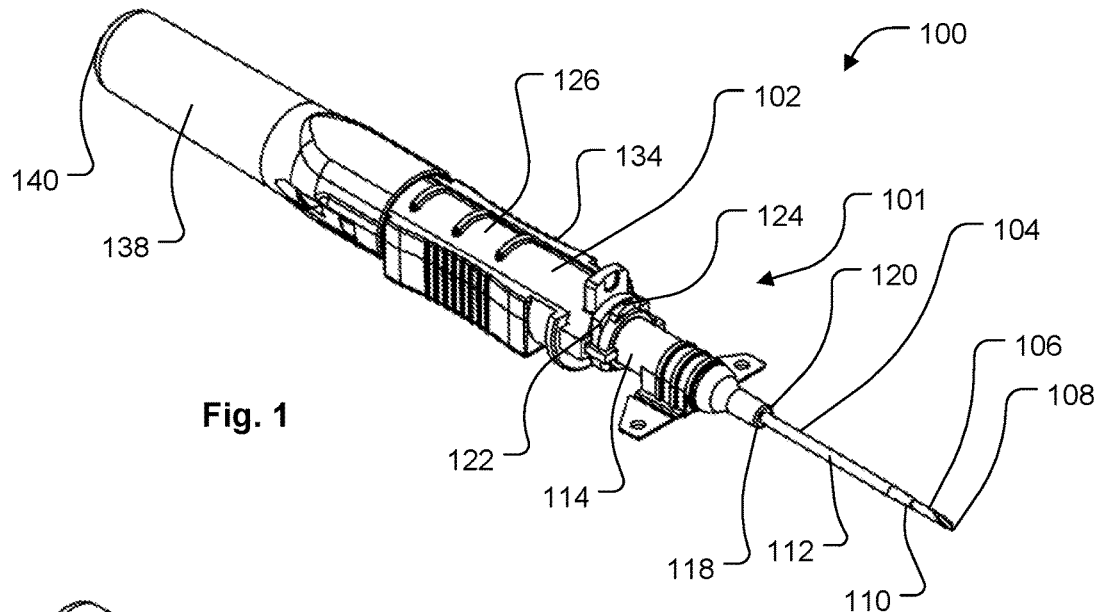
FIG. 1 is a perspective view depicting a safety catheter assembly according to a first embodiment of the disclosure, wherein the safety catheter assembly includes a catheter and a catheter insertion device and is in a first, ready for use position, wherein the catheter is securely connected to the catheter insertion device by a safety coupling.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Safety catheter assemblies typically include a catheter and a catheter insertion device. The catheter is provided in a first or ready for use position, in which the catheter is connected to the catheter insertion device. In particular, the catheter, which can include a catheter hub and catheter tube, can be positioned over the needle of the catheter insertion device, with a sharp tip of the needle protruding from a distal end of the catheter. In some embodiments, a protective sheath or needle cover can be operably coupled to either the catheter or the catheter insertion device, and positioned over the sharp needle tip to inhibit unwanted needle sticks. The safety catheter assembly, which can include the catheter and catheter insertion device, can be provided for use in a sterilized and assembled state, contained within a hermetically sealed package.

To insert the catheter into the vein of a subject, a clinician first removes the safety catheter assembly from the packaging. The needle sheath is removed to expose the sharp tip of the needle that is protruding from the distal end of the catheter tube. The clinician then punctures an identified site of the patient or subject with the sharp needle tip and urges the needle forward until the needle tip enters the vein of the subject. In some versions, an initial amount of blood can pass through a lumen of the needle, and enter the catheter and/or catheter insertion device such that the clinician can view the "flashback" of the blood to confirm entry into the vein. The catheter can then be moved distally over the needle, threading the tube of the catheter into the vein of the subject as the needle is held stationary. With the catheter positioned as desired, the clinician can withdraw the needle by pulling a needle assembly of the catheter insertion device proximally away from the subject while holding the catheter generally stationary with respect to the subject. The needle assembly is pulled proximally until the needle of the catheter insertion device is separated from the catheter and safely housed within the catheter insertion device, which is referred to as the second or safe position. In the safe position, the clinician can dispose of the catheter insertion device in a sharps container.

Various example embodiments of catheters are described herein for use in accessing the vein of a subject. It is to be appreciated, however, that the example embodiments described herein can alternately be used to access the vasculature of a subject at locations other than a vein, including but not limited to the artery of a subject. It is additionally to be appreciated that the term "clinician" refers to any individual that can perform a catheter insertion procedure with any of the example embodiments described herein or alternate combinations thereof. Similarly, the term "subject," as used herein, is to be understood to refer to an individual or object in which a catheter is to be inserted, whether human, animal, or inanimate. Various descriptions are made herein, for the sake of convenience, with respect to procedures being performed by a clinician to access the vein of a subject, while the disclosure is not limited in this respect.

It is also to be appreciated that the term "distal," as used herein, refers to the direction, taking along an axis that lies parallel to the needle of a safety catheter assembly that is closest to the subject during catheter insertion. Conversely, the term "proximal," as used herein, refers to the direction lying along the axis parallel to the needle that is farther away from the subject when the catheter is inserted into the vein of the subject, opposite to the distal direction.

According to various example embodiments, the safety catheter assemblies disclosed herein can include a safety coupling. The safety coupling can be configured to couple the catheter hub to the catheter insertion device in the first or ready for use position and release the catheter hub from the catheter insertion device in the second or safe position. In some embodiments, the safety coupling can include one or more catheter hub contacts that inhibit release of a catheter from an insertion device until after the sharp needle tip of the insertion device is in a safe position, where access to the sharp needle tip is inhibited. Release of the catheter from the insertion device can occur during a catheter insertion procedure without the need to perform additional steps aside from safely retracting the needle. In this respect, the catheter can be "passively" released by a clinician to obtain "passive" safety. By way of example, the catheter can be released when a clinician pulls on a portion of the insertion device as the clinician withdraws the needle from the catheter.

The term "safety coupling," as used herein, is to be understood to refer to features of a catheter insertion device that inhibit the release of a catheter until after the catheter insertion device is in a safe position. Some or all of the features of the safety coupling can be integral with other components of the needle housing, needle assembly, and/or other components of an overall safety catheter assembly. In this respect, the term "safety coupling" does not necessarily refer to a component that is separate from the needle housing and/or needle assembly. It is to be appreciated, however, that the safety coupling can be a separate component assembly from the needle housing, according to some example embodiments.

According to various example embodiments, a catheter insertion device includes a needle lock that engages a needle assembly at a position that is proximal to the needle tip to inhibit the needle tip from being accessed after the needle is used to insert a catheter. In this manner, access to the sharp tip is inhibited with the needle in a safe position. In some embodiments, the catheter insertion device can include an actuator that is shifted proximally by interaction with a feature of the needle, such as a transition or bump, during needle withdrawal to the safe position. The proximal shifting of the actuator can cause the hub to be released from engagement by hub contacts of the insertion device after the needle reaches the safe position. One or more of the hub contacts can engage an outer surface and/or an interior surface of the catheter hub prior to being released from the insertion device.

A. First Embodiment

Referring to FIGS. 1-9, a safety catheter assembly 100 according to a first embodiment of the disclosure is depicted. FIGS. 1-8 depict a first version of the safety catheter assembly 100, while FIGS. 9a-b depict an alternative version of the safety catheter assembly 100.

Figure 2A:
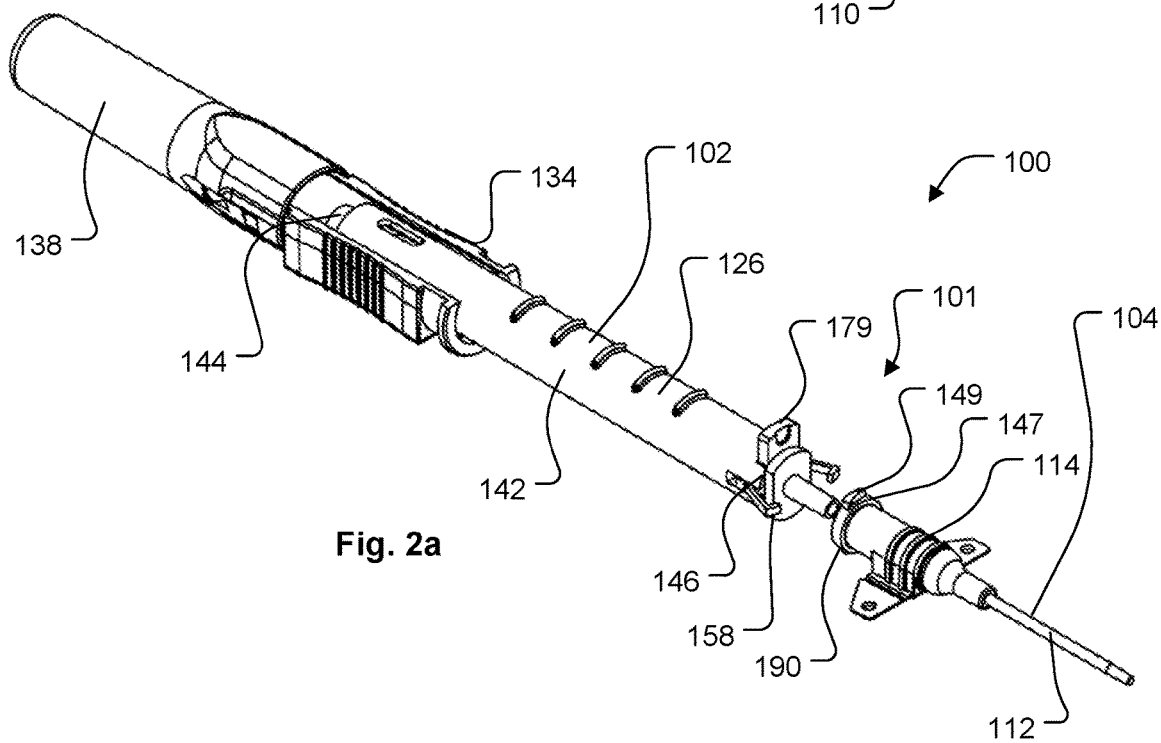
FIG. 2a is a perspective view depicting the intravenous catheter assembly of FIG. 1 in a second, safe position, wherein the catheter is released from the catheter insertion device and a sharp tip of an insertion needle of the catheter insertion device is safely housed within the catheter insertion device.

As depicted in FIGS. 1 and 2a, safety catheter assembly 100 generally includes a catheter insertion device 102 and a catheter 104. FIG. 1 depicts the safety catheter assembly 100 in a first, ready for use position, while FIG. 2 depicts the safety catheter assembly 100 in a second, safe position. In the ready for use position, the catheter 104 is securely connected to the catheter insertion device 102 by a safety coupling 101. The catheter 104 is positioned over the insertion needle 106 of the catheter insertion device 104 with the sharp tip 108 extending from a distal end 110 of the catheter tube 112. In the safe position, the sharp tip 108 of insertion needle 106 can be positioned internally to an envelope of the catheter insertion device 102 to inhibit access to the sharp tip 108 by a clinician, subject, or others. The catheter 104 can be released from the catheter insertion 102 device when the catheter tube 112 of the catheter 104 is inserted at least partially within the vasculature of a subject.

Figure 11A:
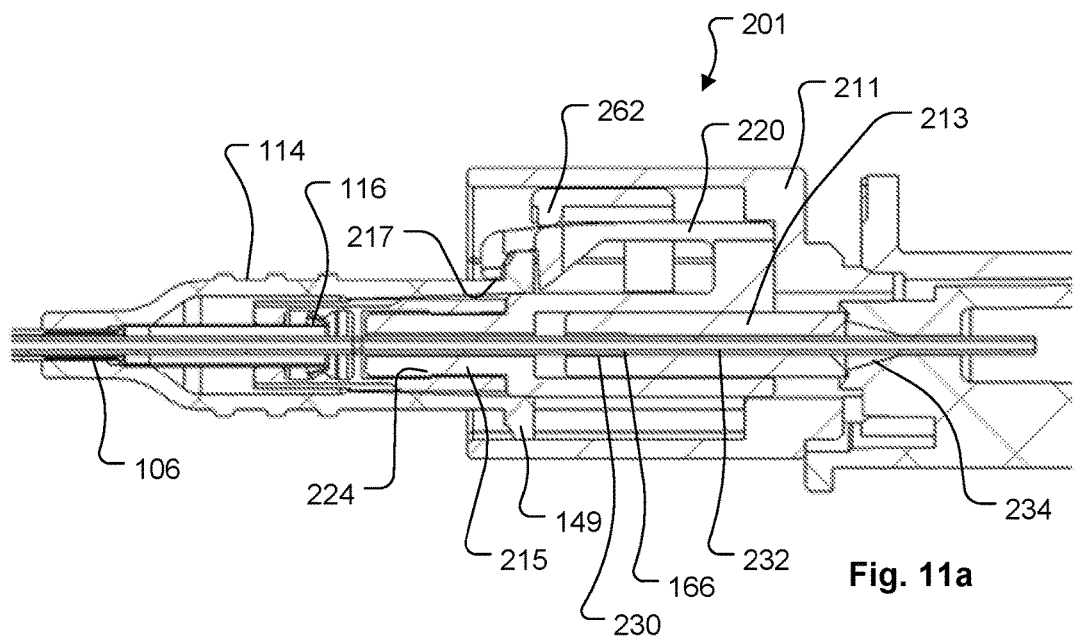
FIG. 11a is a fragmentary cross sectional view depicting a safety catheter assembly according to a second embodiment of the disclosure in a first, ready for use position, wherein a catheter contacting engagement arm of an engagement structure is held in contact with a catheter by an actuator of the safety coupling.
Figure 11B:
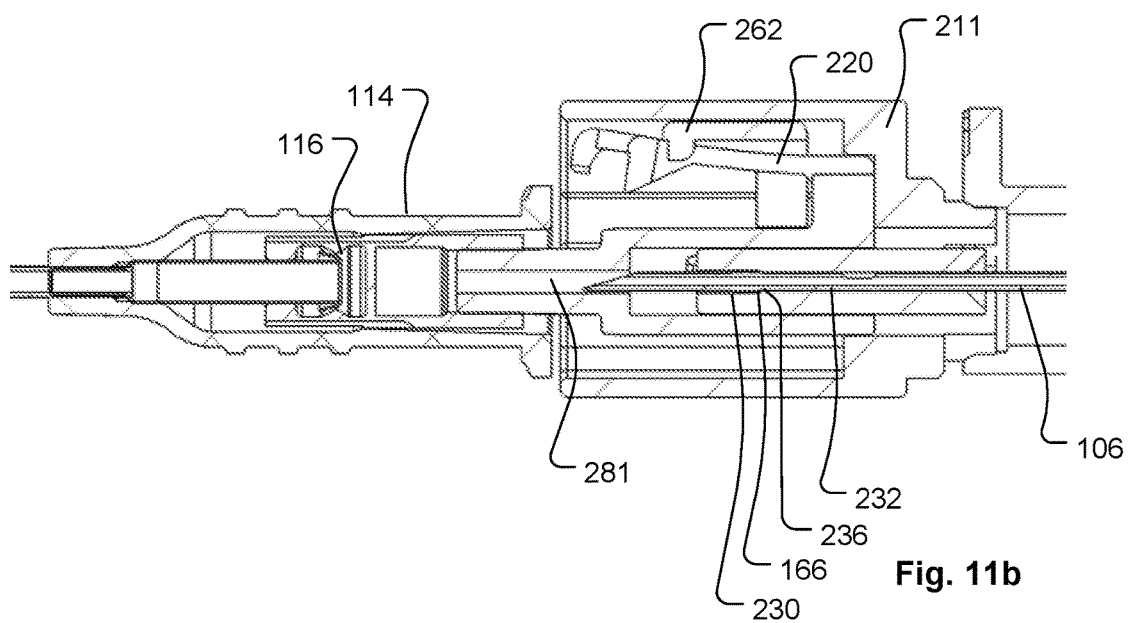
FIG. 11b is fragmentary cross sectional view depicting the safety catheter assembly of FIG. 11b in a second, safe position, wherein the actuator has been shifted proximally, enabling the engagement arm to pivot laterally away from the catheter, and thereby releasing the catheter.

Referring to FIG. 2a, the catheter 104 generally includes a catheter tube 112, a catheter hub 114, and a blood control valve 116 that lies internal to the catheter (as depicted in other embodiments, such as FIGS. 11a-b). In some versions, the blood control valve 116 can be comprised of a septum or valve to enable sealing of the fluid passageway to restrict or inhibit bodily fluid from leaking out of catheter hub 114 when catheter 104 is inserted into a patient's vein and the insertion needle 106 is removed. Various catheter hub 114 designs having septum and/or valve are disclosed in a concurrently filed application entitled "Intravenous Catheter Assembly Design,", which is incorporated by reference herein.

The catheter tube 112 extends from a distal end 110 to a proximal end 118 where the tube is connected to a catheter hub 114 (alternately referred to as a catheter connector). The catheter tube 112 defines a lumen that provides a fluid pathway between the vein of a subject and the catheter hub 114. The catheter hub 114 includes a distal end 120 and a proximal end 122 defining a connector 124 configured to mate with other medical components that can be used in treatment of a subject, such as IV fluid supply devices, sample collection devices, extension tubes, and the like. The connector of the catheter hub 114 can be constructed to include a "luer" type connection, such as can be specified by International Standards Organization specifications ISO 594-1, ISO 594-2, and/or ISO 80369.

Figure 2B:
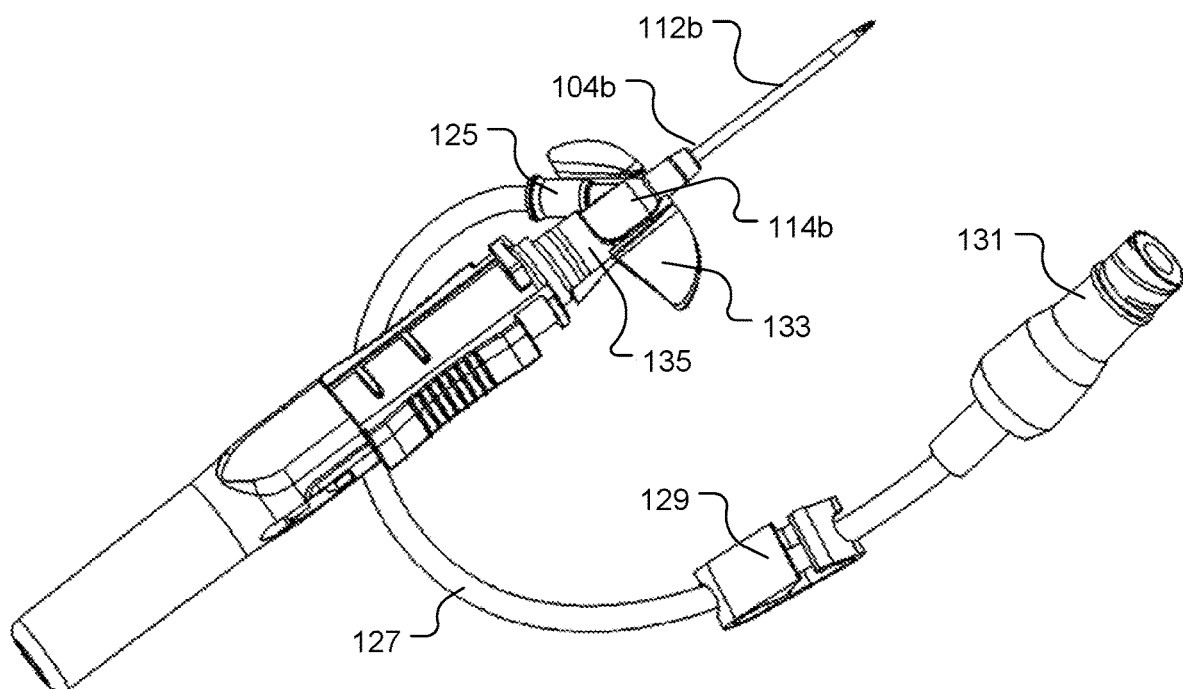
FIG. 2b is a perspective view depicting another version of a safety catheter assembly according to a first embodiment of the disclosure in a first, ready for use position, wherein the catheter hub includes a side port, wings, hollow tubing, a tubing clamp, and a tube connector.

Referring to FIG. 2b, in some versions, catheter 104b can include a side port 125. The side port 125 can extend away from the catheter hub 114b at an oblique angle to the catheter tube 104b. The side port 125 can provide a connection point to one or more lengths of tubing 127, so that the inside of the tubing 127 is in fluid communication the lumen of catheter tube 112b.

The hollow tubing 127 can include a tubing clamp 129 and a tube connector 131. The hollow tubing 127 can be substantially transparent or translucent to enable the observation of fluid within the hollow tubing 127. The tube clamp 129 can be constructed of a resilient material that can be deformed to selectively occlude hollow tubing 127 to restrict the passage of fluid. The tube connector 131 can be configured to connect hollow tubing 127 to an IV fluid supply line. In one version, the tube connector 131 is a luer lock. In another version, the tube connector 131 is a needle-free connector, for example the connector described in U.S. Pat. No. 7,713,248 (depicting a needle-free connector marketed by ICU Medical, Inc. under the CLAVE trademark), which is hereby incorporated by reference herein.

The catheter hub 114b can include one or more wings 133 that extend radially from the catheter hub 114b. The one or more wings 133 can generally extends outwardly from the central axis of the catheter huh 114b, so as to provide an adequate gripping surface for the clinician, as well as an extended surface for aid in securing the catheter hub 114b in place on the subject. In one version, the one or more wings 133 are integrally molded onto a portion of the catheter hub 114b. In another version the wings 133 are coupled to the catheter hub 114b via a collar 135 or the like that at least partially surrounds the catheter hub 114b.

Catheter 104 or 104b, or versions thereof, can be used in conjunction with this embodiment as well as any of the other embodiments or versions of the embodiments described or referenced by this disclosure.

Figure 3A:
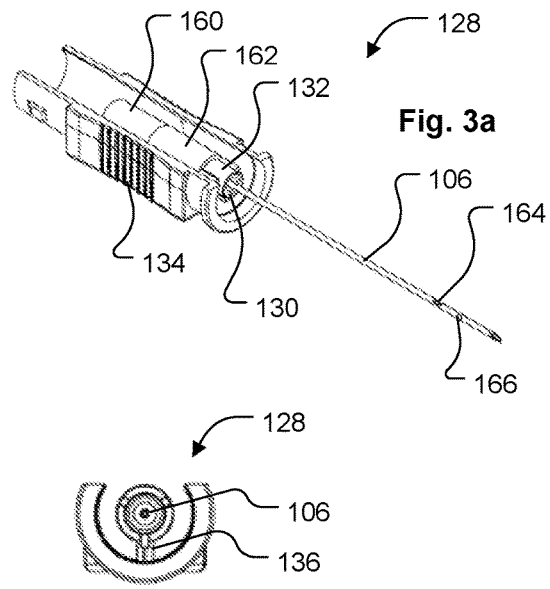
FIG. 3a is a side perspective view depicting a needle assembly of a catheter insertion device, which can be common to all embodiments of the disclosure.
Figure 3C:
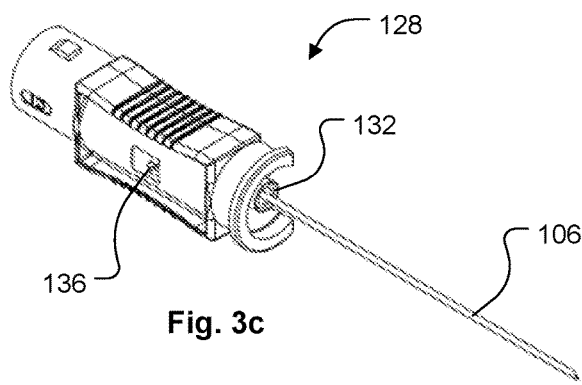
Figure 3B:
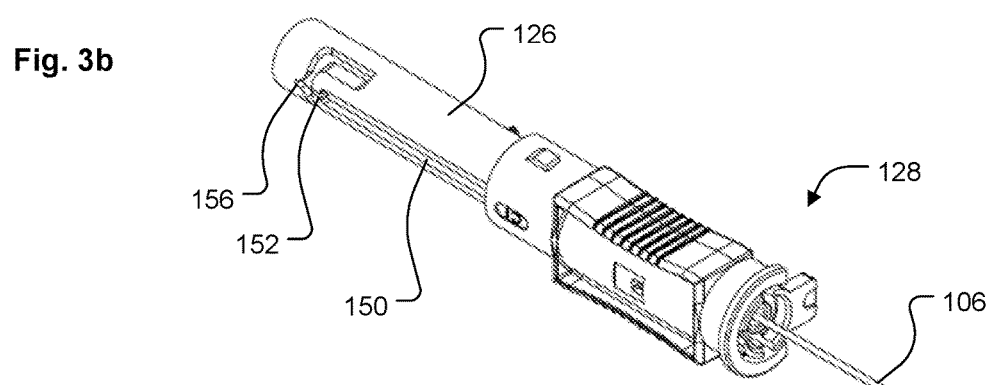

The catheter insertion device 102 includes a needle assembly 128 that is movable with respect to a needle housing 126 from a first, ready for use position (as depicted in FIG. 1), to a second, safe position (as depicted in FIG. 2a). As best depicted in FIGS. 3a-c, the needle assembly 128 can include an insertion needle 106 operably coupled to a needle hub 132.

The needle 106 can includes an elongate, cylindrically shaped metal structure defining a lumen that extends from a sharp distal end tip 108 to a proximal end 130. The sharp distal end tip 108 can be constructed and arranged to pierce the skin of a subject during catheter insertion. The needle can include a transition 166 or needle bump that has a different cross sectional size and/or shape than portions of the needle that lie proximal to the transition. Needle transitions (alternately referred to as needle or cannula bumps) can be created by crimping opposed sides of the needle 106, or otherwise disrupting the structure of the needle 106, so that the outer surface of the needle 106 extends to a larger radial position than other portions of the needle 106, as measured from the center of the needle axis. Transitions can be formed differently, according to alternate embodiments, such as by adding material to the exterior of the needle, among other ways. The proximal portion 130 of the needle can be connected to the needle hub 132.

The needle hub 132 can be connected to a needle grip 134 positioned on the exterior of the needle housing 126 when assembled thereto for access by a clinician. The needle hub 132 and needle grip 134 can be operably coupled to one another by a protuberance 136 that can be formed from the same unitary structure as the needle grip 134 and the needle hub 132.

In one version, the needle assembly 128 can be constructed to provide a visual indication of flashback when the sharp tip 108 of the needle 106 enters the vein of a subject. In this version, the needle hub 132 includes a flash chamber 160, wherein the needle lumen is in fluid communication with a flash chamber 160. When the sharp tip 108 enters a vein during catheter insertion, blood enters the needle lumen from the vein and flows proximally through the needle 106 and into the flash chamber 160. The flash chamber 160 can be sealed at one end by a flash plug 162. The flash plug 162 can be made of an air permeable, hydrophilic material that enables the passage of air, but that inhibits the passage of liquid. Air that resides in the needle lumen and flash chamber 160 is therefore pushed through the flash plug 162 by the incoming blood, until the blood reaches the flash plug 162 or is otherwise stopped. The needle hub 132, or portions thereof, can be constructed of a clear or translucent material to enable a clinician to view the presence of blood within the flash chamber. In this respect, the clinician can be alerted when the needle has entered the vein of the subject by the presence of blood in the flashback chamber.

In some embodiments, flash chamber 160 can further include a diagnostic sampling port configured to enable selective access to fluid contained within flash chamber 160. Various needle assemblies having diagnostic sampling ports are disclosed in a concurrently filed application entitled "Needle Assembly with Diagnostic Analysis Provisions,", which is incorporated by reference herein.

In some versions, features of the needle assembly 128, other than the flashback chamber 160, can provide an indication that the needle tip 108 has entered the vein of a subject. For example, the needle can include a notch 164. In this version, blood flow enters the needle lumen when the sharp tip 108 enters the vein. As blood flows proximally in the needle lumen, some blood passes thorough the notch 164 and into the annular space that lies between the exterior of the needle 106 and the interior of the catheter tube 112. The presence of blood in the annular space can be viewed by a clinician through clear or translucent portions of the catheter tube 112, providing an indication that the needle tip is present in a vein.

Figure 4A:
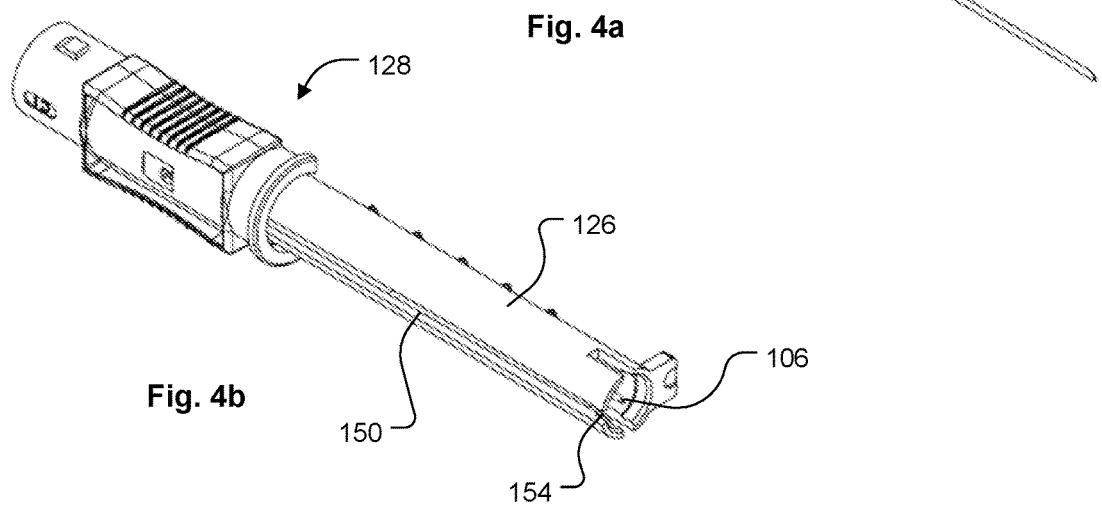
FIG. 4a is a bottom perspective view depicting an interaction between a needle assembly and a needle housing of a catheter insertion device, which can be common to all embodiments of the disclosure, wherein the needle assembly is positioned relative to the needle housing in a first, ready for use position.
Figure 4B:
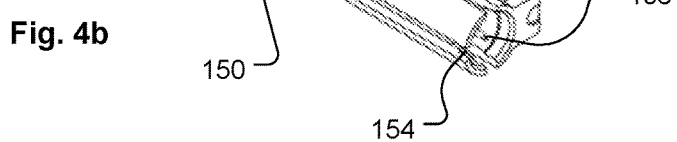
FIG. 4b is a bottom perspective view depicting the interaction between a needle assembly and a needle housing of a catheter insertion device of FIG. 4a, wherein the needle assembly is approaching a second, safe position relative to the needle housing.

As best depicted in FIGS. 2a and 4a-b, the needle housing 126 can have a generally cylindrical, elongate body 142 that extends from a proximal end 144 to a distal end 146. A longitudinal slot 150 can be formed along an underside of the needle housing 126 and extend from a proximal slot end 152 near the proximal end 144 of the needle housing 126 to a distal slot end 154 near the distal end 146 of the housing 126.

The needle hub 132 can be slideably coupled to the needle housing 126. For example, the needle hub 132 can have a "C" shaped cross section conformed to fit around the outer surface of the needle housing 126 in a manner that inhibits the needle hub 132 from readily separating from the needle housing 126, yet enables the needle hub 132 to slide along the longitudinal axis of the needle housing 126 with minimal resistance. In one version, the slot 150 can slidably receive the protuberance 136 of the needle assembly 128, with the needle grip 134 positioned outside of the needle housing 126 and at least a portion of the needle hub 132 and needle 106 positioned internally to the needle housing 126, thereby at least partially housing these features. Accordingly, the needle hub 132 can be configured to slide along a groove 150 to restrict the needle hub 132 from rotating about the longitudinal axis of the needle housing 126. The protuberance 136 slideably received within the groove 150, thereby enables linear movement of the needle hub 132 substantially parallel to the longitudinal axis of the needle housing 126, but restricts the rotational movement of the needle hub 132 relative to the needle housing 126.

The slot 150 can guide the needle assembly 128 in motion with respect to the needle housing 126 between the first, ready for use position (as depicted in FIG. 4a) and the second, safe position (as depicted in FIG. 4b). In the first, ready for use position, a portion of the needle 106 extends from needle housing 126, such that the sharpened tip 108 of the needle 106 protrudes beyond the needle housing 126. In the second, safe position, the needle 106 is withdrawn, and the sharpened tip 108 is housed within the needle housing 126 in a manner intended to reduce or eliminate the likelihood of an inadvertent needle stick.

After positioning in the second, safe position, return movement of the needle assembly 128 back toward the first, ready for use position can be inhibited by a needle lock 156. The needle lock 156 can thus be configured to interlock the needle hub 128 to the needle housing 132 in the second, safe position. In one version, the needle lock 156 can be positioned on a proximal portion of the housing 126 at the proximal slot end 152 to engage the protuberance 136. Several different types of locking mechanisms can be used for this purpose. For example, in one version, the slot 150 of the needle housing 126 can have a bottleneck 156 defined in it, where the bottleneck portion of the groove 150 generally has a narrower width than the rest of the groove 150. Protuberance 136 of needle hub 136 can be triangular or wedge-like in shape where the apex of the wedge faces the bottleneck 156 when in the first, ready for use position. When an external force is applied to the needle hub 136 in an effort to slide it into the second, safe position, the apex of the wedge of the protuberance 136 comes into contact with the bottleneck 156. The bottleneck 156, which can have a width narrower than that of the protuberance 136 will initially resist movement of the protuberance 136 through the bottleneck 156. However, with sufficient force the wedge-shape protuberance 136 will cause the bottleneck 156 to temporarily deform, thereby enabling the protuberance 136 to pass through the bottleneck 156. For example, in one version, the interaction between the wedge-shape protuberance 136 and the bottleneck 156 will create an audible "click" sound when the protuberance 136 to passes through the bottleneck 156. Thereafter the protuberance 136 will be unable to pass back through the bottleneck 156 in the opposite direction, and the needle 106 will be locked in the second, safe position relative to the needle housing 126.

In some versions, the catheter insertion device 102 can include an end cap 138 (as depicted in FIGS. 1-2a). The end cap 138 can be connected to the needle grip 134 and/or needle hub 132, thereby covering the proximal end of the needle housing 126. The end cap 138 can have a proximal end 140 that can provide a surface against which a clinician can press during a catheter insertion procedure, as discussed herein.

At the distal end 146 of the needle housing 126, the needle assembly 128 can engage a distal stop 158 to inhibit the needle assembly 128 from moving distally beyond the first, ready for use position with respect to the needle housing 126. The distal stop 158 can include a proximally facing portion of a safety coupling 101 that engages a distal end of the needle grip 134 to inhibit further distal movement of the needle assembly 128. Alternate distal stops are also contemplated, including stops formed by interaction between the protuberance and the distal end of the slot, among others. The safety coupling 101 can be positioned near the distal end 146 of the needle housing 126.

Figure 5A:
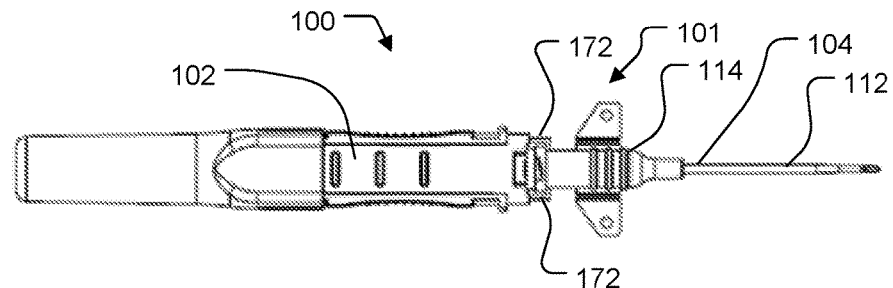
FIG. 5a is a top view depicting a safety catheter assembly according to a first embodiment of the disclosure in a first, ready for use position.
Figure 5B:
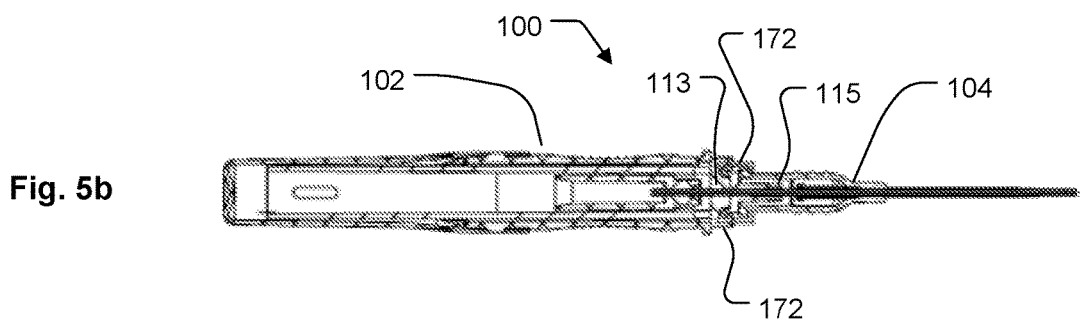
Figure 6A:
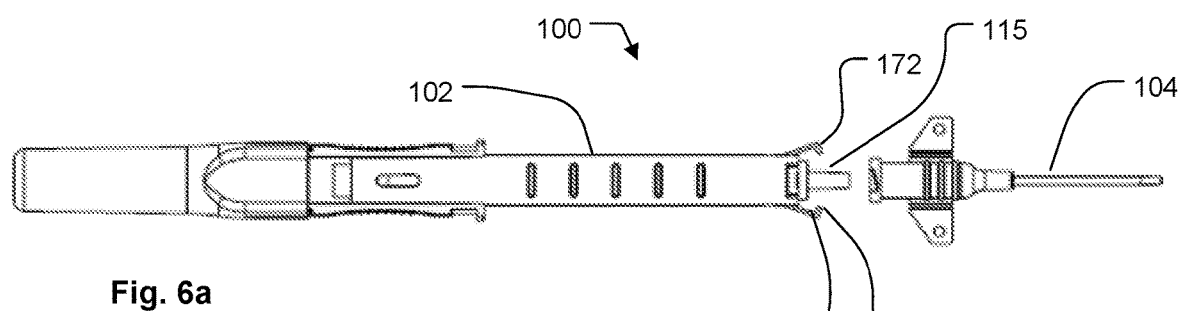
FIG. 6a is a top view depicting the safety catheter assembly of FIG. 5a in a second, safe position.
Figure 6B:
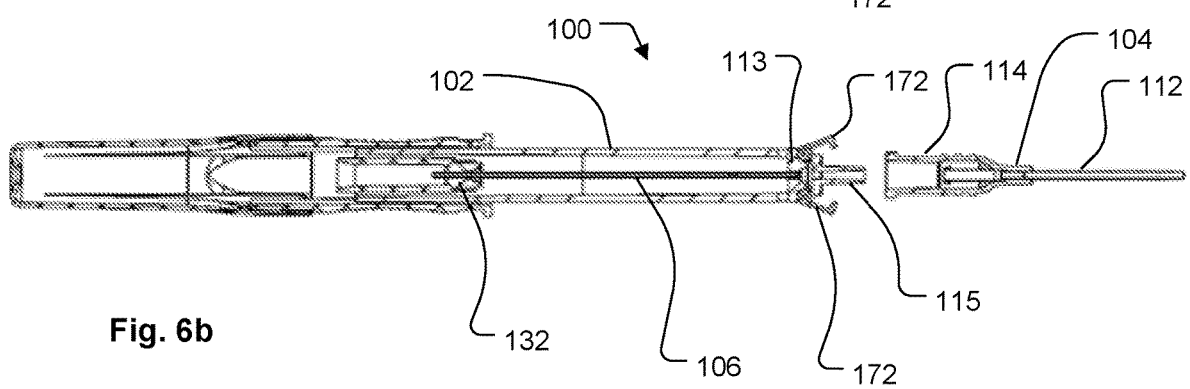

As best depicted in FIGS. 5a-8, the safety coupling 101 can include a nose 115, a pair of engagement arms 172 each having an exterior hub contact 117, and an actuator 113. The safety coupling 101 is shiftable between a first, ready for use position (as depicted in FIGS. 1, 5a, and 5b), wherein the actuator 113 is positioned to hold the external hub contacts 117 in engagement with an external surface 178 of the catheter hub 114, thereby inhibiting release of the catheter hub 114 from the catheter insertion device 102, and a second, safe position (as depicted in FIGS. 2, 6a, and 6b), wherein the actuator 113 is shifted proximally, into a disengaged position that enables the engagement arms 172 to move or pivot laterally away from the catheter hub 178. In particular, when the needle 106 is pulled proximally to remove the needle 106 from the catheter 104, the needle transition 166 can contact the actuator 113, thereby enabling the needle 106 to shift the actuator 113 of the safety coupling 101 in the proximal direction. Thus, proximal movement of the actuator 113 releases the exterior hub contacts 117 from engagement with the catheter hub 178 so that the catheter 104 can be removed from the catheter insertion device 102.

In the first, ready for use position, the safety coupling 101 is configured with the actuator 113 in the distal, engaged position. The catheter hub 114 is positioned over the nose 115 and in contact with the hub plate 180. The actuator arms 182 hold the engagement arms 172 and exterior hub contacts 117 in engagement with the catheter 104. This occurs with the engagement arms 172 being forced inwardly by a portion of the interior wall 184 of an arm box portion 186 of an actuator arm 182. The distal portion of each engagement arm 172 is received into the distal portion receiver 171 of an arm box portion 186. The actuator body 188 contacts the hub plate 180 of the nose 115 to inhibit distal movement of the actuator 113. Contact between the actuator arms 182 and the engagement arms 172 can also inhibit further distal movement of the actuator 113 from the distal, engaged position. The distal end of the needle grip 134, which lies at a larger diameter than the actuator arms, inhibits the actuator arms 182 from being accessed and moved proximally, prior to the needle assembly also being moved proximally.

In the second, safe position, the actuator 113 is shifted proximally to a disengaged position. Proximal movement of the actuator 113 also causes the actuator arms 182 to move proximally. When the actuator arms 182 move proximally, the engagement arms 172 pivot outwards, disengaging exterior hub contacts 117 from an exterior surface 178 of the catheter hub 114. This disengages the catheter 104 from the safety coupling 101 and enables the catheter 104 to be removed therefrom. It is to be appreciated that the external hub contacts 117, or other portions of the safety coupling 101, can remain in contact with the catheter hub 114 while being disengaged therefrom.

As best depicted in FIG. 7, the nose 115 can include a body 192, a tapered extension 194, a hub plate 180, and a mounting collar 196 for the overall safety coupling 101. The nose 115 can be connected to the distal end of the needle housing 126 with the mounting collar 196 positioned internally to the needle housing 126 and the hub plate 180 abutting the distal end 146 of the needle housing 126. The tapered extension 194 can extend distally from the hub plate 180 and can be sized and shaped to be received within the catheter hub 114. In some version, tapered extension 194 can contact a blood control valve within the catheter hub 114 to provide guidance during catheter 104 removal. Contact between the tapered extension 194 and a blood control valve can also provide a seal to contain flashback blood that lies between the needle 106 and catheter tube 112.

A passage 198 can extend through the nose 115, including the mounting collar 196, hub plate 180 and tapered extension 194. The passage 198 can be sized to enable the needle 106, including the needle transition or bump 166, to pass without restriction from the ready for use position to the safe position. When the needle assembly 128 is in the safe position, the sharp needle tip 108 can be positioned inside of the passage 198. The blunt distal end of the tapered extension 194 can contact surfaces that are brought into contact with the distal end of the catheter insertion device 102 instead of the sharp needle tip 108. In this manner, unwanted needle sticks are inhibited. The needle lock 156, when engaged, inhibits the sharp tip 108 from emerging from the nose 115, as discussed herein.

The engagement arms 172 can extend outwardly and distally from hub plate 180 and can be connected to the hub plate 180 by resilient members 141. In one version, resilient members 141 are leaf springs. Engagement arms 172 can be formed from a common unitary structure with the nose 115, although other configurations are also contemplated with the nose and the engagement arms formed from separate components. Each engagement arm 172 has a longitudinal portion, including a distal portion 143 and proximal portion 145 that lies generally parallel to the needle 106 when the catheter insertion device 102 is in the ready for use position. A hub retention finger 195 is arranged orthogonally to the distal portion 143 of each engagement arm 172 and extends laterally inward, ending in an external hub contact 117. The proximal portion 145 extends proximally of the resilient member 141 that connects the engagement arm 172 to the nose 115. The distal portion 143 can be substantially longer than proximal portion 145, although alternate configurations are also contemplated.

The external hub contacts 117 can include both a laterally inward facing surface 175 and a proximally facing surface 177. The laterally inward facing 175 and proximally facing surface 177 can act together to hold the catheter 104 in engagement to the catheter insertion device 102. The laterally facing surface 175 conforms to the corresponding surface of the catheter hub 114 and can be concave in shape. The proximally facing surface 177 can also conform to the corresponding surface of the hub 114, which can include a rim or flange 147 that extends circumferentially about and laterally away from the proximal end 122 of the catheter hub 114. In alternate versions, the rim 147 can also include a rib or luer thread 149 that can be contacted by an exterior hub contact 117 of an engagement arm 172.

The resilient members 141 connect the engagement arms 172 to the nose 115 and enable the engagement arms 172 and exterior hub contacts 117 to move out of engagement with the catheter hub 114 when the actuator 113 is in the proximal, disengaged position. The resilient members 141 can have a curved structure that extends between the juncture of distal portion 143 and proximal portion 145 to a proximal aspect of hub plate 180. The resilient members 141 can act to bias the engagement arms 172 and external hub contacts 117 away from the catheter hub 114 (as depicted FIGS. 2, 6a, 6b, and 7). In this respect, the resilient members 141 and the external hub contacts 117 are disengaged from the catheter 104 merely by the actuator moving to enable the second, safe position. The resilient members 141 bias or urge the external hub contacts 117 away from the hub 114. The resilient members 141 can be formed of the same unitary structure as the nose 115 and engagement arms 172, or can be formed separately.

Some versions include a pair of engagement arms 172 that are positioned on lateral sides of the catheter hub 114 when the safety catheter assembly 100 is positioned for catheter insertion in the ready for use position. Placement of the engagement arms 172 on the lateral sides can promote easier separation of the catheter 104 from the catheter insertion device 102. In other versions, the engagement arms 172 can be oriented differently with respect to the catheter hub 114, as the present disclosure is not limiting in this respect. For example, safety couplings 101 can include different numbers of engagement arms 172, including as few as one engagement arm 172 or three or more engagement arms 172, according to other versions.

As best depicted in FIG. 8, the actuator 113 can include an actuator body 188 and actuator arms 182. The actuator arms 182 can contact the engagement arms 172 in a manner that engages or holds the external hub contacts 117 against the catheter hub 114 to inhibit catheter 104 release when the actuator 113 is shifted distally. The actuator 113 generally includes an actuator body 188 having a central portion and a pair of actuator arms 182. The actuator arms 182 can include a first arm and a second arm; however, alternate versions can include a lesser or greater number of actuator arms 182, particularly where other versions include a different number of engagement arms 172. The actuator 113 and actuator arms 182 can be formed from a common unitary structure. According to alternate versions, the actuator arms 182 and nose 115 are features of separate components rather than a unitary structure.

The actuator 113 includes a central portion having ring collar 151. The ring collar 151 generally includes cylindrical portion 153 and frustoconical portion 155. The ring collar 151 defines an actuator needle passage 157 therethrough. The needle passage 157 includes narrow portion 159 and wide portion 161. The narrow portion 159 is proximal to the wide portion 161 and is sized to receive the needle 106 in tight fitting apposition therethrough. The wide portion 161 is slightly wider than narrow portion 159. That is, the diameter or cross sectional dimension of the actuator needle passage 157 is greater in at least portions of the wide portion 161 than in the narrow portion 159. The transition between the wide portion and the narrow portion defines a needle abutment 163 that is shaped and sized to inhibit the passage of the needle transition or needle bump 166.

Proximal movement of the needle 106 causes the needle transition 166 to contact and engage the needle abutment 163 when the needle assembly 128 is moved near or within the safe position. This engagement between the needle transition 166 and needle abutment 163 enables the actuator 113 to be shifted proximally by movement of the needle 106 during needle withdrawal. Actuator arms 182 are moved proximally with the actuator shift to release the engagement arms 172 and hub contacts 117 from engagement with the catheter 104 so that the catheter can be released after the needle assembly 128 reaches the safe position. It is to be appreciated that FIGS. 1-8 depict but one configuration of an actuator and needle abutment, and that other configurations are also contemplated. By way of non-limiting example, alternate versions can lack a needle passage 157 having a wide portion 161 and a narrow portion 159. In such versions, the needle abutment 163 can be formed from a distally facing surface of the actuator 113 that contacts a needle transition 166.

The actuator arms 182 can be similar in structure to one another and generally can include a radial portion 165 and an arm box portion 186. The radial portion 165 extends outwardly from the cylindrical portion 153 and supports the arm box portion 186 at a peripheral end thereof. The arm box portion 186 generally includes an exterior wall 167 and side walls 169. The side walls 169 can be substantial mirror images of each other. Within the exterior wall 167 and side walls 169 is distal portion receiver 171. The distal portion receiver 171 is sized and shaped to receive the distal portion of the engagement arm 172. In some versions, the arm box portion 186 further includes an exterior wall 167 and side walls 169 defining the distal portion receiver 171 into which the distal portion 143 of the at least one engagement arm 172 is receivable.

The actuator 113 can be guided by various features that interact with other components of the insertion device 102 as the actuator 113 is shifted proximally. In some versions, the radial portion 165 of the actuator arm 182 is captured by a slot formed in a needle housing 126 of the safety catheter assembly 100. The cylindrical portion 153 of the actuator 113 can be sized for sliding contact with the inner surface of the needle housing 126. Interaction between side walls 169 of the actuator arms 182 (or other portions of the actuator arms) and the engagement arms 172 can also provide guidance and stability as the actuator 113 is shifted proximally.

In one version, at least a portion of the actuator 113 is located proximal to the nose 115 and is abuttable to an interior of the proximal portion 145 of the at least one engagement arm 172. The actuator 113 can be shiftable between a distal position (as depicted in FIG. 9a), wherein the actuator 113 holds the at least one engagement arm 172 in a first, engaged position by inhibiting inward movement of the proximal portion 145 of the at least one engagement arm 172 and a proximal position (as depicted in FIG. 9b), wherein the proximal portion 145 of the at least one engagement arm 172 can move inwardly and the distal portion 143 of the at least one engagement arm 172 is released from the catheter hub 114 and the catheter hub 114 can be removed from the nose 115.

In operation, safety catheter assembly 100 can be removed from the provided packaging. A needle sheath can be removed from the safety catheter assembly 100. The clinician can select and prepare an insertion site for catheter placement. In some versions, safety catheter assembly 100 can include at least one of a self-contained antiseptic swab, and a tourniquet for treatment and/or preparation of the insertion site. Various safety catheter assemblies having self-contained antiseptic swabs and/or tourniquets are disclosed in a concurrently filed application entitled "Antiseptic Sheath with Site Preparation Provisions," which is incorporated by reference herein.

After preparation of the insertion site, the clinician can puncture the selected site of a subject with the sharp needle tip 108 and urge the needle 106 forward until the needle tip 108 enters the vein of the subject. To accomplish this, the clinician can hold the safety catheter assembly 100 with a finger and thumb on opposed sides of the needle grip 134 as the needle is urged into the subject. The clinician can optionally position the palm of their hand against a proximal end 140 of the needle assembly (e.g., the end cap 138). Once flashback of blood is witnessed to confirm entry of the needle into the vein, the clinician can stop moving the needle forward.

The clinician can advance the catheter 104 after the needle tip 108 initially enters the vein. To accomplish this, the needle grip 134 is held stationary to inhibit further distal movement of the needle 108. The clinician moves the needle housing 126 distally to urge the catheter 104 forward, over the stationary needle, and further into the vein of the subject. The clinician can push a tab 179 of the needle housing 126 forward with their finger to do this. Forward movement of the needle housing is stopped once the catheter is positioned at a desired depth in the subject. Catheter advancement into the subject moves the needle housing 126 and catheter 104 distally, relative to the needle 108 and needle assembly 128, without placing the needle assembly 128 in the first, safe position and without shifting the actuator 113 proximally to release the catheter 104 from the catheter insertion device 102.

The needle housing 126 and catheter 104 are held generally stationary relative to the subject as the needle assembly 128 is pulled proximally to withdraw the needle 108 from the subject and the catheter 104. The clinician can pull the needle assembly 128 with their finger and thumb in the same orientation on the needle grip 134 as during needle insertion, without having to reorient their grasp. Alternately, the clinician can reorient their grip and/or grab other portions of the needle assembly 128, including the end cap 138, to perform needle withdrawal. According to either approach, the catheter 104 is released from the insertion device 102 as a part of the needle 106 withdrawal motion without the clinician performing additional steps. This occurs when the needle transition 166 contacts the needle abutment 163 of the actuator 113 to enable the needle assembly 128 to shift the actuator 113 proximally from the engaged position to the disengaged position. The needle tip 108 is also positioned internally to the insertion device 102, where access to the tip 108 is inhibited, as a normal part of the needle withdrawal motion without the clinician performing additional steps.

The clinician can hold the catheter hub 114 stationary to inhibit the catheter 104 from being withdrawn from the subject as the needle 106 is withdrawn. This can be accomplished, according to one example approach, by holding the catheter hub 114 in position with one hand and pulling the needle assembly 128 away from the catheter hub 114 with the opposite hand. This can be referred to as a two-hand technique. According to another example approach, the clinician withdraws the needle 106 by pulling the needle grip 134 proximally with a middle finger and thumb of one hand. The needle housing 126 can be held stationary with the index finger of the same hand, such as by being placed on the tab 179 of the needle housing 126.

Referring to FIGS. 9a-b, another version of the safety coupling 101 according to a first embodiment of the disclosure is depicted. FIG. 9a depicts the coupling 101 in a ready for use position with the actuator 113 in a distal, engaged position and a catheter hub 114 secured thereto. FIG. 9b depicts the safety coupling 101 as configured when the needle assembly 128 (not shown) is held in the safe position by the needle lock 156 and the actuator 113 is positioned proximally, in the disengaged position.

In this version, the safety coupling 101 is constructed to engage the catheter 104 with an exterior hub contact 117 with a single engagement arm 172 and an interior hub contact 181 formed in the nose 115. Together, the exterior hub contacts 117 and interior hub contacts 181 retain the catheter 104 securely engaged to the catheter insertion device 102 until after the actuator 113 is shifted proximally and needle assembly is in the safe position. The exterior and interior hub contacts 117, 181 can still touch the hub 114 in the safe position. The catheter 104, however, can be freely removed from the catheter insertion device 102, as in the various other example embodiments and versions described herein.

The interior hub contact 181 is formed at the junction between the base 183 of the nose 115 and the hub plate 180. The interior hub contact 181 is shaped and sized to receive a proximal interior portion 185 of the catheter hub 114 in a slip fit type arrangement. This fit can include a taper that is oriented similarly to that of the tapered nose. Alternately, the interior hub contact 181 can lack a taper.

The mounting collar 196 can include a body portion 187 and a mounting plate 189. The mounting plate 189 can be located at a proximal end of the collar 196 and can be received by the distal end 146 of the needle housing 126. The mounting plate 189 can include a central aperture 191 that enables passage of the needle 106. The body portion 187 of the mounting collar 196 can extend between the mounting plate 189 and the hub plate 180 of the nose 115. The catheter hub 114 can abut the hub plate 180, when assembled to the safety coupling 101. The mounting plate 189 can provide a proximal stop for the actuator 113, as discussed herein.

The exterior hub contact 117 can be shaped to promote both catheter 104 retention and separation from the catheter insertion device 102. The exterior hub contact surface 117 of the engagement arm 172 can be angled so that the catheter hub 114 can urge the contact 117 and engagement arm 172 laterally away from the catheter hub 114 as the catheter insertion device 102 moves away from the catheter 104. The single engagement arm 172 can be positioned on an underside of the insertion device 102. In use, the clinician can promote separation of the catheter 104 from the catheter insertion device 102 by moving the proximal end of the insertion device 102 away from the subject. This can place the insertion device 102 and the engagement arm 172 at an angle that pushes the external hub contact away from the catheter hub.

The actuator 113 can be positioned internally to the engagement arm 172 to retain the external and internal hub contacts 117, 181 in cooperative engagement with the catheter 104. In the first, ready for use position (as depicted in FIG. 9a), the actuator 113 lies between the proximal portion 122 of the engagement arm 172 when the actuator 113 is in the distal, engaged. In the second, safe position (as depicted in FIG. 9b), the actuator 113 is shifted proximally, out from in between the engagement arm 172 and other portions of the insertion device, to enable the engagement arm and external hub contact 117 to pivot away from the catheter hub 114. This occurs as the needle transition 166 contacts the needle abutment 163 of the actuator 113 to shift the actuator 113 proximally when the needle assembly 128 is moved to the safe position during needle withdrawal. In some versions, positioning the engagement arm 172 over the actuator 113, can inhibit inadvertent actuator 113 movement that might otherwise enable for catheter 104 release.

The engagement arm 172 can be connected to the nose 115 by a living hinge 193 that enables the distal portion 143 of the engagement arm 172, including the external hub contact 117, to pivot away from the catheter hub 114. The living hinge 193 is constructed so that the distal portion 143 and proximal portion 145 are generally unbiased either toward or away from the catheter hub 114. The external hub contact 117 is engaged to the catheter hub 114 by the actuator 113 in the ready for use position. The distal portion 143 of the engagement arm 172 is moved away from the catheter hub 114 as the catheter 104 is pulled distally away from the catheter insertion device 102, after the actuator 113 has been shifted proximally to the disengaged position. It is to be appreciated that, according to other versions, the engagement arm 172 can be biased toward or away from the catheter hub 114 by a resilient member or other structure.

B. Second Embodiment

Figure 10A:
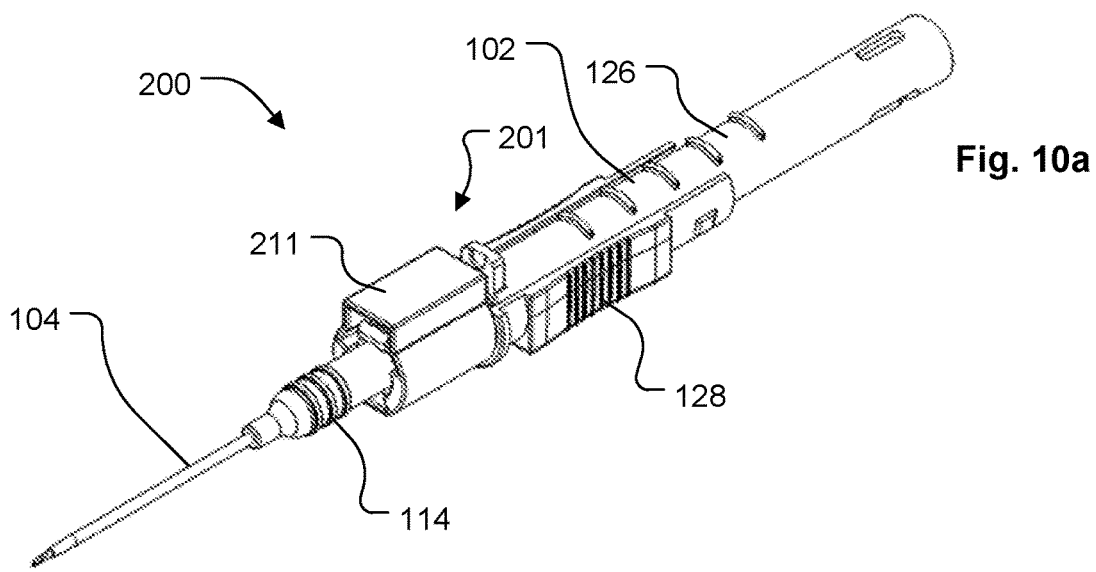
FIG. 10a is a perspective view depicting a safety catheter assembly according to a second embodiment of the disclosure, wherein the safety catheter assembly includes a catheter and a catheter insertion device and is in a first, ready for use position, wherein the catheter is securely connected to the catheter insertion device by a safety coupling including a collar.

Referring to FIGS. 10a-14b, a safety catheter assembly 200 according to a second embodiment of the disclosure is depicted. FIGS. 10a, 10b, and 11a depict the safety catheter assembly 200 in the first, ready for use position. FIGS. 10c and 11b depict the safety catheter assembly 200 in the second, safe position. FIGS. 12a-14b depict various components of the safety catheter assembly 200 in greater detail.

The safety catheter assembly 200 generally includes a safety coupling 201 including a collar 211, an actuator 213, a nose 215, a catheter hub 114, and a needle 106. The collar 211 is positioned about a proximal portion 122 of the catheter hub 114, and a safety coupling 201. The collar 211 is omitted from FIGS. 10b and 10c to provide an improved view of other features. The collar 211 can be positioned about the proximal portion 122 of the catheter hub 114, the engagement arm 220, and the actuator 213. In this respect, the collar 211 can inhibit access to these components or portions thereof.

Figure 10B:
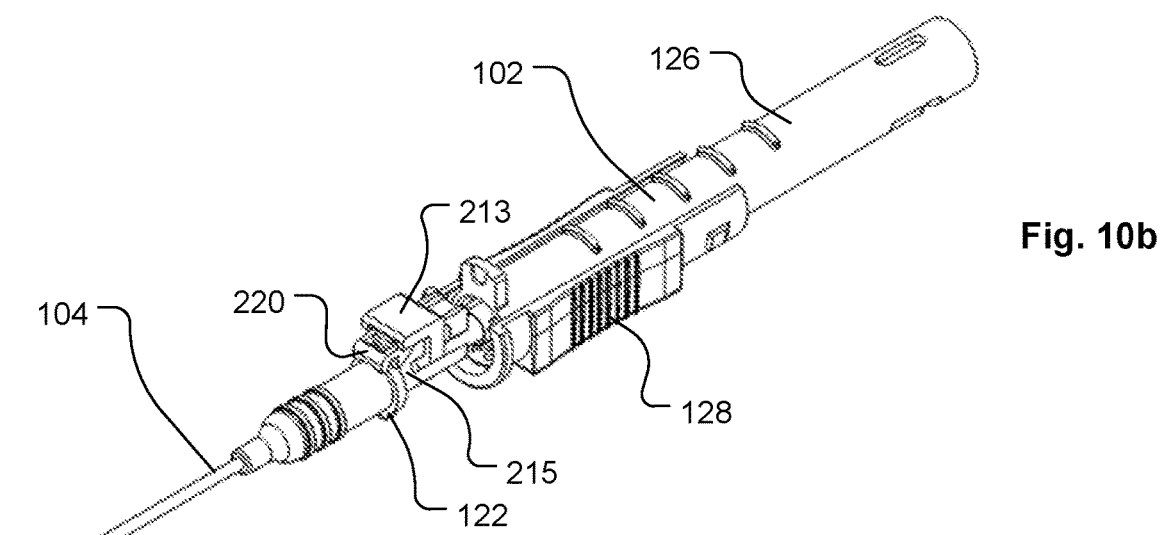
FIG. 10b is a perspective view depicting the safety catheter assembly of FIG. 10a with the collar removed to provide a better view of an actuator and an engagement structure of the safety coupling in the first, ready for use position.
Figure 10C:
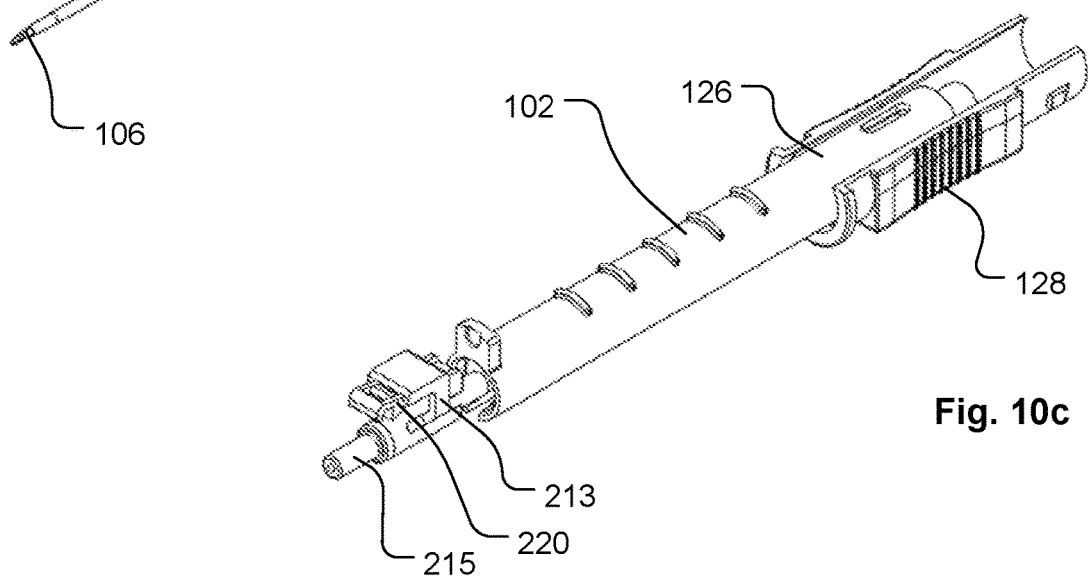
FIG. 10c is a perspective view depicting the catheter insertion device and the safety coupling of FIG. 10b, with the actuator and the engagement structure of the safety coupling in a second, safe position, wherein the catheter (not depicted) is released from the catheter insertion device and a sharp tip of an insertion needle of the catheter insertion device is safely housed within the catheter insertion device.

The safety coupling 201 is constructed to engage the catheter 104 with an engagement structure 222 that includes a single engagement arm 220. The safety coupling 201 generally includes a nose 215, an actuator 213 and an engagement arm 220. The engagement arm 220 includes external hub contacts 217 that cooperate with an interior hub contact 224 formed in the nose 215, as depicted in FIGS. 10b and 11a, wherein the insertion device 102 is in the ready for use position with the actuator 213 shifted to a distal, engaged position. When the needle assembly 128 of the insertion device 102 is in the safe position (as depicted in FIGS. 10c and 11b), the actuator 213 is shifted to a proximal, disengaged position. In the safe position, the exterior hub contacts 217 of the engagement arm 220 are released from engagement with the catheter hub 114, thereby enabling the catheter 104 to be removed from the insertion device 102.

As best depicted in FIGS. 12a and 12b, the collar 211 is a generally unitary structure formed of plastic or another material of sufficient rigidity and generally presents a cylindrical portion 241, a flat portion 242 and a cupola portion 243. The flat portion 242 can be located at the bottom of the cylindrical portion 241, while the cupola portion 243 can extend upwardly from the cylindrical portion.

The cylindrical portion 241 of the collar 211 can generally present a cylindrical outer surface, with nose bushings 244 positioned internally that are dimensioned to receive and support the nose 215 therein, and structured to urge the engagement arm 220 inwardly. The nose bushings 244 can present a curved lead supporting surfaces 245, upper flats 246 and lower flats 247. The flat portion 242 can generally include a lower plate 248 extending between the nose bushings 244. The cupola portion 243 can generally be formed of a cupola roof 249 and two side walls 250. The cupola portion 243 can be sized and shaped to receive the roof portion 254 of the actuator 213 therein. The collar 211 can also present a base portion 239 and a mounting collar 225. The base portion 239 and mounting collar 225 together can define an actuator receiving passage therethrough. The actuator receiving passage 251 can be sized and shaped to receive the actuator 213 therein.

As best depicted in FIGS. 13a-b, the actuator 213 can be a unitary structure formed out of plastic or another suitable material of sufficient rigidity. The actuator 213 can be located within the collar 211, and can be axially shiftable between a distal position (as depicted in FIG. 11a) and a proximal position (as depicted in FIG. 11b). The actuator 213 can include an actuator body 226 and an actuator arm 227. The actuator body 226 can be a substantially cylindrical body that defines an actuator needle passage 228 therethrough and cylindrical surface outside thereof. The body portion 226 of the actuator 213 can be sized and shaped to be received substantially within the nose 215. The needle passage 228 can pass axially through the cylindrical actuator body 226 and can generally present a wide portion 230, a narrow portion 232 and funnel portion 234. The wide portion 230 can be located most distally followed by narrow portion 232 followed by proximally located funnel portion 234. The narrow portion 232 can be sized to fit in close apposition with the needle 106. The wide portion 230 can be sized to receive therein the needle 106 including the needle transition 166 or bump. The narrow portion 232 can be too small to permit the passage of the needle transition 166 at the needle abutment 236 formed therein. Contact of the needle abutment 236 by the needle transition 166 and continued proximal movement of the needle 106 can shift the actuator 213 distally during needle withdrawal. Thus, the needle transition 166 can engage the actuator 213 when the needle 106 is being withdrawn proximally and thereby move the actuator 213 toward the proximal position.

The actuator arm 227 of the actuator 213 can present an arch structure that generally includes an arch support portion 253 and a roof portion 254. The arch support portion 253 can be generally symmetrical in structure and can include a radial support portion 255, a parallel support portion 256 and a distal support portion 257. The radial support portion 255 can be integral with and extend radially outwardly from the cylindrical actuator body 226. The parallel support portions 256 extend generally parallel to one another and outwardly away from the radial support portion 255. A distal support portion 257 extends substantially perpendicular to the parallel support portion 256 in a generally distal direction.

A roof plate 258 of the actuator 213 can extend generally from the distal support portion 257 and present a rounded distal edge 260 and a rounded proximal edge 261. The roof plate 258 can include an external portion that can present a nose engaging portion 262 at a distal and inwardly facing portion 263. The nose engaging portion 262 can present distal flat face 264 and proximal curved face 265. The proximal curved face 265 can extend proximally and also inwardly.

The nose 215 can be located within the collar 211 and partially surround a portion of the actuator 213. The nose 215 can have an engagement arm 220 that is shiftable between a catheter hub engaged position (as depicted in FIG. 11a), wherein the catheter hub 114 is inhibited from removal from the collar 211, and a catheter hub disengaged position (as depicted in FIG. 11b), wherein the catheter hub 114 is removable from the collar 211. The engagement arm 220 can be resiliently biased toward the catheter hub disengaged position. The engagement arm 220 can be shifted to the catheter hub engaged position when the actuator 213 is in the distal position, and can be resiliently shifted to the catheter hub disengaged position when the actuator 213 is in the proximal position. The catheter hub 114 can be engageable at least partially within the collar 211 and at least partially over the nose 215. The catheter hub 114 can be axially removable from the collar 211 when the engagement arm 220 is in the catheter hub disengaged position.

As best depicted in FIGS. 14a-b, the engagement structure 222 can generally be a unitary structure and present a distal nose 215, a cylindrical body 280, a radial engagement arm support 266 and an engagement arm 220. The distal nose 215 can extend generally distally from a cylindrical body 280. The distal nose 215 can be substantially cylindrical in external structure and of a smaller diameter than the cylindrical body 280. The engagement arm 220 can be integrally formed and coupled to the cylindrical body 280 at a proximal end thereof. The engagement arm 220 can be supported by and integrally coupled to an engagement arm support 266. The distal nose 215, cylindrical body 280, engagement arm support 266 and engagement arm 220 can be integrally formed of a plastic or other material of sufficient rigidity and resiliency. The engagement arm 220 can be biased to an outward orientation, away from the catheter hub 114.

The distal nose 215 can be generally cylindrical and sized to be received in the catheter hub 114. The distal nose 215 can define a needle passage 281 therethrough that is sufficiently large so that the needle 106 including the needle transition 166 can pass completely therethrough relatively unimpeded. The cylindrical body 280 can be divided into a larger portion 267 and a smaller portion 268 by two radial support receiving slots 269. The larger portion 267 can support the engagement arm support 266 that in turn supports the engagement arm 220.

The engagement structure 222 generally includes a finger portion 270, a thumb portion 271 and a wrist portion 274. The finger portion 270 can be coupled to the thumb portion 271 by hand bars 272 and can define external hub engagement surfaces 217 configured to contact and engage the catheter hub 114, thereby engaging the catheter hub 114 to the safety coupling 201. The hand bars 272 can generally include two parallel structures extending between the thumb portion 271 and the finger portion 270. The finger portion 270, the thumb portion 271 and the hand bars 272 together can define a hand gap 275. The hand gap 275 closely conforms to the catheter hub 114, such that when the catheter hub 114 is engaged in the hand gap 275 the catheter hub 114 is inhibited from removal. The wrist bars 276 can generally include two parallel spaced apart structures extending between the hand support and the thumb portion 271. The hand support, the thumb portion 271 and the two wrist bars 276 can together surround and define the wrist gap. The wrist bars 276 can be resilient, and can be biased to assume an outward resting position as depicted in FIGS. 10c and 11b. Wrist bars 276 can be flexible, and can be flexed to assume the position depicted in FIGS. 10b and 11a. The finger portion 270 can extend generally downwardly from hand bars 272. Finger portion 270 presents a curved knuckle portion 273.

The thumb portion 271 can have a generally triangular section and extend downwardly a greater distance than the finger portion 270 relative to the hand bars 272. The finger portion 270, the thumb portion 271 and the hand bars 272 can generally define a rib or lug receiving space 277 therebetween. The lug receiving space 277 can be open at a downward side thereof and can be sized to receive lugs of catheter hub 114 therein. In some versions, the lugs can include ribs or luer threads. The thumb portion 271 can generally include two triangular portions and a thumb cross member. The thumb cross member can extend from the triangular portion.

In operation, actuator 213 can be secured to the distal end of safety catheter assembly 200 and the nose 215 can be secured to the collar 211 by mechanical or adhesive coupling. Prior to securing the nose 215, the actuator 213 can be inserted so that the cylindrical body 280 is received within the nose. The radial support portions 266 can extend outwardly from the nose 215 radially through the radial support receiving slots 269. Accordingly, the actuator 213 can be slidably movable within nose 215 and collar 211. The actuator can slidably shift between the distal, engagement position (as depicted in FIGS. 10a, 10b, and 11a), and the proximal, disengaged position (as depicted in FIGS. 10c and 11b). When the actuator is in the distal, engaged position, the external hub contact surfaces 217 are moved toward the distal nose 215, thereby gripping the lugs 149 or other portions of the catheter hub 114. Thus, catheter hub 114 is engaged to collar 211 and nose 215.

C. Third Embodiment

Referring to FIGS. 15a-25b, a safety catheter assembly 300 according to a third embodiment of the disclosure is depicted. FIGS. 15a-18b depict a first version of the safety catheter assembly 300, FIGS. 19-22 depict a second version of the safety catheter assembly 400, and FIGS. 23-25b depict a third version of the safety catheter assembly 500.

Figures 15A, 15B, 15C:
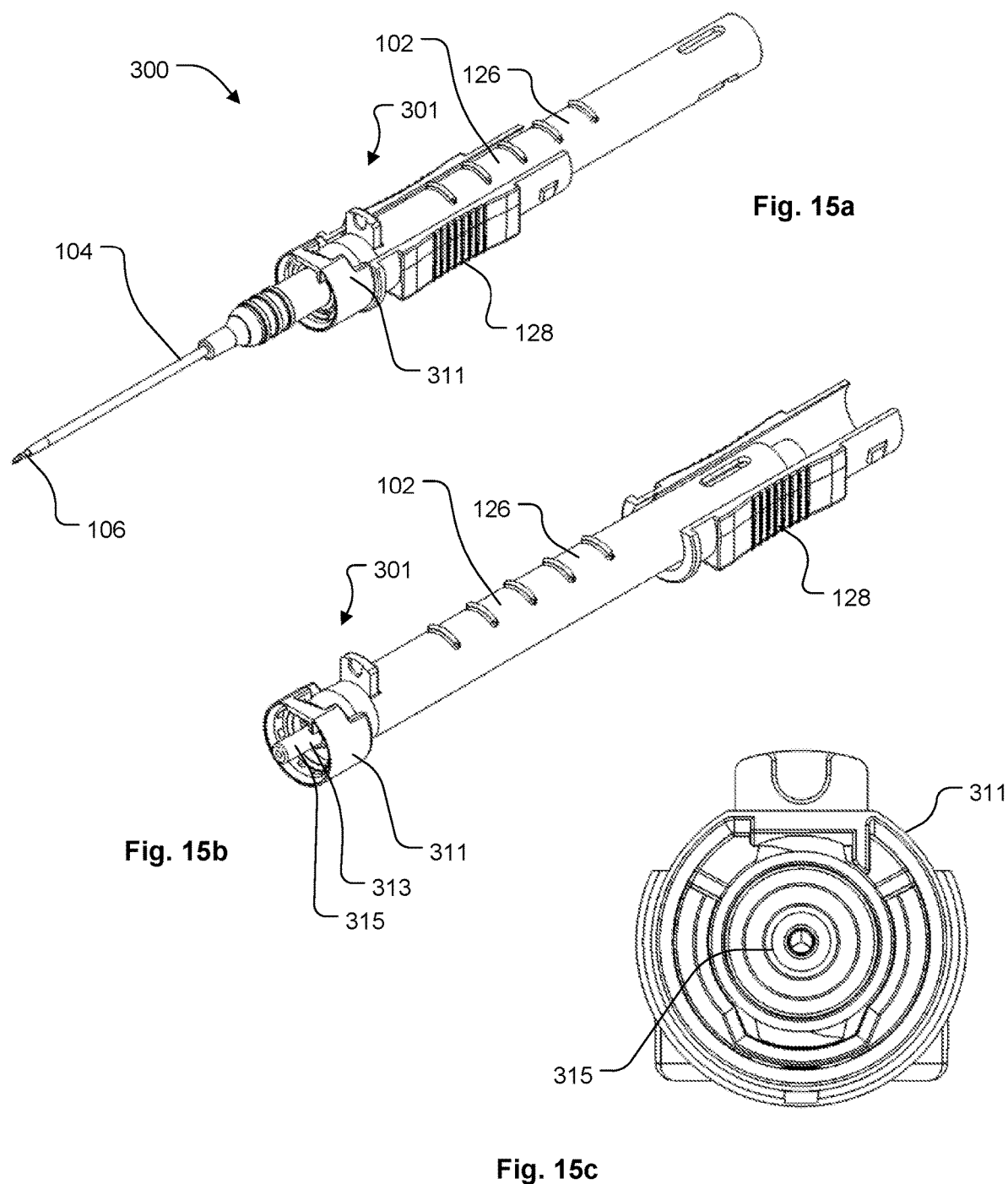
FIG. 15a is a perspective view depicting a safety catheter assembly according to a third embodiment of the disclosure, wherein the safety catheter assembly includes a catheter and a catheter insertion device and is in a first, ready for use position, wherein the catheter is securely connected to the catheter insertion device by a safety coupling.
FIG. 15b is a perspective view depicting the catheter insertion device and safety coupling of FIG. 15a in a second, safe position, wherein the catheter (not depicted) is released from the catheter insertion device and a sharp tip of an insertion needle of the catheter insertion device is safely housed within the catheter insertion device.
FIG. 15c is a distal end view depicting the catheter insertion device and safety coupling of FIG. 15b.

Referring to FIGS. 15a-18b, the safety catheter assembly 300 is shiftable between a first, ready for use position and a second, safe position. Safety catheter assembly 300 generally includes a retainer 326 and a collar 311. The retainer 326 can be received within the collar 311, and can include an actuator 313 and a nose 315, such that the actuator 313 and the nose 315 can form a unitary structure. The retainer 326 and the collar 311 can be shaped and sized such that a catheter hub 114 is receivable at least partially within the collar 311 and at least partially over the nose 315. The actuator 313 can be shiftable between a distal, engaged ready for use position (as depicted in FIGS. 15a and 16a), wherein the collar 311 can receives a proximal end 122 of the catheter hub 114 therein, and the nose 315 can engage to an interior of the catheter hub 114, and a proximal, disengaged safe position (as depicted in 15b and 16b), wherein the catheter hub 114 is releasable from the collar 311 and the retainer 326. FIG. 15c depicts a distal end view of the safety coupling 301 with the catheter removed. FIGS. 17a-18b depict individual components of the safety catheter assembly 300 in greater detail.

The safety catheter assembly 300 generally includes a collar 311 that lies about the periphery of the proximal end 122 of the catheter hub 114. The safety catheter assembly 300 further includes a nose 315, an actuator 313 and an engagement structure 322 that can be formed from a common, unitary component that is referred to as a retainer 326. The nose 315 and engagement structure 322 can move together with the actuator 313 as the actuator 313 is shifted proximally to the disengaged position.

The collar 311 can be operably coupled to the distal end 146 of needle housing 126 of the safety catheter assembly 300, for example by adhesives, a mechanical connection, or other means. The retainer 326 can be slideably engaged within the collar 311 and shiftable between a distal engaged position and a proximal disengaged position, as the actuator 313 is shifted proximally by proximal movement of the needle 106. The collar 311 can include one or more external hub contacts 317 that contact the catheter hub 114 when secured to the safety coupling 301. The external hub contacts 317 may also be referred to as exterior hub contacts 317. The nose 315 can include one or more interior hub contacts 324. One or more external hub contacts 317 can also be provided by an engagement structure 322 of the retainer 326 and cooperate with the interior hub contacts 324 of the nose 315 and the exterior or external hub contacts 317 of the collar 311 to securely engage the catheter hub 114 to the safety coupling 301 when the actuator 313 is in the distal engaged position.

The interior hub contacts 324 can engage to the interior of the catheter hub 114 when the actuator 313 is in the distal, engaged ready for use position, such that a distal end of the nose 315 is proximate to a distal end of an interior space of the catheter hub 114, thereby inhibiting separation of the catheter hub 114 from the collar 311 and the retainer 326. The nose 315 can extend distally from the actuator 313. The nose 315 can be structured to sheath the needle tip 108 when the needle tip 108 is retracted to the second, safe position. When the nose 315 is in the distal, engaged ready for use position, the length of the nose 315 that extends within the interior of the catheter hub 114 can be at least twice a diameter of the nose 315. The interior of the catheter hub 114 can be resilient to facilitate disengagement of the catheter hub 114 from the nose 315.

Figure 16A:
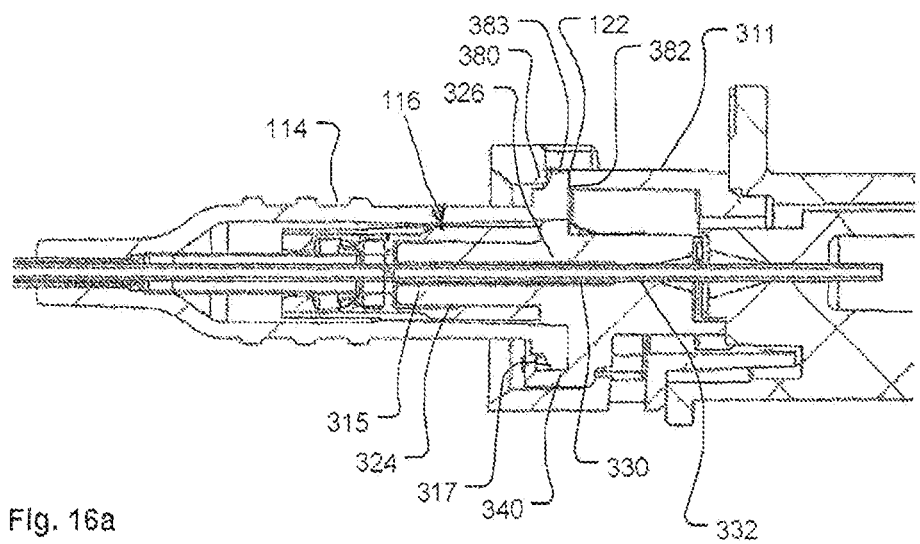
FIG. 16a is a fragmentary cross sectional view depicting a safety catheter assembly according to a third embodiment of the disclosure in a first, ready for use position, wherein safety catheter assembly includes a safety coupling having a retainer and a collar positioned relative to one another so as to engage a catheter of the safety catheter assembly.
Figure 16B:
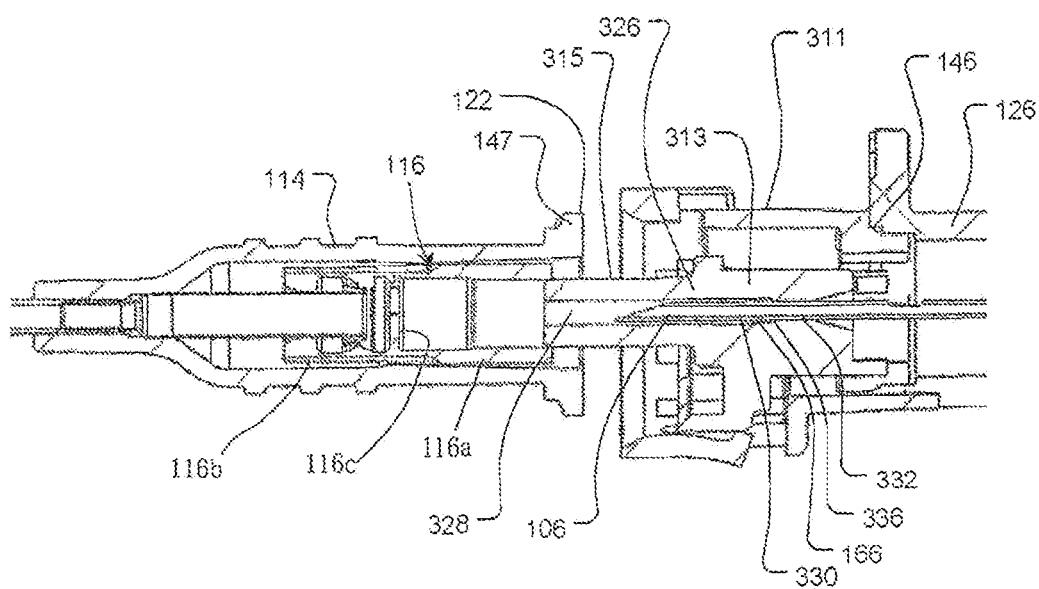
FIG. 16b is a fragmentary cross sectional view depicting the safety catheter assembly of FIG. 11a in a second, safe position, wherein the retainer has been shifted proximally thereby releasing the catheter from the safety coupling.

As best depicted in FIGS. 15b and 16b, the safety coupling 301 can be configured in a safe position with actuator 313 and other portions of the retainer 326 shifted to the proximal, disengaged position. Shifting of the actuator 313 and other portions of the retainer 326 can occur after the needle assembly 128 reaches the safe position. In the safe position, the interior hub contacts 324 of the nose portion 315 can be disengaged from the catheter hub 114. The exterior hub contacts 317 on a partially annular wall 340 of the retainer 326 can also be disengaged from the catheter, thereby creating a space within catheter hub 114 because the interior hub contacts on the base 342 of the nose 315 are retracted and only the distal portion of the nose 315, which is of a smaller diameter, is within catheter hub 114. When in the safe position, the exterior hub contacts 317 of the collar 311 and the retainer 326 and the interior hub contacts 324 of the nose 315 are disengaged from the catheter hub 114 to enable the catheter 104 to be released. The exterior hub contacts 317 and interior hub contacts 324 can remain in contact with the catheter hub 114, after disengagement. In some versions, the needle housing 126 includes the needle lock 156 configured to interlock the needle assembly 128 to the needle housing 126 in the proximal, disengaged safe position.

Figure 17A:
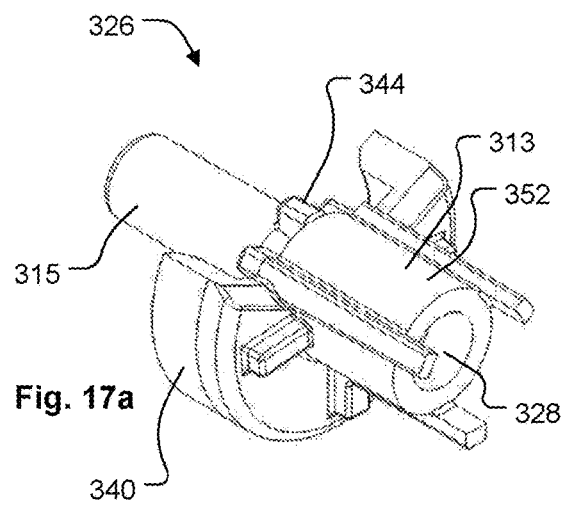
FIG. 17a is a proximal perspective view depicting a retainer of a safety coupling according to a third embodiment of the disclosure.
Figure 17B:
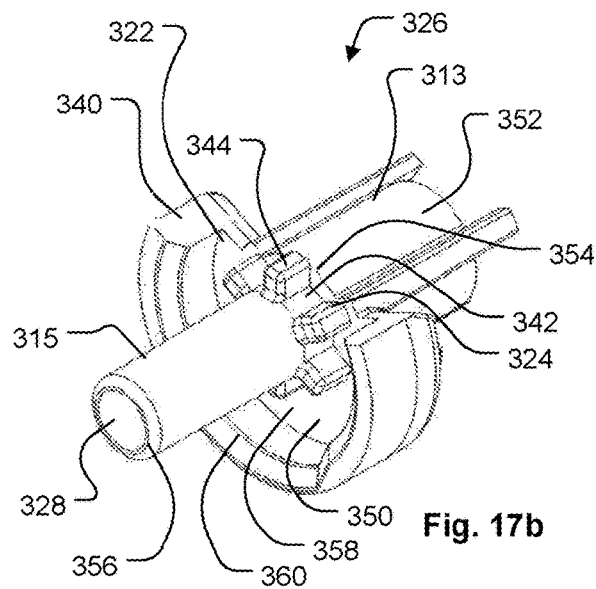

As best depicted in FIGS. 17a to 17b, the retainer 326 can be separated from the other components of the safety catheter assembly 300. The retainer 326 can generally be a unitary structure that includes various features, including an actuator 313, a nose 315, and various hub engagement structures. The hub engagement structures can include a base structure 342 on the nose 315 defined by protrusions 344 providing one or more interior hub contact surfaces 324, and a partially annular wall 340 providing one or more surfaces of external hub contact 317. The retainer 326 can also include a partially annular plate 350 that contacts the proximal end 122 of the hub 114 in the engaged position. The actuator portion 313 of the retainer 326 can be formed, in part, by a proximal extension 352 that forms at least a portion of the nose 315 of the retainer 326. In one version, the retainer 326 is formed from plastic or another material of suitable rigidity.

The nose 315 of the retainer 326 can extend distally outward and generally perpendicular to the partially annular plate 350. The nose 315 can include a base structure 342 that is present at the proximal end 354 of the nose 315 and that is defined by multiple protrusions 344. The extension collar 311 can be larger in diameter or cross sectional extent than nose 315. In one version, the nose 315 can be substantially cylindrical. The protrusions 344 that define the base 342 can provide interior hub contacts 324 at their radially outermost side. The interior hub contacts 324 of the protrusions 344 can be shaped and sized to contact corresponding internal hub surfaces. The distal portion 356 of the nose 315 can be sized to be significantly smaller than an interior of the catheter hub 114. In the engaged position, the distal portion 356 can contact a blood control valve 116. The contact between the distal portion 356 and the blood control valve 116 can provide a seal that helps contain flashback blood. As shown in FIG. 16a, the nose 315 is inserted into the blood control valve 116. A needle passage 328 can pass axially through the nose portion 315, base 342, the partially annular plate 350, and the proximal extension 352. The partially annular wall 340, the partially annular plate 350 and the base structure 342 can together border and define a hub flange space 358 providing one or more exterior hub contacts 317. The hub flange space 358 can be sized and shaped to receive a flange 147 of the catheter hub 114 and include a rib recess 360 that receives a rib or lug 149 of a catheter hub 114, such as a luer thread. The catheter hub 114 also can present flange lugs. The proximal extension can be substantially cylindrical in structure and sized to be received within the collar 311 in slideable apposition. FIG. 16b shows the nose 315 being removed from the blood control valve 116.

The exterior hub contacts 317 can be configured as an arcuate partial wall that engages the proximal end 122 of the catheter hub 114 when the actuator 313 is in the distal, engaged ready for use position, thereby inhibiting separation of the catheter hub 114 from the collar 311 and the retainer 326. The arcuate partial wall further can defines a hub flange space 358 into which a flange of the catheter hub is receivable. The collar 311 and the retainer 326 can be configured to engage opposing surfaces of the proximal end 122 of the catheter hub 114. The collar 311 can include a step feature 366 that engages the proximal end 122 of the catheter hub 114.

As best depicted in FIGS. 16a and 16b, the needle passage 328 for collar 311 can include a wider portion 330 and a narrower portion 332. The wider portion 330 can be distal to the narrower portion 332. The wider portion 330 can be sized so that the needle 106, including the needle transition 166 or bump can be received therein. The narrower portion 332 can be sized to closely approximate the size of the needle 106 without the needle transition 166. Accordingly, the needle transition 166 will contact a needle abutment 336 at the juncture of the wider 330 and narrower portions 332 to inhibit further passage of the needle 106. Contact between the needle transition 166 and the needle abutment 336 enables proximal movement of the needle to shift the actuator 315 and other portions of the retainer 326 proximally, to the disengaged position.

Figure 18A:
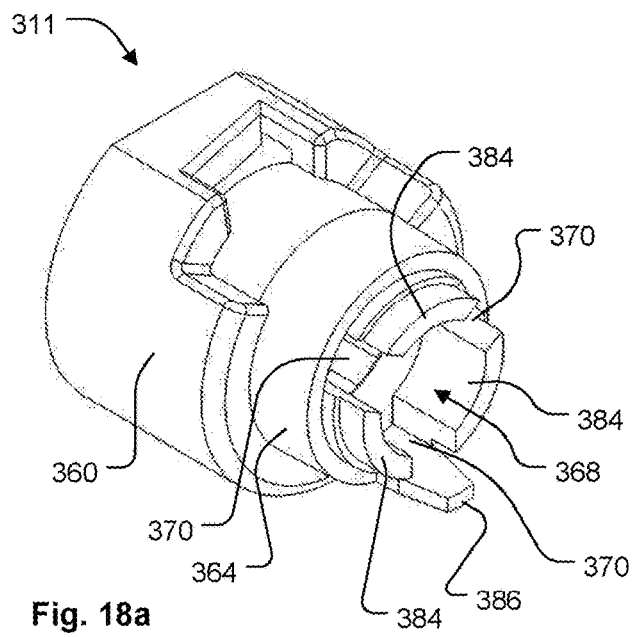
FIG. 18a is a proximal perspective view depicting a collar of a safety coupling according to a third embodiment of the disclosure.
Figure 18B:
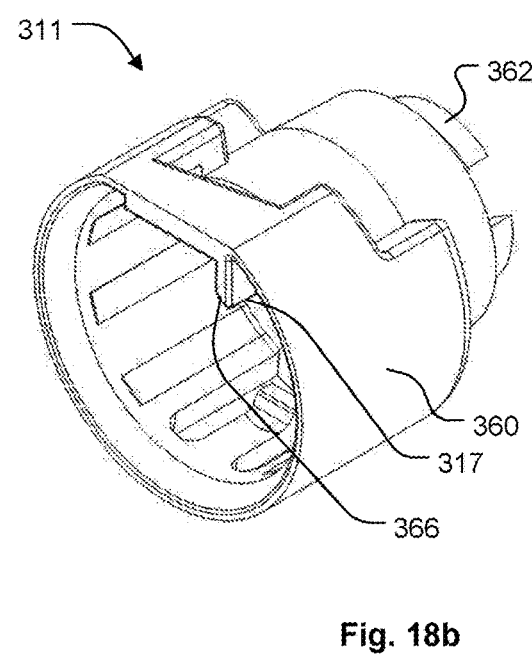
Figure 23:
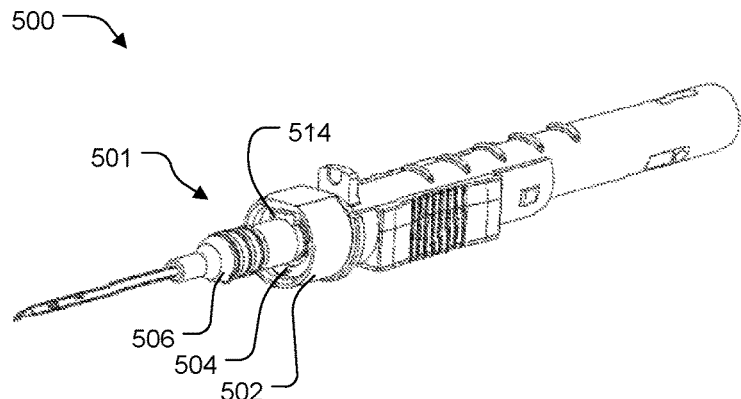
FIG. 23 is a perspective view depicting a third version of a safety catheter assembly according to a third embodiment of the disclosure, wherein the safety catheter assembly includes a catheter and a catheter insertion device and is in a first, ready for use position, wherein the catheter is securely connected to the catheter insertion device by a safety coupling.

As best depicted in FIGS. 18a and 18b, the collar generally presents an external collar wall 360, a proximal collar portion 362, a collar plate 364 and a step feature 366. The proximal collar portion 362 can be sized and structured to be secured to safety catheter assembly 300 at a distal end 146 of the needle housing 126. The collar plate 364 can join the external collar wall 360 and the step feature 366 to the proximal collar portion 362.

The external collar wall 360 can be substantially cylindrical in structure and can include a step feature 366 therein. The external collar wall 360 can be sized to receive the partially annular wall 340 therein. A proximal collar portion 362 and a collar plate 364 can together border and define a retainer passage 368 shaped and sized to receive the proximal extension 352 slideably therein, as well as define ridge receiving grooves 370.

The step feature 366 can include a distal hook 380 and a proximal stop 382. The distal hook 380 and the proximal stop 382 can extend generally inwardly. The distal hook 380 can be located distally. The proximal stop 382 can be located proximally to the distal hook 380 and separated therefrom by hub receiving space 383. Hub receiving space 383 can be sized and shaped to receive a portion of flange 147 therein. The proximal collar portion 362 can present three wall portions 384 and a proximally extending key 386.

When the actuator 313 is in the distal, engaged ready for use position, a longitudinal axis of the needle assembly 128 and a longitudinal axis of the catheter hub 114 can be substantially coaxial or parallel. When actuator 313 is in the proximal, disengaged safe position, the catheter hub 114 can be disengageable from the retainer 326 and the collar 311 by angular rotation of the of the catheter hub 114 relative to the needle assembly 128, such that the longitudinal axis of the catheter hub 114 is not aligned with the longitudinal axis of the needle assembly 128.

Referring to FIGS. 19-22, another version of the safety catheter assembly 400 according to a third embodiment of the disclosure is depicted. In this version, the safety catheter assembly 400 operates in a way similar to the version depicted in FIGS. 15a-18b. FIG. 19 depicts the safety catheter assembly 400 in the ready for use position, wherein the sheath and end cap are omitted to provide a view of other features. FIG. 20 depicts a flangeless collar 402, FIGS. 21a-b depict a flangeless retainer 404, and FIG. 22 depicts a flangeless hub 406.

In the ready for use position shown, the catheter 104 is securely connected to the catheter insertion device 102 by a safety coupling 401. When assembled, the flangeless hub 406 can be engaged to the safety catheter assembly 400 by the flangeless collar 402 and the flangeless retainer 404. The flangeless retainer 404 can be positioned inside of the flangeless collar 402. The flangeless hub 406 can be positioned over an extension 408 and an extension collar 410. A step feature 412 can engage to a proximal end 414 of flangeless hub 406 in a friction interference fit between the step feature 412 and the smooth exterior 446 of proximal end 414, where exterior hub contacts 416 are positioned. Following catheter insertion and withdrawal of the needle 106, the flangeless collar 402 can be withdrawn proximally thus permitting flangeless hub 406 to be separated from flangeless retainer 404.

As best depicted in FIG. 20, the flangeless collar 402 can be a generally unitary structure, formed from plastic or another material of suitable rigidity. The flangeless collar 402 can generally present an external collar wall 418, a proximal collar portion 420, a collar plate 422 and a step feature 412. The proximal collar portion 420 can be sized and structured to be secured to safety catheter assembly 400. The collar plate 422 can be substantially circular in structure and can join the external collar wall 418 to the proximal collar portion 420. The step feature 412 can be secured to the external collar wall 418 and can extend inwardly from the collar wall 418. The step feature 412 can be structured to frictionally engage the flangeless hub 406 and provides exterior hub contacts 416 at these points. The external collar wall 418 can be generally continuous and circular. The external collar wall 418 and the collar plate 422 together can generally define a retainer cavity 421. The retainer cavity 421 can be sized and shaped to receive flangeless retainer 404 slidably therein. The proximal collar portion 420 can present proximal extension ridges 424 and proximal wall portions 426. The proximal wall portions 426 can be interrupted by proximal gaps 428.

The safety catheter assembly 400 can include structure that engages the flangeless retainer 404 with the flangeless collar 402 in a rotationally fixed manner while enabling axial movement. For example, the flangeless retainer 404 can include one or more proximal extensions 434 and the flangeless collar 402 can include a proximal wall portion 426 defining one or more proximal gaps 428 therein.

As best depicted in FIGS. 21a and 21b, the flangeless retainer 404 can generally present an extension 408, an extension collar 410, an annular wall 430, an annular plate 432, and a proximal extension 434. The extension 408 can extend distally outward and can be surrounded at its base 436 by extension collar 410. The extension 408 and extension collar 410 can extend distally from the annular plate 432. The annular wall 430 can extend distally from the perimeter from annular plate 432. The proximal extension 434 can extend proximally from annular plate 432 on a side opposing extension 408 that defines a needle passage 440 therethrough. Annular plate 432, annular wall 430, extension collar 410 and extension 432 together can define a hub space 442. The hub space 442 can be sized and shaped to receive flangeless hub 406 therein.

As best depicted in FIG. 22, flangeless hub 406 can generally present distal end 444 and proximal end 414. Distal end 444 can be joined to a catheter tube 112 (not depicted in FIG. 22). Proximal end 414 can present a smooth exterior 446. In one version, flangeless hub 406 presents no flange, ears or lugs.

Figure 26:
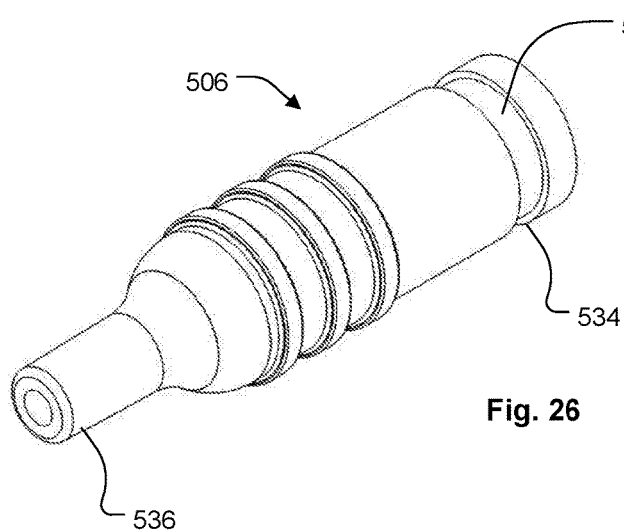
FIG. 26 is a perspective view depicting a grooved catheter hub of the catheter depicted in FIG. 23.
Figure 24:
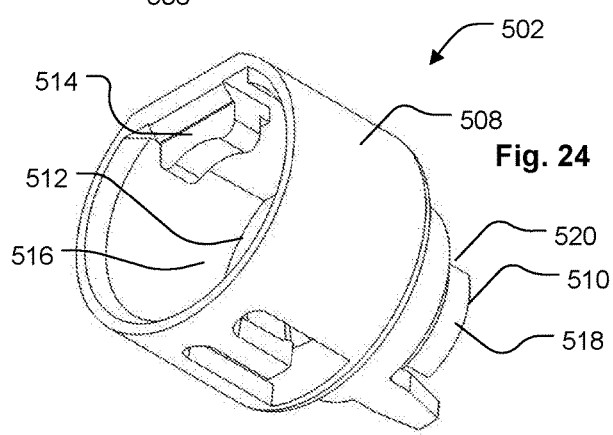
FIG. 24 is a distal perspective view depicting a grooved collar of the safety coupling depicted in FIG. 23.

Referring to FIGS. 23-26, another version of the safety catheter assembly 500 according to a third embodiment of the disclosure is depicted. In this version, safety catheter assembly 500 generally includes grooved collar 502, grooved retainer 504 and grooved hub 506, in addition to other structures previously described. FIG. 24 depicts grooved collar 502. FIGS. 25a-b depict grooved retainer 504, and FIG. 26 depicts grooved hub 506.

As best depicted in FIG. 24, grooved collar 502 generally presents external collar wall 508, proximal collar portion 510, collar plate 512 and step feature 514. External collar wall 508 can extend generally distally from collar plate 512. External collar wall 508 can support step feature 514. Collar plate 512, external collar wall 508 and step feature 514 can generally define retainer cavity 516. The proximal collar portion 510 can generally include proximal wall portions 518, which can be separated by proximal gaps 520.

Figure 25A:
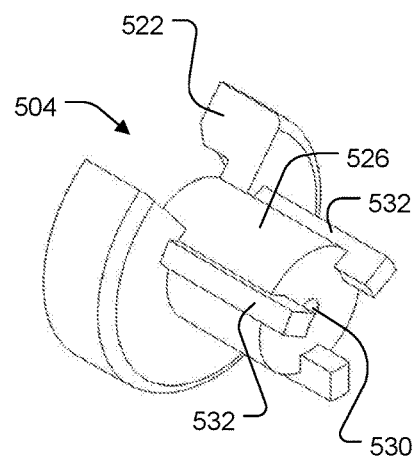
FIG. 25a is a distal perspective view depicting a grooved retainer of the safety coupling depicted in FIG. 23.
Figure 25B:
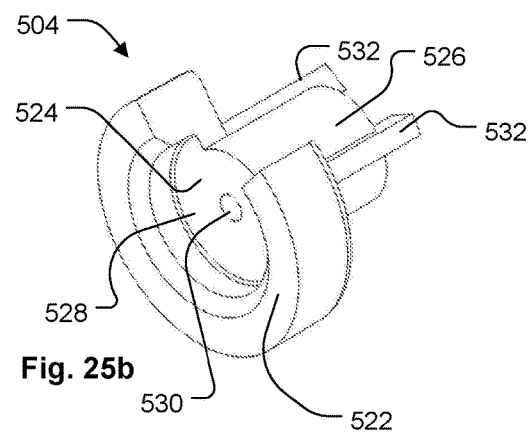

As best depicted in FIGS. 25a-b, grooved retainer 504 can present partially annular wall 522, partially annular plate 524 and proximal extension 526. Grooved retainer 504 can lack an extension and an extension collar. Partially annular wall 522 can extend distally from partially annular plate 524. Proximal extension 526 can extend proximally from partially annular plate 524. Together partially annular wall 522 and partially annular plate 524 can define hub space 528.

The partially annular plate 524 and the proximal extension 526 define a cannula passage 530 therethrough. The partially annular wall 522 and the partially annular plate 524 together can surround and define the hub space 528 sized to receive grooved hub therein. In one version, the proximal extension 526 can further present proximal extension ridges 532 extending peripherally and proximally therefrom.

As best depicted in FIG. 26, the grooved hub 506 generally presents proximal end 534 and distal end 536. Grooved hub 506 can have a generally similar form other disclosed catheter hubs 114. For instance, the distal end 120 can be engaged to a catheter tube 112, but unlike other disclosed catheter hubs, the proximal end 122 can lack a flange 147 and can present a slightly indented circumferential groove. In one version, grooved retainer 504 can be positioned within grooved collar 502. Grooved hub 506 can be engaged to grooved retainer 504 and grooved collar 502. Step feature 514 can be engaged into circumferential groove 538.

In operation, safety catheter assembly 500 including safety coupling 501 can be supplied in an assembled state with grooved hub 506 secured within grooved collar 502 so that the distal end 535 of grooved catheter hub 506 is received into the hub space 530. In addition, grooved retainer 504 can be advanced in a distal direction to a distal engaged orientation. In the assembled state, needle 106 and needle bump 166 can reside within catheter 104.

After insertion of the catheter 104 and upon withdrawal of the needle 106 from the catheter 104, the grooved collar 502 can be withdrawn proximally thus disengaging the step feature 514 from the circumferential groove 538. Pulling the grooved retainer 504 back while simultaneously removing the grooved hub 506 releases the grooved hub 506 because interference between the grooved hub 506 and the grooved collar 502 alone is much less than between the grooved hub 506 with the grooved collar 502 and the grooved retainer 504 together. The grooved hub 506 can then be separated from the grooved retainer 504 while the needle 106 remains withdrawn.

D. Fourth Embodiment

Referring to FIGS. 27a-33b, a safety catheter assembly 600 according to a fourth embodiment of the disclosure is depicted. FIGS. 27a, 27b, 28a and 29b depict the safety catheter assembly 600 in a ready for use position, with an actuator 604 shifted distally in an engaged position. The catheter 104 is omitted from FIG. 27b to provide a view of other features of the safety coupling 601. FIGS. 27c, 28b, and 29b depict the safety catheter assembly 600 in a safe position with the actuator 604 shifted proximally, to a disengaged position. FIGS. 31a to 32b depict the various components of the safety catheter assembly 600 in greater detail.

The safety catheter assembly 600 generally includes a catheter 104 and a safety catheter insertion device 102. The catheter 104 has a catheter hub 114 and a catheter tube 112. The safety catheter insertion device 102 is selectively connectable to the catheter hub 114 and includes a needle housing 126, needle assembly 128, and a safety coupling 601. The safety coupling 601, generally includes a mounting collar 606, a nose 608, an actuator 604 and an engagement structure 610. The mounting collar 606, the nose 608, the actuator 604, and the engagement structure 610 can be, however, constructed differently than in other example embodiments of the disclosure. For example, the nose 608 and the actuator 604 can be formed from a common unitary structure. Additionally, the engagement structure 610 can be formed from a unitary structure that is separate from the nose 608 and the actuator 604, and can be constructed to engage the catheter 104 with a "C" shaped engagement structure 610 that flexes from a closed configuration to an open configuration.

Figure 27A:
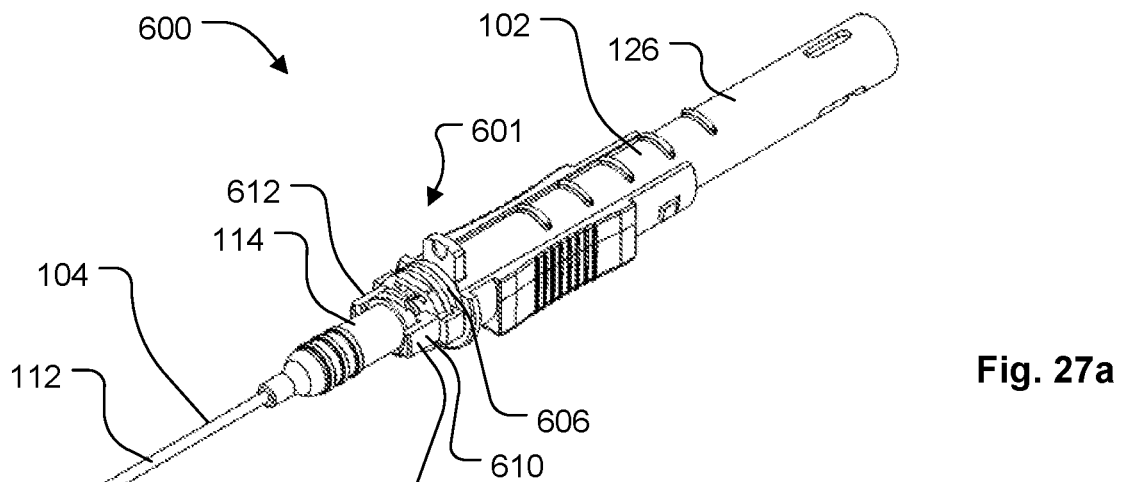
FIG. 27a is a perspective view depicting a safety catheter assembly according to a fourth embodiment of the disclosure, wherein the safety catheter assembly includes a catheter and a catheter insertion device and is in a first, ready for use position, and wherein the catheter is securely connected to the catheter insertion device by a safety coupling.

As best depicted in FIGS. 27a and 28a, the safety catheter assembly 600 can include a safety coupling 601 that is supplied in an assembled state with the catheter hub 114 secured to the insertion device 102 with the engagement arms 612 of the engagement structure 610. A portion of the rim or flange 614 of the catheter hub 114 can be contacted by external hub contacts 616 and engaged in the respective hub flange space 618 of each engagement arm 612 thereby retaining the catheter 104 to the insertion device 102 in the ready for use position with the nose 608 and actuator 604 shifted distally, in the engaged position. The distal portion 620 of the nose 608 can be received within catheter hub 114 and can define internal hub contacts 622 that cooperate with the external hub contacts 616 of the engagement arms 612 to retain the catheter 104 to the catheter insertion device 102. The needle 106 can be provided in the distally advanced, ready for use position so that needle transition 166 is within the catheter tube 112.

As best depicted in FIG. 28b, the actuator 604 can be shifted proximally to the disengaged position to enable the catheter 104 to be separated from the safety coupling 601 of the catheter insertion device 102. The actuator 604 can be shifted proximally with proximal movement of the needle assembly 128 associated with needle 106 withdrawal. The needle transition 166 can be moved proximally through the aperture 624 of the actuator 604 until the needle transition 166 encounters the needle abutment 626. The actuator 604 and the nose 608 can then be drawn proximally along with the needle 106. This proximal shifting moves the internal and external hub contacts 622 and 616 out of engagement with the catheter hub 114, enabling catheter 104 removal from the safety coupling 601 and insertion device 102. The internal hub contacts 622 of the nose 608 can be moved out of engagement as the nose 608 shifts proximally with the actuator 604 to the proximal, disengaged position. The proximal shifting of the actuator 604 can also urge a ramped, frustoconical portion 628 of the actuator 604 into the aperture 630 of the engagement structure 610. This movement can cause deformation of the "C" shaped engagement structure 610, urging engagement arms 612 open into an expanded position. In the expanded position, external hub contacts 616 of the engagement arms 612 can be disengaged from catheter hub 114.

Figure 27B:
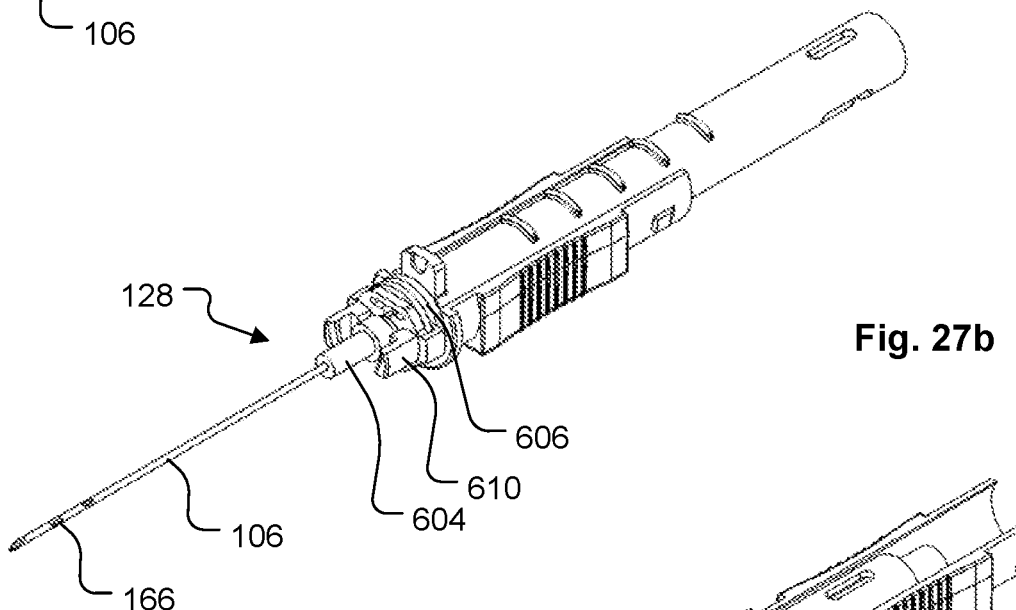
FIG. 27b is a perspective view depicting the catheter insertion device of FIG. 27a without the catheter to provide a better view of the safety coupling in the first, ready for use position.
Figure 27C:
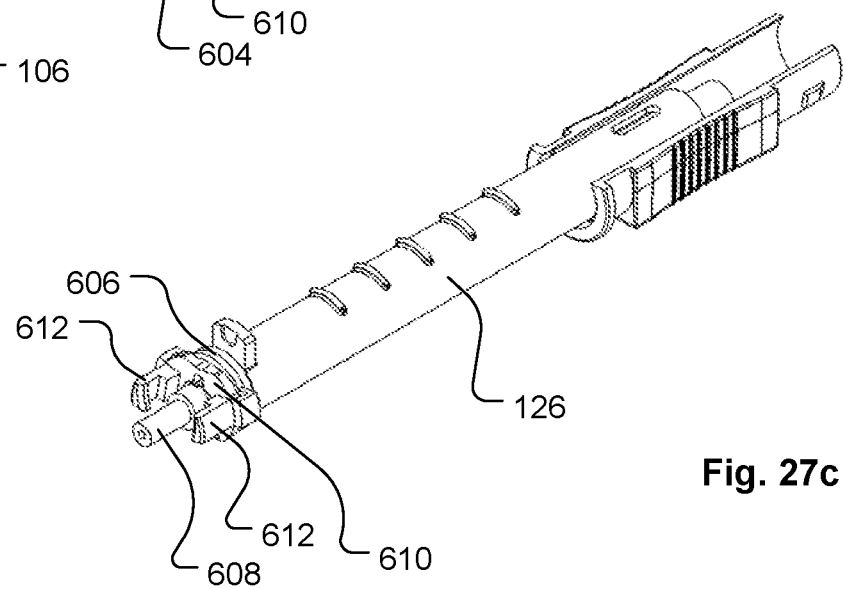
FIG. 27c is a perspective view depicting the catheter insertion device of FIG. 27b, with the safety coupling in a second, safe position, wherein a sharp tip of an insertion needle of the catheter insertion device is safely housed within the catheter insertion device.
Figure 30A:
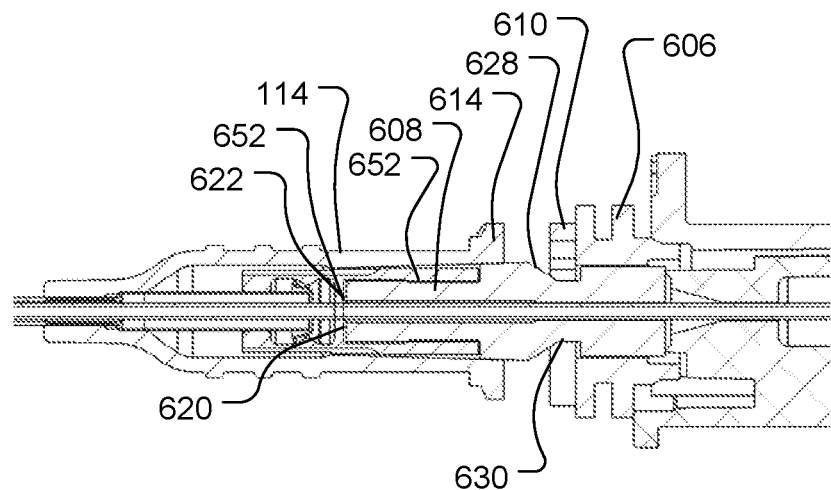
FIG. 30a is a fragmentary, cross sectional view depicting an alternative version of a safety coupling according to a fourth embodiment of the disclosure in a first, ready for use position, wherein the catheter is securely connected to the needle housing by the safety coupling.
Figure 30B:
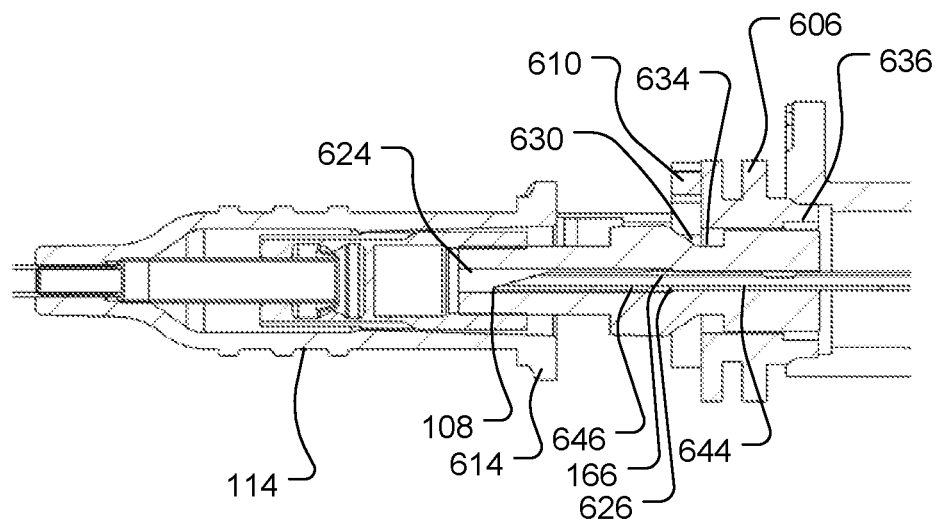
FIG. 30b is a cross sectional view depicting the safety catheter assembly of FIG. 30a in a second, safe position, wherein an actuator of the safety coupling has been shifted proximally, thereby releasing the catheter from the needle housing.

Thus, the actuator 604 can be received by the collar 606 and the catheter hub 114, and can include a wedge portion 660 that is shiftable between a first, ready for use position in which the at least one engagement arm 612 engages the catheter hub 114 (as depicted in FIGS. 27a and 28a), and a second, safe position in which the wedge portion 660 forces the engagement structure 610 open such that the at least one engagement arm 612 disengages the catheter hub 114 (as depicted in FIGS. 27b and 28b).

Referring to FIGS. 30a-b and 31a-b, the mounting collar 606 can be fixedly coupled to the distal end 146 of the needle housing 126 and can be shaped and sized to operably couple the actuator 604 and the engagement structure 610 to the needle housing 126. The needle housing 126 can include a needle lock 156 configured to inhibit movement of the needle assembly 128 from the second, safe position. In some versions, the needle lock 156 can include a bottleneck on the needle housing 126 that engages with a triangular protuberance 136 on the needle assembly 128 when in the second, safe position. The needle lock 156 and protuberance 136 are best depicted in FIGS. 4a-b.

The mounting collar 606 can be substantially cylindrical in shape with a through bore aperture 632 defined therein. Aperture 632 can be appropriately sized to receive a portion of the actuator 604. The aperture 632 can include a smaller diameter portion 634 and a larger diameter portion 636. The exterior surface 638 of the mounting collar 606 can define a guide groove 640 that is shaped and sized to receive a corresponding portion of the engagement structure 610. The mounting collar 606 can also include a tapered portion 642 configured to mate with the distal end 146 of the needle housing 126. In other versions, the mounting collar 606 can be integrally formed as a portion of needle housing 126.

As best depicted in FIG. 32, the nose 608 can be substantially cylindrical in shape with a through bore aperture 624 defined therein. The aperture 624 can include a smaller diameter portion 644 and a larger diameter portion 646. A change between the smaller diameter portion 644 and the larger diameter portion 646 can define a needle abutment 626. The sharp tip 108 of the needle 106 can be housed within the aperture 624 of the nose 608 when the needle transition 166 of the needle 106 is in contact with the needle abutment 626.

The nose 608 can include a nose portion 648 that is substantially cylindrical in shape and defines an internal hub contact 622. The nose portion 648 can be configured with a tapered blunt tip 650 sized to create a slip fit or a friction fit with a corresponding, internal surface 652 of the catheter hub 114. In some versions, the nose portion 648 is at least partially inserted into a socket 654 defined in catheter hub 114 when in the ready for use position, such that the nose portion 648 can apply a compressive force to a portion of the catheter hub 114, thereby opening the internal fluid passageway of catheter hub 114. The nose portion 648 can vary in diameter.

The nose 608 can include a ramp surface 656 formed as a part of a frustoconical portion 628. The frustoconical portion 628 can be tapered such that the diameter of the frustoconical portion 628 decreases as the distance from the nose portion 648 increases. At the base of the frustoconical portion 628, there is a substantially cylindrical portion 658. The frustoconical portion 628 can more generically be referred to as a wedge portion 660. Such a wedge portion 660 can include components with ramped or angled surfaces that can be used to help force open or expand the engagement structure 610.

The nose 608 can be operably coupled to the mounting collar 606 by a stay portion 662. The stay portion 662 can include multiple resilient arms 664 that each have a claw 666 that provides a distal, positive stop when in contact with a corresponding portion of the mounting collar 606. The stay portion 662 can be shaped and sized to fit within the aperture 632 of mounting collar 606 so that the actuator 604 and nose 608 can slide or shift distally and proximally relative to the mounting collar 606 along the axis of the needle 106.

As best depicted in FIGS. 33a-b, the "C" shaped engagement structure 610 is shiftable from a closed configuration to an open configuration. The engagement structure 610 generally includes engagement arms 612, mounting collar coupling arms 668, and an aperture 630. The engagement structure 610 can be operably coupled to a guide groove 640 of the mounting collar 606 by mounting collar coupling arms 668. For example, in one version, the mounting collar coupling arms 668 can be substantially "L" shaped, with one portion of each coupling arm 668 extending into the guide groove 640 of the mounting collar 606.

The engagement arms 612 can be shaped and sized to define external hub contacts 616 that contact and engage an outer surface of the catheter hub 114. The engagement arms 612 can include one or more notches or hub flange spaces 618 configured to retain a corresponding rim or flange 614 of the catheter hub 114. In this manner, the two opposed engagement arms 612 can form a "C-clamp" to grip and retain the catheter hub 114 relative to needle housing 126 when in the closed, engaged position. The engagement structure 610 can be constructed of a resilient material, such that at times the engagement arms 612 can be forced apart to release the catheter hub 114. In one version, the engagement arms 612 are biased toward one another, so that the engagement arms 612 are biased against the force applied by the ramp surface 656 of the actuator 604 to disengage the external hub contacts 616 when the actuator 604 is shifted to the proximal, disengaged position.

The aperture 630 in the engagement structure 610 can be sized to accommodate a portion of the nose 608, although different sizes and shapes are also contemplated. In one example embodiment, the aperture 630 includes a notch 670 and a split 672 to aid the ability of the engagement structure 610 to deform. A cylindrical portion 658 of the nose 608 can pass through the aperture 630 without restriction, thereby enabling the engagement structure 610 to remain in the closed, un-deformed shape. When the nose 608 and actuator 604 are shifted proximally, the frustoconical portion 628 can enter aperture 630 so that the ramp surface 656 forceably deforms the aperture 630 and separates the engagement arms 612 apart into the open position, where the external hub contacts 616 are removed from engagement with the catheter hub 114. The external hub contacts 616 can remain in contact, to some extent, with the catheter hub 114 in the disengaged position.

E. Fifth Embodiment

Referring to FIGS. 34a-40, a safety catheter assembly 700 according to a fifth embodiment of the disclosure is depicted. FIGS. 34a, 34b, 35a, and 36a depict the safety catheter assembly 700 in a first, ready for use position, where the actuator 704 of safety coupling 701 is shifted distally and external hub contacts 706 are in engagement with the catheter 104. FIGS. 34c, 35b, and 36b depict the safety catheter assembly 700 in the second, safe position, wherein the safety coupling 701 is shifted proximally, to a disengaged position associated with the needle assembly 128. FIGS. 34b and 34c depict a collar 708 omitted from the safety catheter assembly 700 to provide better views of internal components. FIGS. 35a-40 depict various components of the safety catheter assembly 700 in greater detail.

Figure 34A:
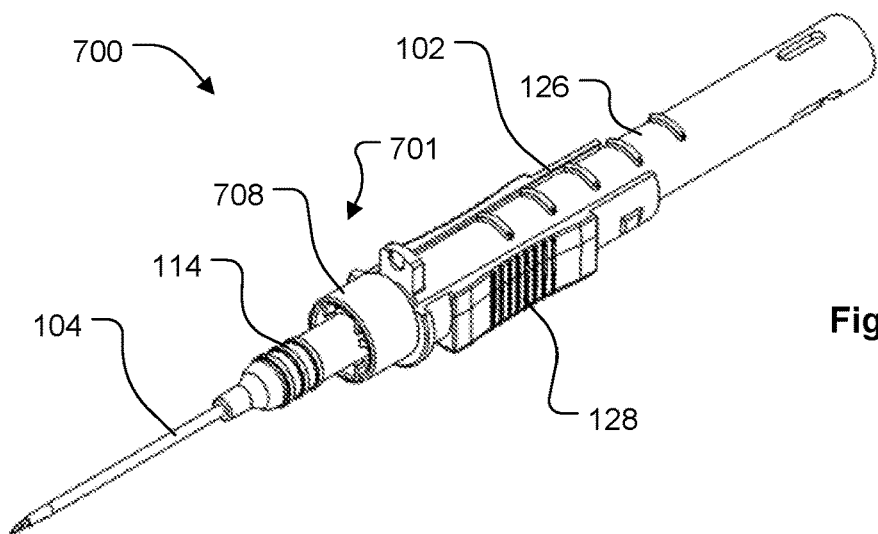
FIG. 34a is a perspective view depicting a safety catheter assembly according to a fifth embodiment of the disclosure, wherein the safety catheter assembly includes a catheter and a catheter insertion device and is in a first, ready for use position, wherein the catheter is securely connected to the catheter insertion device by a safety coupling including a collar.
Figure 34B:
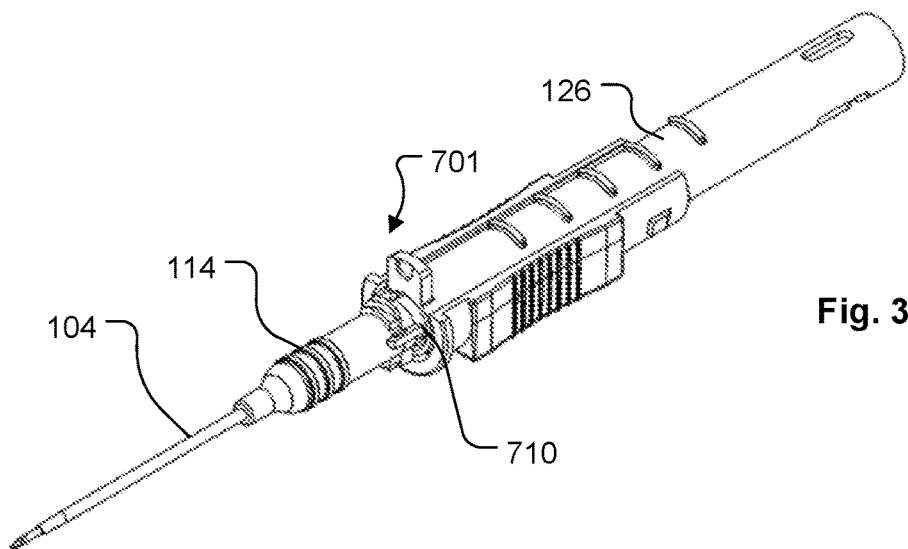
FIG. 34b is a perspective view depicting the safety catheter assembly of FIG. 34a with the collar removed to provide a better view of an actuator and an engagement structure of the safety coupling in the first, ready for use position.
Figure 34C:
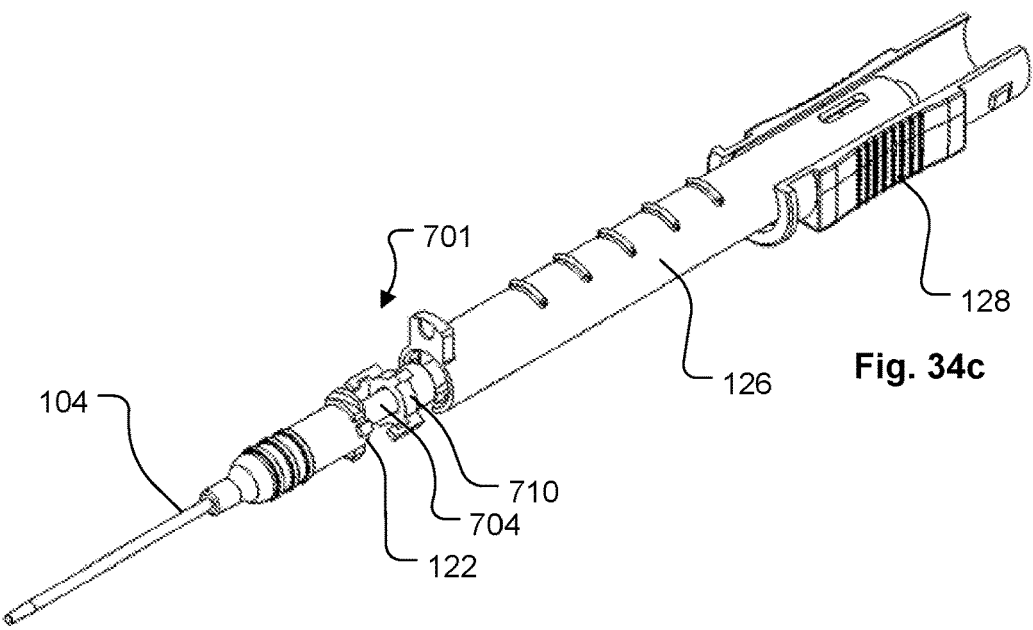
FIG. 34c is a perspective view depicting the catheter insertion device and the safety coupling of FIG. 34b, with the actuator and the engagement structure of the safety coupling in a second, safe position, wherein the catheter is released from the catheter insertion device and a sharp tip of an insertion needle of the catheter insertion device is safely housed within the catheter insertion device.
Figure 36A:
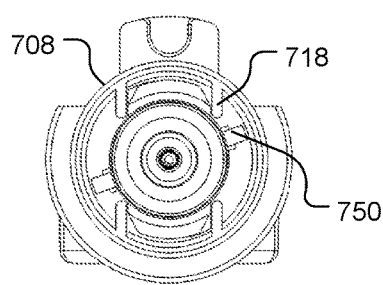
FIG. 36a is a distal end view depicting the safety catheter assembly of FIG. 35a in the first, ready for use position.
Figure 35A:
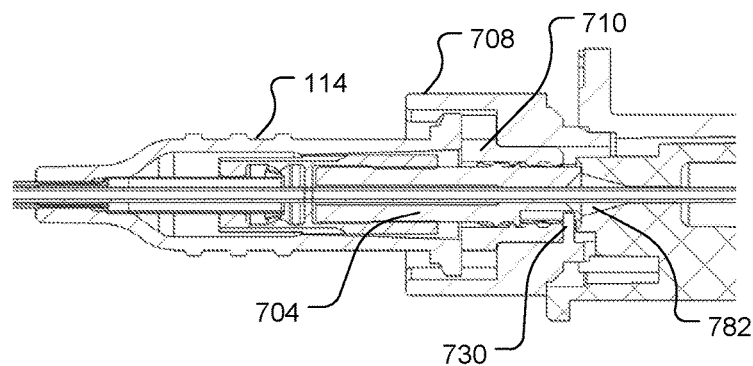
FIG. 35a is a fragmentary, side view depicting a safety catheter assembly according to a fifth embodiment of the disclosure in a first, ready for use position, wherein safety catheter assembly includes a safety coupling having an actuator and an engagement structure positioned relative to one another so as to engage a catheter of the safety catheter assembly.
Figure 36B:
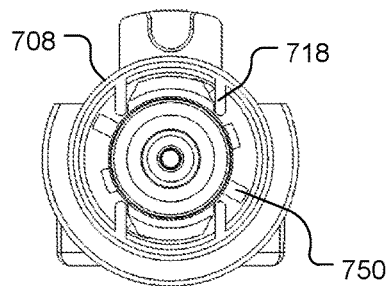
FIG. 36b is a distal end view depicting the safety catheter assembly of FIG. 35b in the second, safe position.
Figure 35B:
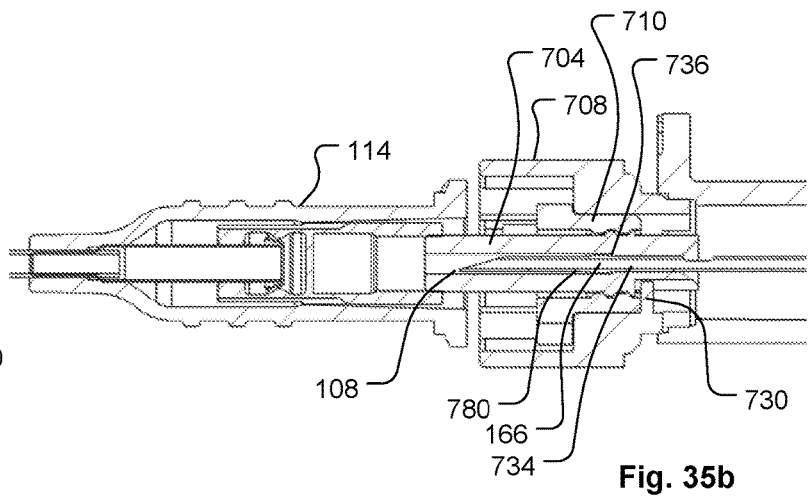
FIG. 35b is a fragmentary cross sectional view depicting the safety catheter assembly of FIG. 35a in a second, safe position, wherein the actuator has been shifted proximally, so as to rotate the engagement structure to release the catheter.

The safety catheter assembly 700 generally includes a catheter 104 and a safety catheter insertion device 102. The catheter 104 can include a catheter hub 114 and a catheter tube 112. The safety catheter insertion device 102, can be selectively connectable to the catheter hub 114, and can include a needle housing 126, a needle assembly 128, a collar 708, engagement structure 710, and actuator 704. The engagement structure 710 can be located within the collar 708, and include engagement arms 750. The engagement structure 710 can be axially rotatable relative to the collar between a first, engaged position (as depicted in FIGS. 34a and 35a), wherein the engagement arms 750 are engaged to the catheter hub 114, and a second, disengaged position (as depicted in FIGS. 34c and 35b), wherein the catheter hub 114 is removable from the engagement structure 710 and the collar 708. The actuator 704 can be located at least partially within the engagement structure 710, and can be axially shiftable relative to the engagement structure 710 and engaged to the engagement structure 710 by a plurality of helical features 724 whereby the engagement structure 710 is rotationally shifted as the actuator 704 is axially shifted.

The actuator 704 and nose 712 can be formed in a common, unitary structure and shift together between the proximal, engaged position and the distal, disengaged position. The engagement structure 710 can be formed in a separate unitary structure from the component 714 that includes the nose 712 and the actuator 704. The engagement structure 710 can rotate about the axis of needle 106 as the actuator is shifted proximally to disengage the catheter 104 from the safety coupling 701.

As best depicted in FIGS. 34a, 34b, 35a, and 36a, the collar 708 can be positioned in the ready for use position with the actuator 704 shifted distally, in the engaged position, located within the engagement structure 710. The catheter hub 114 can be positioned within the collar 708 and in contact with the engagement structure 710 so that lugs 716 of the catheter hub 114 are received between the vertical ribs 718. The hooks 720 of the engagement structure 710 can be engaged to fingers 722 of the catheter hub 114. The internal helical features 724 of the engagement structure 710 can be engaged to raised helical ridges 726 of the actuator 704. The raised helical ridges 726 of the actuator 704 can be engaged with the internal helical features 724 of the engagement structure 710. The actuator 704 can be constrained from rotating by interference between the axial slot 728 of the actuator 704 and the column 730 of the collar 708. The collar 708 can be secured to the needle housing 126 of the catheter insertion device 102, for example, by adhesives or a mechanical coupling, and the engagement structure 710 can be located within the collar 708.

The actuator 704 can be shifted proximally into a disengaged position, after the needle assembly 128 is moved to the safe position. In the safe position, the catheter hub 114 can be disengaged from the safety coupling 701, although contact can still exist therebetween. The actuator can be shifted proximally through interaction between the needle transition 166 and actuator 704 that occurs during the motion associated with needle 106 withdrawal. This can occur as the needle transition 166 is moved proximally through the needle passage 732 until the transition 166 encounters a narrower portion 734 of the needle passage 732 that includes a needle abutment 736. Interference between needle transition 166 and the needle abutment 736 can cause the actuator 704 to move along proximally with the needle 106 and needle assembly 128.

The engagement structure 710 can be free to rotate within the collar 708 to a limited degree. Proximal movement of the actuator 704 can urge the engagement structure 710 and the external hub contacts 706 out of engagement with the catheter hub 114 as the actuator 704 shifts proximally. The proximal movement of the actuator 704 can rotate the overall engagement structure 710 through interaction between helical features of each of the actuator 704 and the engagement structure 710. The engagement structure 710 can rotate within the collar 708 and about the catheter hub 114 generally without moving proximally as the actuator 704 shifts to the proximal position. This can result in the external hub contacts 706 formed on the inwardly extending portion 738 of engagement arms 750 being disengaged from corresponding fingers 722 on the external surface of the catheter hub 114. The catheter hub 114 can then be disengaged from engagement with the safety coupling 701, thereby enabling removal of the catheter 104 from the safety coupling 701 and the catheter insertion device 102. This disengagement can occur after the needle assembly 128 is in the safe position, wherein the sharp needle tip 108 lies internal to the nose 712 where unwanted needle sticks are inhibited, as in other example embodiments described herein. Distal movement from the nose 712 can be inhibited by engagement between the needle assembly 128 and a needle lock 156, as is discussed herein.

As best depicted in FIGS. 37a-b, the engagement structure 710 can be a generally unitary structure formed out of plastic or another suitable material of sufficient rigidity. The engagement structure 710 can be shiftable by rotation between an engaged position, wherein the external hub contacts 706 contact and engage the catheter hub 114, and a disengaged position, wherein the external hub contacts 706 are disengaged from the catheter hub 114.

The engagement structure 710 can include catheter engaging portion 740, collar engaging portion 742 and actuator engaging portion 744. The catheter engaging portion 740 can generally present an annular ring portion 746, blades 748 and engagement arms 750. The annular ring portion 746 can support blades 748 which can extend outwardly therefrom. The annular ring portion can also support engagement arms 750 which can extend outwardly and distally therefrom. The blades 748 can extend generally radially but can be angled (as depicted in FIGS. 37a-b). The engagement arms 750 can generally present a radially extending portion 752, a distally extending portion 754 and an inwardly extending portion 738. Together, the radially extending portion 752, the distally extending portion 754 and the inwardly extending portion 738 can surround and define finger engaging space 756. The external hub contacts 706 can lie on surfaces of the engagement arms 750 that face the finger engaging space 756 and that contact the outer surface of the catheter hub 114, when engaged thereto.

The collar engaging portion 742 generally presents a ring structure 758 and snap features 760. The snap features 760 can extend generally distally and include hooks 762 at a distal end thereof on the proximal end of the overall engagement structure. The snap features 760 can generally be resilient in structure. The actuator engaging portion 744 can be found within ring structure 758 and generally presents internal helical features 724, as shown. The internal helical features 724 can indent into or extend outwardly from ring structure 758 on an interior surface thereof.

As best depicted in FIG. 38, the collar 708 can be a generally unitary structure which can be formed of plastic or another sufficiently rigid material. The collar 708 can generally include a cylindrical body 764 having a distal extending portion 766 and a proximal extending portion 768. The distal extending portion 766 can be of a larger diameter than proximal extending portion 768. The proximal extending portion 768 can be structured to engage to the needle housing 126 of a catheter insertion device 102 and can be secured thereto by adhesive or mechanical coupling. The distal extending portion can present vertical ribs 718 extending generally inwardly therefrom. Four vertical ribs 718 can be configured in two generally parallel pairs. A column 730 can extend generally inwardly from the proximal extending portion 768. A distal extending portion 766 can surround and define a hub receiving space 770. The proximal extending portion 768 can generally surround and define engagement structure receiving cavity 772.

As best depicted in FIGS. 39a and 39b, component 714, referred to herein alternately as the nose 712 or the actuator 704, can be an elongate generally cylindrical structure and can be formed of a plastic for example or another material of sufficient rigidity. The actuator 704 generally can include a nose portion 774, a helix portion 776 and a slot portion 778. The nose portion 774 can be generally cylindrical in structure and extend distally. The helix portion 776 can be proximal to the nose portion 774 and can present raised helical ridges 726. The raised helical ridges 726 can be replaced by helical slots in alternative example embodiments.

The slot portion 778 can be located proximal of the helix portion 776 and can define therein an axial slot 728. The axial slot 728 can be oriented generally parallel to the central axis of the overall component 714 and the needle 106 of the catheter insertion device 102. The axial slot 728 can be sized to accommodate a column 730.

The actuator 704 defines needle passage 732 passing axially therethrough. The needle passage 732 can presents a wider portion 780 and a narrower portion 734. The wider portion 780 can be sized to receive the needle 106 and the needle transition 166. The narrower portion 734 can be sized to receive the needle 106 therethrough, while excluding the passage of needle transition 166 at a needle abutment 736. The actuator 704 can also present and define a proximal funnel 782 at a proximal end thereof.

As best depicted in FIG. 40, the catheter hub 114 can include a hub body 784 formed of plastic or another sufficiently rigid material. The hub body 784 can include a tapered distal end 120 and a proximal end 122. The hub body 784 can present ribs or lugs 716 at the proximal end 122. In addition, the hub body 784 can present fingers 722 extending radially outwardly therefrom. The fingers 722 can be located diametrically from one another. In the depicted version, the fingers 722 are generally rectangular in structure. The fingers 722 can be sized and shaped to fit within the finger engaging spaces 756 of the engagement structure 710 where contact is made with the external hub contacts 706 of the engagement structure 710.

F. Sixth Embodiment

Figure 42A:
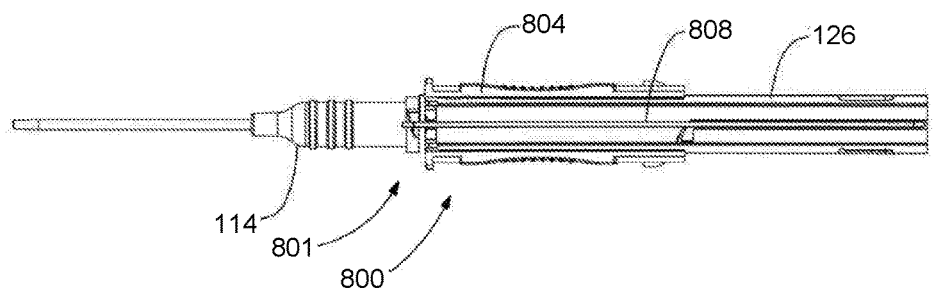
FIG. 42a is a top view depicting the safety catheter assembly of FIG. 41a in the first, ready for use position, wherein a safety rod of the safety coupling couples the catheter to the catheter insertion device.
Figure 42B:
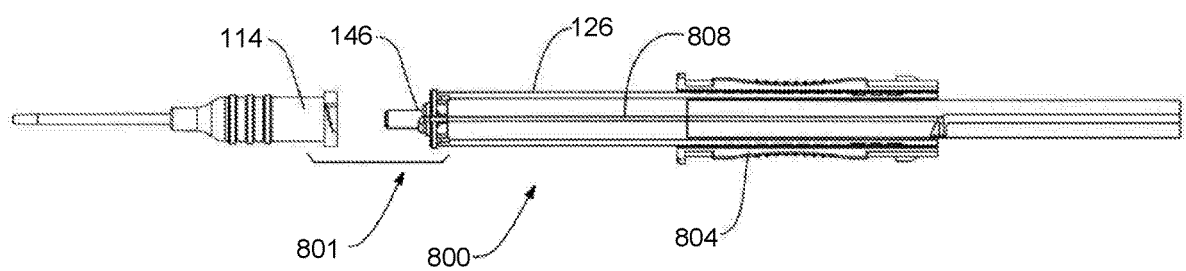
FIG. 42b is a top view depicting the safety catheter assembly of FIG. 42a, in the second, safe position, wherein the safety rod is pivoted to release the catheter from the catheter insertion device.
Figure 43:
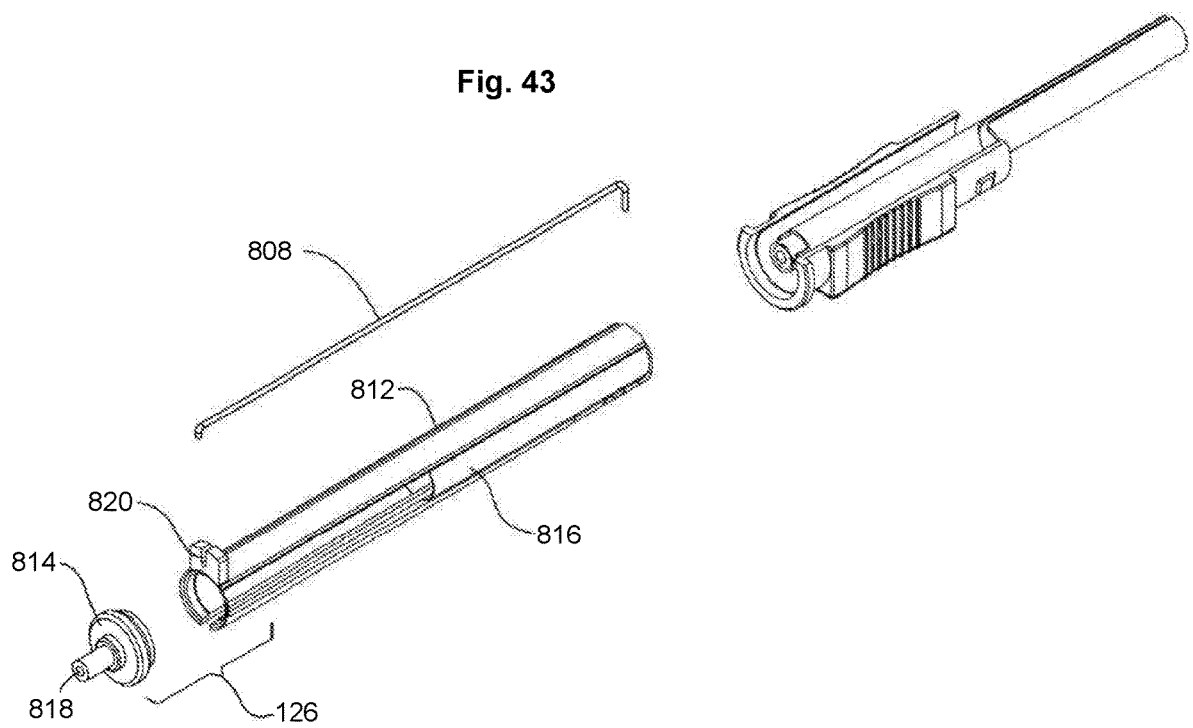
FIG. 43 is an exploded perspective view depicting a nose portion, needle housing, needle assembly, and safety rod of a safety catheter assembly according to a sixth embodiment of the disclosure.
Figure 44:
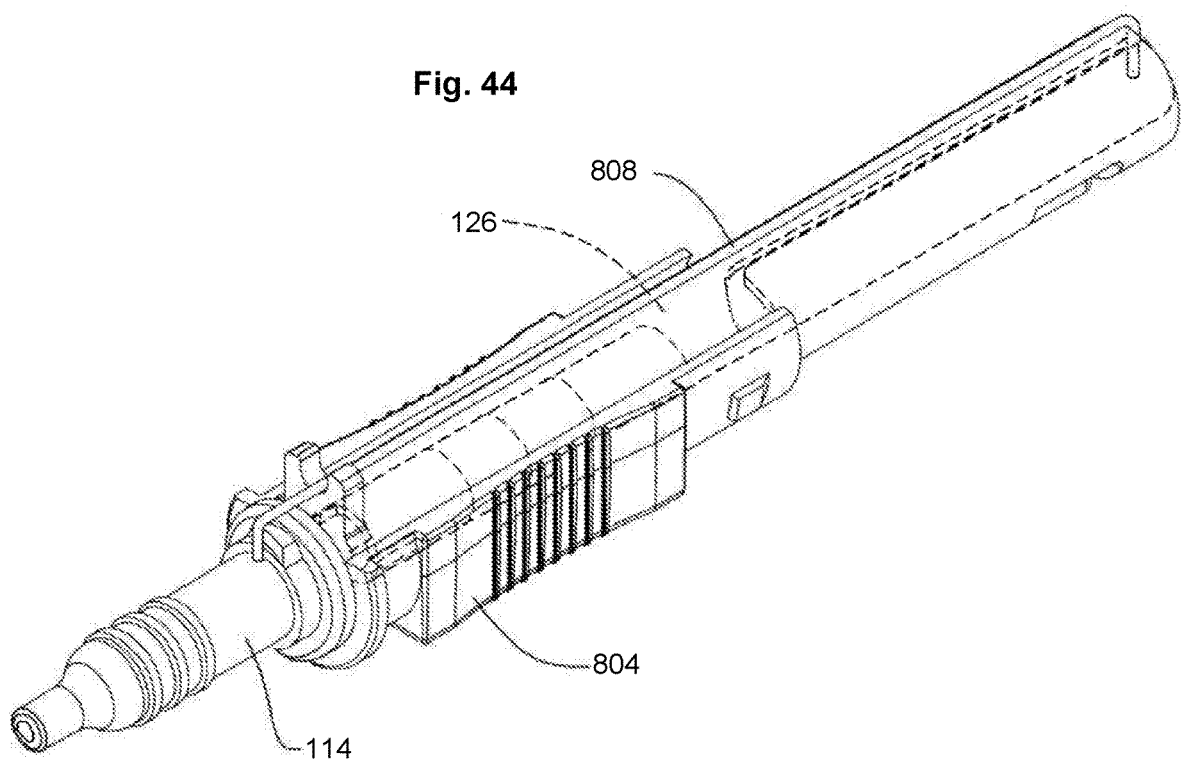
FIG. 44 is a perspective view depicting a catheter hub coupled to a needle housing according to a sixth embodiment of the disclosure, wherein the catheter hub is coupled to the needle housing by a safety rod, and one end of the safety rod is inserted into a safety rod channel formed into a needle hub that is slidably engaged to the needle housing.
Figure 45:
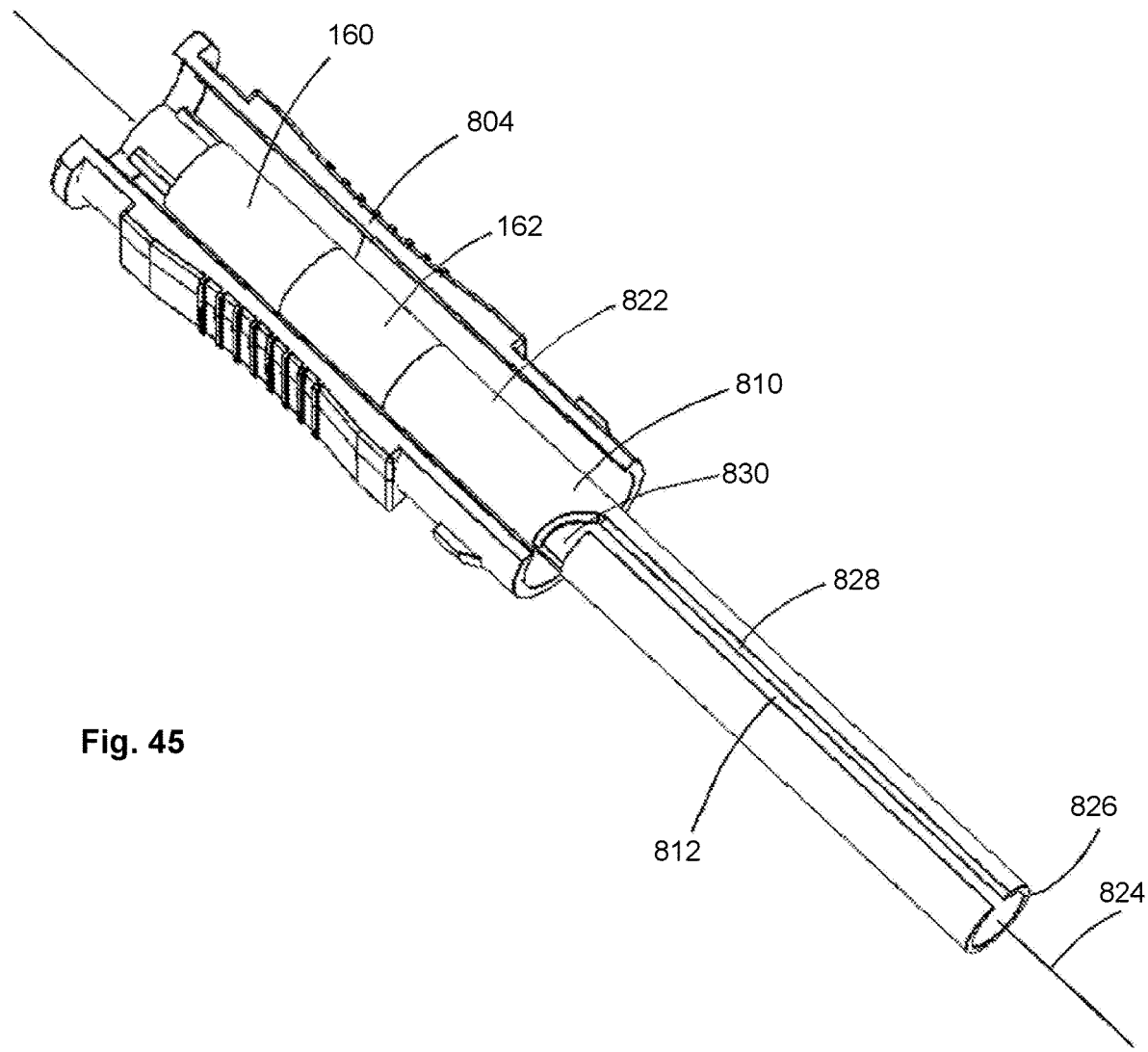
FIG. 45 is a top perspective view of the needle housing of FIG. 44.

Referring to FIGS. 41a-46b, a safety catheter assembly 800 according to a sixth embodiment of the disclosure is depicted. FIGS. 41a, 42a, and 44 depict the safety catheter assembly 800 in a ready for use position, wherein the needle assembly 804 is shifted distally and catheter hub engaging portion 806 of the safety rod 808 is in engagement with the catheter 104. FIGS. 41b and 42b depict the safety catheter assembly 800 in the safe position, wherein the needle assembly 804 is shifted proximally, in which the catheter hub engaging portion 806 of the safety rod 808 is in a disengaged position from the catheter 104. FIGS. 43 and 45-46b depict various components of the safety catheter assembly 800 in greater detail.

The safety catheter assembly 800 includes similarities and differences with respect to other example embodiments described herein. Similar to other embodiments, the safety catheter assembly 800 includes a catheter 104 having a catheter hub 114 and a catheter tube 112 as well as a safety catheter insertion device 102 that is selectively connectable to the catheter hub 114. The safety catheter insertion device 102, is somewhat different, however, as it can include a needle assembly 804 with a tail portion 810 having a channel 812 defined within. The embodiment is also somewhat different as it can include a safety rod 808 having a catheter hub engaging portion 806 that is disposed in the channel 812 and is caused to pivot into a hub disengagement position based on movement of the needle housing 126 upon reaching the safe position. Unlike other previous embodiments discussed, the example embodiment does not include a collar that surrounds the catheter hub 114 and does not include an actuator located near the distal end of the needle housing 146.

The safety catheter insertion device 102 can be selectively connectable to the catheter hub 114 and can include a needle housing 126, needle assembly 804, and safety rod 808. The needle assembly 804 can include a needle 106 and a needle hub 132 with a tail portion 810 having a safety rod channel 812 defined therein. The needle assembly 804 can be slideably coupled to the needle housing 126 between a first, ready for use position (depicted in FIG. 41a), wherein a portion of the needle 106 extends through the catheter hub 114 and exposes a sharpened tip 108, and a second, safe position (depicted in FIG. 41b), wherein the sharpened tip 108 of the needle 106 is housed by the needle housing 126 to inhibit an inadvertent needle stick. The safety rod 808 can have a catheter hub engaging portion 806 and a guide portion 832, wherein the guide portion 832 can traverse the safety rod channel 812 of the needle assembly 804 when the needle assembly 804 is retracted from the first, ready for use position to the second, safe position, including pivotal interaction with the safety rod channel 812 that causes the catheter hub engaging portion 806 to rotate from a first, catheter hub retention position to a second, catheter hub disengagement position.

As best depicted in FIGS. 41a-42b, safety catheter assembly 800 can include a safety catheter insertion device 102, which generally can include a needle housing 126, a safety rod 808 and a needle assembly 804 including a tail portion 810 having a safety rod channel 812. The needle housing 126 can be configured to be selectively coupled to catheter hub 114.

As best depicted in FIG. 43, the needle housing 126 can be comprised of a nose portion 814 and a needle housing body 816. Nose portion 814 can be configured with a tapered blunt tip sized to create a friction fit with a portion of catheter hub 114. The nose portion 814 can be at least partially inserted into a socket defined in catheter hub 114, such that nose portion 814 applies a compressive force to a portion of catheter hub 114, thereby opening the internal fluid passageway of catheter hub 114. The nose portion 814 can further define an aperture 818 through which needle 106 can pass. In some versions, the needle housing 126 includes a needle lock 156 configured to inhibit movement of the needle assembly 804 from the second, safe position. The needle lock 156 can include a bottleneck 156 on the needle housing 126 that engages with a triangular protuberance 136 on the needle assembly 804 when in the second, safe position.

The nose portion 814 can be fixedly coupled to needle housing 126. The needle housing 126 can be generally tubular in shape with a number of defining features. For example, in addition to longitudinal slot 150 and needle lock 156 as disclosed previously, needle housing 126 can include a protrusion 820 and a channel 812 for receiving a portion of safety rod 808. The protrusion 820 can be shaped and sized to provide a grip or surface for a user to push against when actuating needle assembly 804. Protrusion 820 can be defined by channel 812 and can be configured to enable safety rod 808 to pass there through. The channel 812 can extend along the entire length, or a portion of the entire length, of needle housing 126. The channel 812 can be shaped and sized to accommodate a portion of safety rod 808, so that safety rod 808 is partially, embedded within needle housing 126 yet is configured to pivot relative to needle housing 126. In some versions, the needle assembly 804 includes a flash chamber 160 with a flash plug 162.

As best depicted in FIGS. 41a, 41b, and 42a-44, the needle assembly 804 can include a fixedly coupled needle 106 and be slideably coupled to needle housing 126 between a first, ready for use position, wherein a portion of the hollow needle extends through catheter hub 114 and a second, safe position, wherein a sharpened tip 108 of the needle 106 is shielded by the needle housing 126 to inhibit an inadvertent needle stick. With additional reference to FIGS. 45-46b, the needle assembly 804 can further be defined by a tail portion 810 having a safety rod channel 812.

The needle assembly 804 can include a flash chamber 160. Flash chamber 160 can be configured as a cavity in fluid communication with the lumen of hypodermic needle 106 opposite sharpened tip 108. The flash chamber 160 can be constructed of a transparent or translucent material to enable a clinician to visually see when fluid enters the flash chamber 160. The rear of flash chamber 160 can be plugged with a microporous flash plug 162. Flash plug 162 can be comprised of a material that enables air to vent from the flash chamber 160 as fluid fills the chamber, but inhibit the fluid from passing from the flash chamber 160.

The flash chamber 160 and tail portion 810 can be defined by the same tubular wall 822, with flash plug 162 serving as the divider between the flash chamber 160 and the tail portion 810. The safety rod channel 812 can be defined in tubular wall 822 of tail portion 810. The safety rod channel 812 can extend linearly along the axis 824 of tail portion 810 from the distal end 826 of tail portion 810 towards flash plug 162. Prior to reaching flash plug 162, safety rod channel 812 can deviate from its linear path 828 along the axis 824 of tail portion 810 to form a "J" hook 830 laterally to either side of the linear path along the axis 824 of tail portion 810. The safety rod channel 812 can be sized to enable a portion of safety rod 808 to freely pass therethrough, so that a portion of safety rod 808 can traverse along safety rod channel 812 when needle assembly 804 is moved from the first position (as depicted in FIGS. 41a and 42a) to the second position (as depicted in FIGS. 41b and 42b).

The safety rod 808 can be formed of a piece of wire or the like. With continued reference to FIGS. 46a-46b, the safety rod 808 can be defined by a guide portion 832 and a catheter hub engaging portion 806 spaced apart by an elongated portion 834. The guide portion 832 can be configured to slidingly fit within safety rod channel 812, while the catheter hub engaging portion 806 can be configured to be positioned so as to maintain the coupling of catheter huh 114 to needle housing 126. The catheter hub engaging portion 806 and elongated portion 168 can be substantially orthogonal to elongated portion 168. The guide portion 832 and the catheter hub engaging portion 806 can be parallel to one another.

In operation, the safety catheter assembly 800 including safety coupling 801 can be supplied in an assembled state with catheter hub 114 secured to needle housing 126 and held in place with the assistance of safety rod 808. Specifically, the catheter hub engaging portion 806 of safety rod 808 can be in a position that inhibits free removal of catheter hub 114 from needle housing 126. Accordingly, as delivered, the configuration of safety catheter assembly 800 can be substantially as depicted in FIGS. 41a and 42a.

When it is desired to separate catheter hub 114 from safety coupling 801, the needle 106 is moved proximally by movement of needle assembly 804 in a proximal direction. As needle assembly 804 is moved from the first position to the second position, guide portion 832 of safety rod 808 traverses along safety rod channel 812. When guide portion 832 traverses along safety rod channel 812 to the "J" hook 830, the safety rod 808 will pivot relative to needle housing 126, thereby causing catheter hub engaging portion 806 to move from a catheter hub retention position to a disengaged position whereby the catheter hub 114 can be removed from the needle housing 126 without interference from the safety rod 808. Catheter hub 114 can then be disengaged from needle housing 126, as shown in FIGS. 41b and 42b.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A catheter insertion device for use with a catheter assembly having a catheter hub and a catheter extending from a distal end of the catheter hub, the catheter hub having an exterior and an interior defining an internal cavity, the catheter insertion device comprising:
- a needle slidable through the catheter having a distal tip, a proximal end and a needle transition proximal to the distal tip, the needle attached to a needle hub, the needle hub movable between a ready for use position and a safe position;
- a collar movable longitudinally relative to the catheter hub, the collar having at least one external hub contact; and
- a retainer having at least one portion slidably engaged within the collar, the retainer having a distal portion that extends distally from the collar and an engagement structure having at least one interior hub contact proximal the distal portion and a passage through which the needle axially passes;
- wherein when the needle hub is in the ready for use position, the distal portion of the retainer is positioned inside the internal cavity of the catheter hub distal from the collar with the at least one interior hub contact of the retainer in contact with the interior of the catheter hub proximal from the distal portion, and the at least one external hub contact of the collar is in a gripping contact with the exterior of the catheter hub;
- wherein proximal movement of the needle hub relative to the collar from the ready for use position to the safe position causes the needle transition to shift the retainer proximally relative to the catheter hub such that the at least one interior hub contact of the retainer disengages from the interior of the catheter hub and the at least one external hub contact of the collar disengages from the exterior of the catheter hub to enable the catheter hub and the collar to separate from each other; and
- wherein the distal tip of the needle is positioned within the passage of the retainer when the catheter hub and the collar are separated from each other.

2. The catheter insertion device of claim 1, wherein the at least one external hub contact of the collar includes at least two exterior hub contact surfaces.

3. The catheter insertion device of claim 1, wherein the at least one interior hub contact of the retainer inhibits removal of the catheter hub from the collar when the catheter insertion device is in the ready for use position.

4. The catheter insertion device of claim 1, further comprising a needle housing having a needle lock configured to interact with a protuberance on the needle hub to lock the needle hub relative to the needle housing in the safe position.

5. The catheter insertion device of claim 4, wherein in the safe position, the needle lock is positioned proximally to the needle transition.

6. The catheter insertion device of claim 4, wherein in the safe position, the needle lock is positioned proximally to the proximal end of the needle.

7. The catheter insertion device of claim 1, wherein at least a portion of the needle is positioned within the collar when the catheter insertion device is moving from the ready for use position to the safe position.

8. The catheter insertion device of claim 1, wherein the needle hub includes a flash chamber.

9. The catheter insertion device of claim 1, wherein the needle includes a notch proximal the distal tip configured to enable blood to pass therethrough into an annular space between an exterior of the needle and an interior of the catheter.

10. The catheter insertion device of claim 1, wherein the collar is positioned circumferentially about at least a portion of the distal portion of the retainer in the ready for use position.

11. The catheter insertion device of claim 1, wherein the retainer and the distal portion are integrally formed as a single component.

12. The catheter insertion device of claim 1, wherein proximal movement of the needle hub relative to the collar to the safe position causes the needle transition to shift the distal portion of the retainer proximally out of the internal cavity of the catheter hub.

13. The catheter insertion device of claim 1, wherein the interior internal cavity of the catheter hub has a blood control valve; and
- wherein the distal portion of the retainer is adapted to contact the blood control valve in an engaged position.

14. A safety catheter assembly comprising:
- a catheter hub having a body along a longitudinal axis including an interior surface and an exterior surface, a distal end from which a catheter having a distal end extends, an open proximal end and an internal cavity defined by the interior surface;
- a needle having a cross section dimension adapted to slidably extend through the catheter hub and along the catheter, the needle having a proximal end attached to a needle hub, a distal tip adapted to extend beyond the distal end of the catheter when the needle is in a ready for use position, and a transition proximal the distal tip having a cross section dimension different from the cross section dimension of the needle;
- a collar positioned relative to the needle hub and movable relative to the catheter hub along the longitudinal axis, the collar having an open distal end and at least one external contact adapted to engage the exterior surface of the catheter hub;
- a retainer having a passage through which the needle slidably extends, the retainer having at least a proximal portion slidably engaged within the collar and a distal portion adapted to be positioned in the internal cavity of the catheter hub, the retainer having a wall proximal of the distal portion adapted to contact the open proximal end of the catheter hub in the ready for use position and at least one internal contact proximal the distal portion adapted to engage the interior surface of the catheter hub;
- wherein when the needle is in the ready for use position, the open distal end of the collar is positioned about at least the open proximal end of the catheter hub with the at least one external contact of the collar engaged to the exterior surface of the catheter hub, the distal portion of the retainer is positioned inside the internal cavity of the catheter hub with the at least one internal contact engaged to the interior surface of the catheter hub proximal the distal portion, and the distal tip of the needle is extended beyond the distal end of the catheter.

15. The safety catheter assembly of claim 14, wherein when the needle hub is moved in a proximal direction relative to the catheter hub to a safe position, the needle is removed from the catheter and when the transition comes into contact with a needle abutment at the retainer, the distal tip of the needle is positioned inside the passage of the retainer; and wherein continued proximal movement of the needle causes the retainer to move proximally relative to the catheter hub, the at least one internal contact to disengage from the interior surface of the catheter hub and the at least one external contact of the collar to disengage from the exterior surface of the catheter hub such that the catheter hub is separable from the retainer and the collar.

16. The safety catheter assembly of claim 14, further comprising a blood control valve positioned inside the internal cavity of the catheter hub, the blood control valve is adapted to be contacted by the distal portion of the retainer.

17. The safety catheter assembly of claim 16, wherein the distal portion of the retainer contacts the blood control valve to provide a seal that helps to contain flashback blood.

18. The safety catheter assembly of claim 14, wherein the distal portion comprises an elongated nose extending from a proximal extension of the retainer; and wherein the at least one internal contact comprises a protrusion distal the proximal extension that has a radial extension adapted to be in contact with the interior surface of the catheter hub when the needle is in the ready for use position.

\* \* \* \* \*